United States Patent
Gaudiani

(10) Patent No.: US 12,303,684 B1
(45) Date of Patent: May 20, 2025

(54) TRANSCORONARY SINUS PACING OF POSTEROSEPTAL LEFT VENTRICULAR BASE

(71) Applicant: Vincent A. Gaudiani, Portola Valley, CA (US)

(72) Inventor: Vincent A. Gaudiani, Portola Valley, CA (US)

( * ) Notice: Subject to any disclaimer, the term of this patent is extended or adjusted under 35 U.S.C. 154(b) by 0 days.

(21) Appl. No.: 18/624,390

(22) Filed: Apr. 2, 2024

Related U.S. Application Data

(63) Continuation of application No. 18/295,368, filed on Apr. 4, 2023, now Pat. No. 11,975,189, which is a continuation of application No. 16/806,356, filed on Mar. 2, 2020, now Pat. No. 11,648,397, which is a continuation-in-part of application No. 16/593,061, filed on Oct. 4, 2019, now Pat. No. 11,577,075.

(60) Provisional application No. 62/897,724, filed on Sep. 9, 2019, provisional application No. 62/744,833, filed on Oct. 12, 2018.

(51) Int. Cl.
*A61N 1/00* (2006.01)
*A61N 1/05* (2006.01)
*A61N 1/375* (2006.01)

(52) U.S. Cl.
CPC ....... *A61N 1/0573* (2013.01); *A61N 1/37512* (2017.08); *A61N 1/37518* (2017.08); *A61N 2001/058* (2013.01)

(58) Field of Classification Search
CPC .................................................. A61N 1/0573
See application file for complete search history.

(56) References Cited

U.S. PATENT DOCUMENTS

| | | | |
|---|---|---|---|
| 3,995,623 | A | 12/1976 | Blake et al. |
| 4,917,102 | A | 4/1990 | Miller et al. |
| 5,477,864 | A | 12/1995 | Davidson |
| 5,549,109 | A | 8/1996 | Samson et al. |
| 5,662,109 | A | 9/1997 | Hutson |
| 5,919,213 | A | 7/1999 | Nelson et al. |
| 5,944,746 | A | 8/1999 | Kroll |
| 5,957,956 | A | 9/1999 | Kroll et al. |

(Continued)

FOREIGN PATENT DOCUMENTS

| | | |
|---|---|---|
| WO | WO-03086502 A2 | 10/2003 |
| WO | WO-03086502 A3 | 4/2004 |
| WO | WO-2008042887 A1 | 4/2008 |

OTHER PUBLICATIONS

Co-pending U.S. Appl. No. 18/147,601, inventor Gaudiani; Vincent A., filed Dec. 28, 2022.

(Continued)

*Primary Examiner* — Joseph M Santos Rodriguez
(74) *Attorney, Agent, or Firm* — WILSON SONSINI GOODRICH & ROSATI

(57) ABSTRACT

Systems and methods for cardiac pacing are provided, where a pacing lead is placed at or near the bundle of His. A method for pacing a heart of a patient comprises: introducing a sheath to vasculature of the patient; steering the sheath within a coronary sinus in the heart to lodge a distal end of the sheath to a target location proximal to the bundle of His above a septum separating a left ventricle and a right ventricle of the heart; advancing a pacing lead through a lumen of the sheath to the target location; coupling the pacing lead to cardiac tissue at the target location; removing the sheath; and electrically pacing the bundle of His using the pacing lead.

20 Claims, 25 Drawing Sheets

(56) References Cited

U.S. PATENT DOCUMENTS

| | | | |
|---|---|---|---|
| 6,027,476 A | 2/2000 | Sterman et al. |
| 6,067,471 A | 5/2000 | Warren |
| 6,094,597 A | 7/2000 | Wold |
| 6,152,141 A | 11/2000 | Stevens et al. |
| 6,217,369 B1 | 4/2001 | Shchervinsky et al. |
| 6,275,734 B1 | 8/2001 | McClure et al. |
| 6,282,444 B1 | 8/2001 | Kroll et al. |
| 6,356,791 B1 | 3/2002 | Westlund et al. |
| 6,363,280 B1 | 3/2002 | Mouchawar et al. |
| 6,377,852 B1 | 4/2002 | Bornzin et al. |
| 6,493,591 B1 | 12/2002 | Stokes |
| 6,567,697 B1 | 5/2003 | Kroll et al. |
| 6,574,505 B1 | 6/2003 | Warren |
| 6,625,489 B2 | 9/2003 | Sheth et al. |
| 6,633,780 B1 | 10/2003 | Berger |
| 6,671,560 B2 | 12/2003 | Westlund et al. |
| 6,675,042 B2 | 1/2004 | Swerdlow et al. |
| 6,701,187 B1 | 3/2004 | Bornzin et al. |
| 6,723,069 B1 | 4/2004 | Weldon et al. |
| 6,723,082 B1 | 4/2004 | Payne et al. |
| 6,728,563 B2 | 4/2004 | Rashidi |
| 6,733,499 B2 | 5/2004 | Scheib |
| 6,733,500 B2 | 5/2004 | Kelley et al. |
| 6,736,782 B2 | 5/2004 | Pfeiffer et al. |
| 6,741,878 B2 | 5/2004 | Fuimaono et al. |
| 6,746,431 B2 | 6/2004 | Pfeiffer et al. |
| 6,748,255 B2 | 6/2004 | Fuimaono et al. |
| 6,775,566 B2 | 8/2004 | Nissila et al. |
| 6,782,291 B1 | 8/2004 | Bornzin et al. |
| 6,788,972 B2 | 9/2004 | Prutchi et al. |
| 6,792,316 B2 | 9/2004 | Sass |
| 6,792,318 B2 | 9/2004 | Chitre et al. |
| 6,804,553 B2 | 10/2004 | Zheng et al. |
| 6,807,447 B2 | 10/2004 | Griffin et al. |
| 6,821,265 B1 | 11/2004 | Bertolero et al. |
| 6,823,215 B2 | 11/2004 | Obel et al. |
| 6,826,421 B1 | 11/2004 | Beatty et al. |
| 6,830,568 B1 | 12/2004 | Kesten et al. |
| 6,835,188 B2 | 12/2004 | Samson et al. |
| 6,837,864 B1 | 1/2005 | Bertolero et al. |
| 6,839,588 B1 | 1/2005 | Rudy |
| 6,849,073 B2 | 2/2005 | Hoey et al. |
| 6,850,800 B1 | 2/2005 | Uhrenius et al. |
| 6,859,667 B2 | 2/2005 | Goode |
| 6,868,291 B1 | 3/2005 | Bonner et al. |
| 6,882,886 B1 | 4/2005 | Witte et al. |
| 6,889,093 B1 | 5/2005 | Flammang |
| 6,892,091 B1 | 5/2005 | Ben-Haim et al. |
| 6,901,288 B2 | 5/2005 | Janke et al. |
| 6,901,297 B2 | 5/2005 | Frericks et al. |
| 6,902,545 B2 | 6/2005 | Bertolero et al. |
| 6,904,315 B2 | 6/2005 | Panken et al. |
| 6,907,296 B1 | 6/2005 | Doan et al. |
| 6,907,297 B2 | 6/2005 | Wellman et al. |
| 6,909,916 B2 | 6/2005 | Spinelli et al. |
| 6,909,919 B2 | 6/2005 | Jain et al. |
| 6,916,317 B2 | 7/2005 | Falwell et al. |
| 6,926,669 B1 | 8/2005 | Stewart et al. |
| 6,934,583 B2 | 8/2005 | Weinberg et al. |
| 6,937,897 B2 | 8/2005 | Min et al. |
| 6,944,506 B1 | 9/2005 | Morgan et al. |
| 6,947,785 B1 | 9/2005 | Beatty et al. |
| 6,950,696 B2 | 9/2005 | Bjorling et al. |
| 6,960,206 B2 | 11/2005 | Keane |
| 6,961,602 B2 | 11/2005 | Fuimaono et al. |
| 6,961,621 B2 | 11/2005 | Krishnan et al. |
| 6,968,237 B2 | 11/2005 | Doan et al. |
| 6,970,733 B2 | 11/2005 | Willis et al. |
| 6,973,340 B2 | 12/2005 | Fuimaono et al. |
| 6,973,341 B2 | 12/2005 | Watson |
| 6,973,352 B1 | 12/2005 | Tsutsui et al. |
| 6,984,232 B2 | 1/2006 | Vanney et al. |
| 6,986,769 B2 | 1/2006 | Nelson et al. |
| 6,987,996 B2 | 1/2006 | Fuimaono et al. |
| 6,987,999 B1 | 1/2006 | Kroll |
| 6,988,007 B1 | 1/2006 | Morgan et al. |
| 6,999,814 B2 | 2/2006 | Hauser et al. |
| 6,999,821 B2 | 2/2006 | Jenney et al. |
| 7,010,358 B1 | 3/2006 | Kroll et al. |
| 7,027,876 B2 | 4/2006 | Casavant et al. |
| 7,031,773 B1 | 4/2006 | Levine et al. |
| 7,039,450 B2 | 5/2006 | Duarte |
| 7,041,079 B2 | 5/2006 | Yozu et al. |
| 7,047,068 B2 | 5/2006 | Haissaguerre |
| 7,081,114 B2 | 7/2006 | Rashidi |
| 7,085,606 B2 | 8/2006 | Flach et al. |
| 7,089,045 B2 | 8/2006 | Fuimaono et al. |
| 7,089,065 B2 | 8/2006 | Westlund et al. |
| 7,097,641 B1 | 8/2006 | Arless et al. |
| 7,099,712 B2 | 8/2006 | Fuimaono et al. |
| 7,103,409 B2 | 9/2006 | Warren |
| 7,110,827 B2 | 9/2006 | Sage et al. |
| 7,151,963 B2 | 12/2006 | Havel et al. |
| 7,158,825 B1 | 1/2007 | Kroll et al. |
| 7,177,704 B2 | 2/2007 | Laske et al. |
| 7,184,839 B2 | 2/2007 | Clemens et al. |
| 7,200,434 B2 | 4/2007 | Havel et al. |
| 7,203,546 B1 | 4/2007 | Kroll et al. |
| 7,203,547 B1 | 4/2007 | Kroll et al. |
| 7,558,631 B2 | 7/2009 | Cowan et al. |
| 7,647,124 B2 | 1/2010 | Williams |
| 8,068,920 B2 | 11/2011 | Gaudiani |
| 8,078,287 B2 | 12/2011 | Liu et al. |
| 8,406,899 B2 | 3/2013 | Reddy et al. |
| 8,634,935 B2 | 1/2014 | Gaudiani |
| 8,700,181 B2 | 4/2014 | Bornzin et al. |
| 8,812,106 B2 | 8/2014 | Ortega et al. |
| 9,008,768 B2 | 4/2015 | Zhu et al. |
| 9,168,382 B2 | 10/2015 | Shuros et al. |
| 9,265,938 B2 | 2/2016 | Gaudiani |
| 9,579,501 B2 | 2/2017 | Shuros et al. |
| 10,369,356 B2 | 8/2019 | Vincent |
| 11,577,075 B1 | 2/2023 | Gaudiani |
| 11,648,397 B1 | 5/2023 | Gaudiani |
| 11,975,189 B1 | 5/2024 | Gaudiani |
| 2002/0077685 A1 | 6/2002 | Sundquist et al. |
| 2003/0050670 A1 | 3/2003 | Spinelli et al. |
| 2003/0078645 A1 | 4/2003 | Pigott |
| 2004/0015193 A1 | 1/2004 | Lamson et al. |
| 2005/0209668 A1 | 9/2005 | Friedman et al. |
| 2005/0251130 A1 | 11/2005 | Boveja et al. |
| 2006/0106442 A1 | 5/2006 | Richardson et al. |
| 2006/0241465 A1 | 10/2006 | Huennekens et al. |
| 2006/0247750 A1 | 11/2006 | Seifert et al. |
| 2008/0082136 A1 | 4/2008 | Gaudiani |
| 2012/0041530 A1 | 2/2012 | Gaudiani |
| 2012/0158111 A1 | 6/2012 | Khairkhahan et al. |
| 2012/0232563 A1 | 9/2012 | Williams et al. |
| 2013/0116738 A1 | 5/2013 | Samade et al. |
| 2013/0123872 A1 | 5/2013 | Bornzin et al. |
| 2014/0107723 A1 | 4/2014 | Hou et al. |
| 2014/0257101 A1 | 9/2014 | Gaudiani |
| 2014/0257324 A1 | 9/2014 | Fain |
| 2016/0008612 A1 | 1/2016 | Régnier |
| 2016/0193459 A1 | 7/2016 | Gaudiani |
| 2016/0228712 A1 | 8/2016 | Koop |
| 2016/0279423 A1 | 9/2016 | Kelly et al. |
| 2018/0264274 A1 | 9/2018 | Haasl et al. |
| 2019/0083800 A1 | 3/2019 | Yang et al. |
| 2020/0101279 A1 | 4/2020 | Drake et al. |

OTHER PUBLICATIONS

InSync Sentry and InSync Maximo. Available at: www.medtronic. com . Accessed on Jan. 8, 2008.
PCT/US2007/080160 International Search Report and Written Opinion dated Jan. 29, 2008.
U.S. Appl. No. 11/770,371 Office Action dated Apr. 21, 2011.
U.S. Appl. No. 11/770,371 Office Action dated Jul. 8, 2010.
U.S. Appl. No. 13/278,089 Office Action dated Mar. 27, 2013.
U.S. Appl. No. 14/155,284 Office Action dated Apr. 3, 2015.
U.S. Appl. No. 14/996,631 Office Action dated Apr. 5, 2017.
U.S. Appl. No. 14/996,631 Office Action dated Aug. 27, 2018.

(56) References Cited

OTHER PUBLICATIONS

U.S. Appl. No. 14/996,631 Office Action dated Sep. 20, 2017.
U.S. Appl. No. 16/593,061 Office Action dated Mar. 31, 2022.
U.S. Appl. No. 16/593,061 Office Action dated Nov. 24, 2021.
U.S. Appl. No. 18/147,601 Office Action dated Apr. 5, 2024.
U.S. Appl. No. 18/147,601 Office Action dated Jul. 18, 2023.
U.S. Appl. No. 18/147,601 Office Action dated Oct. 27, 2023.
U.S. Appl. No. 18/295,368 Office Action dated Jul. 20, 2023.
U.S. Appl. No. 14/996,631 Office Action dated May 2, 2018.

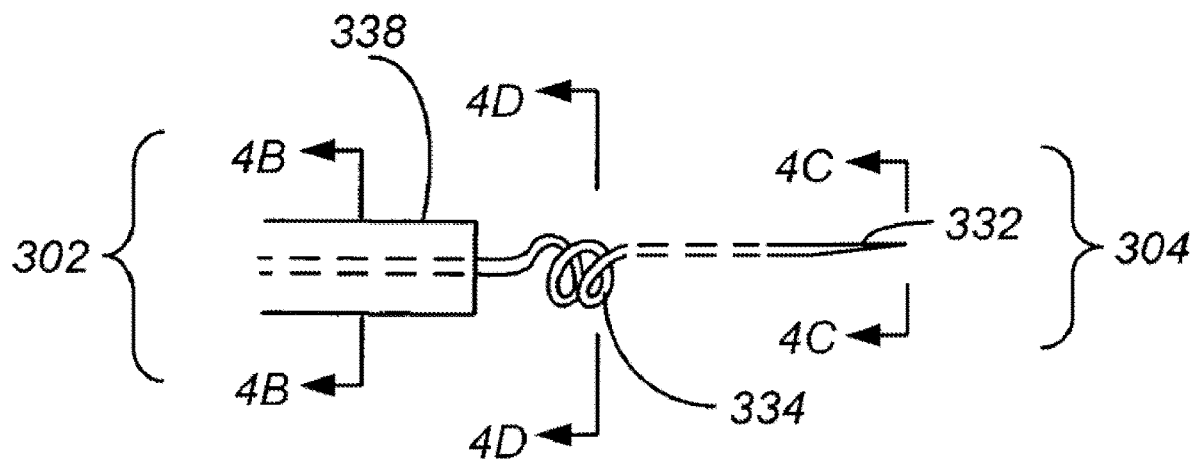
*FIG. 4A*
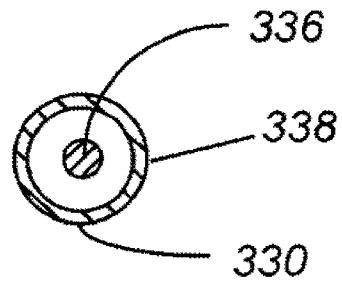
*FIG. 4B*
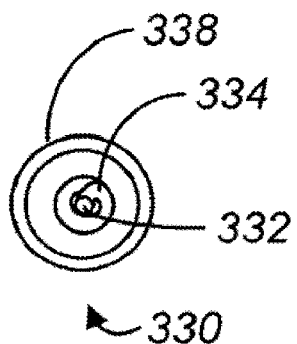 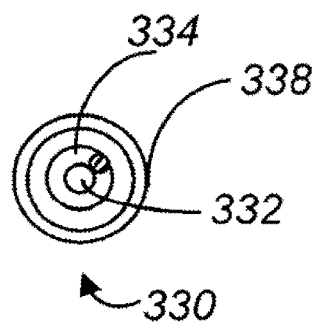
*FIG. 4C* *FIG. 4D*

TRANSCORONARY SINUS PACING OF POSTEROSEPTAL LEFT VENTRICULAR BASE

CROSS-REFERENCE

This application is a continuation of U.S. application Ser. No. 18/295,368, filed Apr. 4, 2023, which is a continuation of U.S. application Ser. No. 16/806,356, filed Mar. 2, 2020, now U.S. Pat. No. 11,648,397, which is a continuation-in-part of U.S. application Ser. No. 16/593,061, filed Oct. 4, 2019, now U.S. Pat. No. 11,577,075, which claims the benefit of U.S. Provisional Patent Application No. 62/744,833, filed Oct. 12, 2018, and U.S. Provisional Patent Application No. 62/897,724, filed Sep. 9, 2019, each of which is entirely incorporated herein by reference.

The subject matter of this application is related to the subject matter of U.S. Pat. Nos. 8,068,920, 8,634,935, and 9,265,938 and U.S. patent application Ser. No. 14/155,284, by Vincent A. Gaudiani, entitled "Transcoronary Sinus Pacing System, LV Summit Pacing, Early Mitral Closure Pacing, and Methods Therefor," the full disclosures of which are entirely incorporated herein by reference.

BACKGROUND

An impairment of the patient's conduction system can prevent the transmission of electrical impulses that allow the heart to depolarize. The depolarization process leads to contraction in the cardiac muscle and a beat of the heart. Ventricular pacing has been a useful technique for at least 60 years, and transvenous pacing for nearly that long. In a transvenous pacing system, referring for example to FIGS. 1A-1D, the lead is placed from a vein, usually in the thorax, and threaded into the right ventricle 22 of the heart 10. The lead in the right ventricle 22 then permits pacing and sensing within that chamber. However, pacing from the right ventricle 22 depolarizes the heart in a completely different way than the heart is normally depolarized and does not make use of the patient's own, usually diseased, conduction system. While ventricular pacing may be very effective in preventing deaths from such entities as complete heart block, there are several problems associated with it. For example, right ventricular pacing can reduce left ventricle function. In some instances, the pacing of the right ventricle can delay activation of the left ventricle and therefore prolong QRS duration, which can cause a more dysynchronous left ventricle contraction. Further, right ventricular pacing can delay closure of the mitral valve, which otherwise closes early in systole during a normal contraction, and this can encourage mitral regurgitation. Patients may also experience pacemaker syndrome, which is a hemodynamic abnormality that can result when use of ventricular pacing is, for example, uncoupled from the atrial contraction. The syndrome can also result from a less effective contraction caused by the abnormal depolarization mechanism caused by the right ventricular pacing catheter. That is, the heart, depolarized from the right ventricular apex, does not squeeze as efficiently as the heart would have squeezed if it had been depolarized by its own conduction mechanism. Patients can sense the decline in cardiac output when their pacemaker activates. In other patients, pacing can induce a long term malfunction of the heart, referred to as cardiomyopathy, which is caused by slower depolarization of the heart and the associated decline in pump efficiency. Furthermore, because the right ventricle pacing catheter crosses the tricuspid valve, this may lead to tricuspid regurgitation.

Over the past one or two decades, first Medtronic and then other companies have developed devices to counter the deleterious effects of ordinary right ventricular apex pacing, such as devices using two different pacing catheters in different parts of the ventricles 22, 26 to simultaneously depolarize the heart. This is referred to herein as biventricular (or biV) pacing. As opposed to pacing only the right ventricle 22, biventricular pacing (also referred to as cardiac resynchronization therapy (CRT)) uses leads that stimulate both the right ventricle 22 from the apex and the left ventricle 26 from the lateral wall via the coronary sinus. One of the electrodes is the standard right ventricular apical pacing catheter and the other is a left ventricular lead which is usually placed, as indicated above, on the posterior left ventricular wall through a vein branch 82 of the coronary sinus 80. When these two leads are coupled together to the same generator and simultaneously stimulate the ventricle, it takes less time to depolarize the ventricle and therefore a more synchronous contraction of the muscle ensues. Hence, the heart can pump blood more efficiently.

Biventricular pacing can also be provided for patients with congestive heart failure (CHF) due to left ventricular dysfunction. It is estimated that in approximately 30% of patients with heart failure, an abnormality in the heart's electrical conducting system causes the heart to beat in an asynchronous fashion (i.e., the left ventricle fails to contract toward its theoretical center of mass). This asynchrony greatly reduces the efficiency of the heart in some patients with heart failure. Biventricular pacing can resynchronize the contraction of the heart by shortening the actuation time of the ventricles. Biventricular pacing systems (BVPS), as they are currently constituted, require an operator to thread a catheter from an introducer in the coronary sinus 80 down into a vein branch 82 of the coronary sinus 80, shown in FIG. 1B, and then wedge that lead into the branch 82 to hold it in position. This technique has been useful but has had some difficulty associated with it. Additionally, one of the risks associated with placement of the device is the potential to damage the coronary sinus or coronary veins by, e.g., dissection or perforation.

Biventricular pacing has now demonstrated utility in several situations. For example, it can reverse the symptoms in patients with the pacemaker syndrome described above. It can also improve many cardiomyopathies caused by long term pacing. In addition, it can improve cardiac contraction in some patients who have enlarged ventricles 22, 26 and prolonged QRS duration who are suffering from heart failure. It has been sufficiently useful so that it is now included in many of the latest models of internal cardioverters and defibrillators (ICD) which are used to treat patients with heart failure and arrhythmia. See, for example, InSync Sentry™ and InSync Maximo™ (www.medtronic.com). Biventricular pacing is now a standard part of the armamentarium and medical science accepts that biventricular pacing, because it leads to more synchronous contraction, is a better way to pace patients than pacing from the right ventricular apex alone. A conventional implantable medical device, such as an ICD, is coupled to a patient's heart by leads such that the patient's heart forms part of the circuit. The device may include, for example, a pacemaker or defibrillator or any device that performs pacing or defibrillating functions. A housing can house a battery and pacing or defibrillating circuitry. Each lead can be adapted to engage at least one stimulating electrode for delivery of electrical impulses to excitable myocardial tissue. The leads can be unipolar or bipolar.

Notwithstanding the clinical benefits of biventricular pacing, correctly placing the left ventricular (LV) lead to achieve optimum performance may be difficult. The placement of the first lead, the lead that goes in the right ventricle 22, has been standard for fifty years. When biventricular pacing was first tried, the placement of the second left ventricular lead was done surgically. However, the surgical procedure requires a small incision in the chest, and most cardiologists cannot do this and do not want to refer patients to surgeons. Therefore, the standard cardiologic technique for LV lead placement now requires placement of a sheath from the subclavian vein into the coronary sinus 80 and through that sheath, an angiogram of the coronary sinus 80 can be obtained. From the angiogram, the branches 82 of the coronary sinus 80 can be identified and a small pacing catheter is then directed through the coronary sinus and into the small coronary sinus vein 82 (see FIG. 1B) where it is lodged. The guiding catheter is then removed, and the patient has a lead on the posterior left ventricular wall. The exact location of the lead is therefore confined to the accidental anatomy of the veins that feed into the coronary sinus 80. The optimal location of the left ventricular lead and solutions for routine pacing from this location have not previously been discussed.

SUMMARY

The concept of electrically stimulating the heart to cause it to contract has been understood since the 1930's, and clinical cardiac pacing began in the 1960's. A convenient way to pace the human heart is to introduce a pacing catheter into a large thoracic vein and fluoroscopically guide it to the right ventricular (RV) apex. This provides a stable position and permits the pacing device to be attached to the pacing catheter and placed under a clavicle. This advance has saved the lives of patients whose intrinsic conduction system has failed (e.g., complete heart block), and improved the lives of those whose conduction system malfunctions (e.g., sick sinus syndrome). Important as it has been, RV apex pacing causes significant clinical problems, and physicians have only begun to address these in the past decade or so. This patent application proposes concepts and devices that will improve physicians' capacity to serve patients with cardiac electrical abnormalities.

Summarized herein are clinical problems caused by RV apex pacing, the improvements achieved with biventricular pacing and its current limitations, and finally the ideas that form the basis of this patent application.

The left ventricle does five times the work of the right ventricle because arterial pressure is at least five times as high as the pressure in the pulmonary circuit. Therefore, the exact mechanism of activating the left ventricle is very important. The intrinsic conduction system activates the left ventricle so that its walls move in, synchronously optimizing the ejection of blood from that activation. Dyssynchronous activation reduces efficient ejection, and if the dyssynchrony is severe enough or if an element of dysynchrony is combined with an element of left ventricular dysfunction from another cause, the patient will experience symptoms of inadequate blood flow. These may range from dizziness or dyspnea with exercise to cardiogenic shock. When the heart is activated from the right ventricular apex, the resulting contraction is always dysynchronous to some degree. The dysynchrony is identical with that caused by left bundle branch block (LBBB). The intrinsic conduction system extends itself into both the right and left ventricle. When the left branch fails from disease or aging, the right bundle activates the RV normally, but electrical activation of the left ventricle proceeds more slowly. This prolonged activation of the left ventricle is exactly what occurs in RV apex pacing, and, in both cases, slower activation reduces synchronous LV contraction.

Although many patients tolerate this problem, it is sufficiently severe to negate the effect of atrioventricular synchrony. The intrinsic conduction system sequentially activates the atria and then the ventricles for each contraction. After developing RV apex pacing, industry developed sequential pacing in the atria and ventricles to mimic the intrinsic conduction system. This was done with separate catheters in the right atrium and right ventricle connected to a pacing device that could mimic the natural system. In several major randomized trials, this "improvement" showed no benefit to patients. It was later shown that the natural advantage of AV synchronous pacing was neutralized by the deleterious effects of RV apex activation.

While life-saving, RV apex pacing inherently diminishes LV function in two ways. First, it causes a slower dyssynchronous contraction as described, and second, it delays closure of the mitral valve. This occurs because the mitral valve is physically far away from the RV apex so the muscle that supports its closure is activated much later in both LBBB and RV apex pacing than it is in a natural depolarization. When the mitral valve closes late, the early part of ventricular systole causes blood to regurgitate back across the valve into the left atrium. The resulting decreased LV volume reduces the effect of Starling's Law: increased filling causes increased contractility and decreased filling causes decreased contractility. A normal heart tolerates these negative effects of pacing fairly well, and when it doesn't and the patient experiences dyspnea, the condition is called pacemaker syndrome.

The effect of RV apex pacing in larger hypocontractile hearts is much worse. The incidence of overt heart failure doubles compared to similar hearts that do not need pacing. This led to the development of biventricular pacing. In this technique, the ventricles are paced simultaneously by two pacing catheters, one attached to the RV apex and the other attached to the left ventricle, so called biventricular pacing (BiV). The key technical problems in this technique are how to attach a lead to the LV and where to locate it. It can be attached surgically during an operation, but cardiologists have desired and developed a technique they could perform. In such techniques, a smaller pacing electrode is passed through the right atrium into the coronary sinus and down into a ventricular vein that drains into the coronary sinus. Simultaneous activation of both ventricles decreased total activation time and therefore improved synchrony. The amount of improvement depends upon how far apart the electrodes are placed. They are farthest apart and optimal when the RV lead is in the apex and the LV electrode is near the posterior summit of the LV, that is, near the mitral valve. Such a location of the LV electrode also facilitates early closure of the mitral valve. This electrode arrangement reduces heart failure, and it is now the standard for pacing those with poor ventricular function.

The major problem with BiV pacing is placing the LV catheter. A pacing electrode in the coronary sinus itself does not pace the LV. Despite how close the coronary sinus is to the LV summit, the sinus itself and the tissue around it insulate the electrode, preventing ventricular activation. The cardiologist is dependent on the location of coronary veins that feed into the coronary sinus, and the operator is wise to choose a longer coronary sinus vein to improve electrode stability and to reduce the likelihood that the catheter will slip back. However, the farther down the ventricle the vein proceeds, the closer it gets to the apex of the heart and hence to the RV apex lead. This reduces the efficacy of BiV pacing.

To address at least the abovementioned problems, provided herein are systems, methods, devices, and equipment for perforating the coronary sinus with a pacing catheter that is then screwed into the summit of the left ventricle to optimize BiV pacing. Provided herein are systems, methods, devices, and equipment that can extend such techniques.

Recognized herein are two central concepts that may improve the outcomes for patients with electrophysiological (EP) cardiac disorders. The first is that LV pacing alone supports many of the advantages of BiV pacing, particularly if the pacing catheter is fixed near the summit of the LV. This is probably because early mitral valve closure is critical to proper LV function. Therefore, this disclosure extends the concept of transcoronary sinus pacing of the LV summit to use as a single catheter to pace the LV. This disclosure envisages the replacement of RV apex pacing by transcoronary sinus pacing. This effectively ends the disadvantages of RV apex pacing. It reduces the volume of foreign material in the central circulation because a transcoronary pacing catheter may be fabricated so that side electrodes can be built into it where it caroms off the right atrial wall. The right atrium and the left ventricular summit can be paced with a single catheter, permitting AV synchrony without two separate pacing catheters. All current ventricular pacing systems cross the tricuspid valve. The catheter described herein can pace the LV summit and the right atrium without crossing the tricuspid valve. This will prevent the inherent risks of catheter induced tricuspid regurgitation inherent in current systems.

The second concept that may improve outcomes for patients with EP disorders is the concept of pacing in or near the Bundle of His. This structure sits about 1 centimeter (cm) below and to the left of the opening of the coronary sinus opening and near the LV summit. It marks the beginning of the natural system that delivers electrical energy to both ventricles. Pacing from this location mimics normal depolarization. This disclosure provides the concept of pacing in or near the His bundle by the transcoronary sinus route and for the equipment used to achieve this. The disclosure provides "leadless" pacing devices that achieves the same.

Recognized herein is a need for more effective, efficient, and predictable lead placement for biventricular pacing systems (BVPS) and other cardiac pacing systems. BVPS, as currently constituted, require an operator to thread a catheter from an introducer sheath in the coronary sinus down into a vein branch of the coronary sinus, as shown in FIG. 1C, and then wedge a lead into the vein branch to hold the lead in position. This technique has been useful but has had some difficulty associated with it.

An aspect of the invention is directed to systems and methods that permit an operator to place a pacing catheter or electrode lead at a target location near the bundle of His (also referred to as the His bundle) and above the septum separating the left and right ventricles, near the orifice of the coronary sinus. Such target location near the His bundle has been identified herein as an effective location for initiating stimulation of the heart. Referring to FIG. 1A, the His bundle 44 is a collection of heart muscle cells located at the base of the ventricles 22, 26 and part of the electrical conduction system of the heart, which facilitates transmission of electrical impulses from the atrioventricular (AV) node 42 to the point of the apex of the fascicular branches via the bundle branches. Beneficially, stimulating a pacing lead placed near the His bundle may stimulate the actual pathways of the heart's electrical conduction system and emulate the normal depolarization mechanism of the heart (as opposed to emulating the final result of depolarization). Placement near the His bundle may also optimize early closure of the mitral valve in addition to reducing the time that it takes to activate the ventricle.

Another aspect of the invention is directed to systems and methods that permit a single pacing catheter to pace both the right atrial wall and left ventricular summit. The coronary sinus opens into the right atrium, but its opening is disposed above and within a few millimeters of the left ventricular summit, and not the right. A pacing catheter may be placed in the heart by guiding it down the right atrium, through an opening of the coronary sinus, perforating a wall of the coronary sinus and passing into the summit of the left ventricle. The pacing catheter may comprise one or more side electrodes that are configured to interface with the right atrial wall and permit atrial pacing. The pacing catheter, introduced via a single procedure, may thus achieve pacing of both the right atrial wall and left ventricular summit (RA/LV pacing).

A double lumen sheath that can place and lodge the pacing catheter in the target location (e.g., near the His bundle, perforating through the coronary sinus, etc.) is disclosed. A method for correlating angiographic coronary anatomy with live fluoroscopic pacing catheter placement is provided. Further, a method for using intravascular ultrasound with pacing catheter placement is provided. These methods can help identify the coronary sinus os and additionally prevent damage to a coronary artery.

Aspects of the present disclosure provide methods for pacing a heart of a patient. An exemplary method comprises: introducing a sheath to vasculature of the patient; steering the sheath within a coronary sinus in the heart to lodge a distal end of the sheath to a target location near the bundle of His above a septum separating a left ventricle and a right ventricle of the heart (near the posteroseptal left ventricular base); advancing a pacing lead through a lumen of the sheath to the target location; coupling the pacing lead to cardiac tissue at the target location; removing the sheath; and electrically pacing near the bundle of His using the pacing lead.

In some embodiments, coupling the pacing lead to cardiac tissue at the target location comprises (i) coupling the pacing lead to cardiac tissue at a first location, (ii) activating the pacing lead to generate a first diagnostic result, and (iii) determining whether the pacing lead at the first location is efficacious based on the first diagnostic results.

In some embodiments, coupling the pacing lead to cardiac tissue at the target location further comprises (iv) upon determining the efficacy of the pacing lead at the first location, further anchoring the pacing lead to cardiac tissue at the first location. In some embodiments, the pacing lead comprises, at a distal end, a first anchor and a second anchor, wherein the second anchor is adjacent and distal to the first anchor, wherein step (i) comprises coupling the second anchor to cardiac tissue at the first location in absence of coupling the first anchor to the cardiac tissue at the first location, and step (iv) comprises coupling both the first anchor and the second anchor to cardiac tissue at the second location. In some embodiments, the first anchor comprises a spring and the second anchor comprises a substantially linear needle. In some embodiments, the first anchor and the second anchor comprise first and second segments of a single, continuous anchor structure, respectively.

In some embodiments, coupling the pacing lead to cardiac tissue at the target location further comprises (iv) upon determining that the pacing lead is non-efficacious at the first location, decoupling the pacing lead from the first location, (v) coupling the pacing lead to cardiac tissue at a second location, (vi) activating the pacing lead to generate a second diagnostic result, and (vii) determining an efficacy of the pacing lead at the second location based on the second diagnostic results. In some embodiments, coupling the pacing lead to cardiac tissue at the target location further comprises processing the first diagnostic result and the second diagnostic result to determine the second location as a more efficient pacing location than the first location.

In some embodiments, coupling the pacing lead to cardiac tissue at the target location) further comprises (iv) upon confirming non-efficacy of the first location, decoupling the pacing lead from the first location, (v) repeating (i)-(iv) for other pacing locations until efficacy is confirmed for a nth pacing location, and (vi) further anchoring the pacing lead to cardiac tissue at the nth pacing location.

In some embodiments, the first diagnostic result is provided by an electrocardiogram (ECG) reading.

In some embodiments, the method further comprises obtaining an angiogram; obtaining a live fluoroscopic image; correlating the angiogram with the live fluoroscopic image; and analyzing the correlated images to identify anatomical structures.

In some embodiments, the method further comprises obtaining an angiogram; obtaining a live intravascular ultrasound image; correlating the angiogram with the live intravascular ultrasound image; and analyzing the correlated images to identify anatomical structures.

In some embodiments, the steering comprises using a cross-section shape of the sheath to facilitate steering.

In some embodiments, the target location is within the coronary sinus. In some embodiments, the target location is less than 25 mm from an opening of the coronary sinus.

In some embodiments, the method further comprises electrically activating the bundle of His using the pacing lead to pace the heart.

In some embodiments, the pacing lead comprises a needle. In some embodiments, the pacing lead comprises an anchor. In some embodiments, the pacing lead comprises a substantially coil shape. In some embodiments, the pacing lead comprises a conical coil shape having an apex angle between 0° and 180°. In some embodiments, the pacing lead comprises a substantially straight shape.

In some embodiments, the sheath comprises a teardrop cross-section. In some embodiments, the sheath is steerable by a guidewire. In some embodiments, the sheath comprises one or more radiopaque markers.

Another aspect of the present disclosure provides methods for pacing a heart of a patient. An exemplary method comprises: introducing a sheath to vasculature of the patient; steering the sheath within a coronary sinus in the heart to lodge a distal end of the sheath to a target location proximal to the bundle of His above a septum separating a left ventricle and a right ventricle of the heart; advancing a first pacing lead through a lumen of the sheath to the target location, wherein the first pacing lead is coupled to a cardiac stimulation device; coupling the first pacing lead to cardiac tissue at the target location; coupling a second pacing lead to cardiac tissue at a second target location different from the target location, wherein the second pacing lead is coupled to the cardiac stimulation device removing the sheath; and activating the cardiac stimulation device to deliver signals to the first pacing lead and the second pacing lead.

In some embodiments, the second target location is in a right atrium of the heart. In some embodiments, second target location is in the right ventricle of the heart. In some embodiments, the second target location is in a summit of the left ventricle. In some embodiments, the coupling comprises perforating the coronary sinus with the second pacing lead. In some embodiments, the second target location is in an apex of the left ventricle.

In some embodiments, the method further comprises obtaining an angiogram; obtaining a live fluoroscopic image; correlating the angiogram with the live fluoroscopic image; and analyzing the correlated images to identify anatomical structures.

In some embodiments, the method further comprises obtaining an angiogram; obtaining a live intravascular ultrasound image; correlating the angiogram with the live intravascular ultrasound image; and analyzing the correlated images to identify anatomical structures.

In some embodiments, the steering comprises using a cross-section shape of the sheath to facilitate steering.

In some embodiments, the target location is within the coronary sinus. In some embodiments, the target location is less than 25 mm from an opening of the coronary sinus.

In some embodiments, the method further comprises electrically activating the bundle of His using the pacing lead paces the heart.

In some embodiments, the pacing lead comprises a needle. In some embodiments, the pacing lead comprises an anchor. In some embodiments, the pacing lead comprises a substantially coil shape. In some embodiments, the pacing lead comprises a substantially straight shape.

In some embodiments, the sheath comprises a teardrop cross-section. In some embodiments, the sheath is steerable by a guidewire. In some embodiments, the sheath comprises one or more radiopaque markers.

Another aspect of the present disclosure provides systems for pacing a heart of a patient. An exemplary system comprises: an elongate sheath configured to be at least partially advanced near or to a coronary sinus in the heart, the elongate sheath comprising a proximal end, a distal end, and a lumen sized and dimensioned for advancing a pacing lead through the lumen, wherein a distal end of the sheath is configured to be disposed at a target location proximal to the bundle of His above a septum separating a left ventricle and a right ventricle of the heart; the pacing lead configured to be coupled to the target location; and a cardiac stimulation device electrically coupled to the pacing lead.

In some embodiments, the pacing lead comprises a needle. In some embodiments, the pacing lead comprises an anchor. In some embodiments, the pacing lead comprises a substantially coil shape. In some embodiments, the pacing lead comprises a substantially straight shape.

In some embodiments, the sheath comprises a teardrop cross-section. In some embodiments, the sheath is steerable by a guidewire. In some embodiments, the sheath comprises one or more radiopaque markers.

In some embodiments, the pacing lead when coupled to the target location paces the heart by providing electrical stimulation to the bundle of His.

In some embodiments, the system further a second pacing lead electrically coupled to the cardiac stimulation device and configured to couple to a second target location different from the target location. In some embodiments, the second target location is in a right atrium of the heart. In some embodiments, second target location is in the right ventricle of the heart. In some embodiments, the second target location is in a summit of the left ventricle.

In some embodiments, the electrical stimulation device is an internal cardioverter and defibrillator.

Another aspect of the present disclosure provides systems for pacing in the heart of a patient. An exemplary system comprises: an encasement comprising a proximal end and a distal end, and including therein a cardiac stimulation device and a power source coupled to the cardiac stimulation device; a first electrode protruding from the proximal end of the encasement and electrically coupled to the cardiac stimulation device, wherein the first electrode has a substantially coil structure implanted in a first location in a right ventricle of the heart; and a second electrode protruding from the distal end of the encasement and electrically coupled to the cardiac stimulation device, wherein the second electrode has a substantially straight structure implanted in a second location in a right atrium of the heart.

Another aspect of the present disclosure provides systems for pacing in a heart of a patient. An exemplary system comprises: an encasement comprising a proximal end and a distal end, and including therein a cardiac stimulation device and a power source electrically coupled to the cardiac stimulation device; an electrode protruding from the proximal end of the encasement and electrically coupled to the cardiac stimulation device, wherein the first electrode has a substantially coil structure implanted in a first location in a right ventricle of the heart; and an anchor protruding from the distal end of the encasement implanted in a second location in a right atrium of the heart.

In some embodiments, the system comprises one or more expandable lateral fins disposed on an external surface of the encasement between the proximal end and the distal end. In some embodiments, the one or more expandable lateral fins are configured to stabilize a placement of the encasement relative to the heart.

In some embodiments, the anchor is a second electrode electrically coupled to the cardiac stimulation device. In some embodiments, the second electrode is configured to electrically stimulate the heart from the second location.

In some embodiments, the first electrode is configured to electrically stimulate the heart from the first location.

In some embodiments, the cardiac stimulation device is configured to generate a pacing signal for the heart and the first electrode is configured to convey the pacing signal to the heart from the first location.

In another aspect, provided is a method for pacing a heart of a patient, comprising: (a) introducing a sheath through a right atrium of the patient; (b) steering the sheath within a coronary sinus in the heart to lodge a distal end of the sheath to a target location that is proximal to a left ventricle summit through a wall of the coronary sinus; (c) advancing a pacing catheter through a lumen of the sheath to the target location, wherein the pacing catheter comprises a first electrode and a second electrode protruding from a body of the pacing catheter; (d) coupling (i) the first electrode to cardiac tissue through the wall of the coronary sinus at the target location and (ii) the second electrode to a right atrial wall; (e) removing the sheath; and electrically pacing the left ventricle summit and the right atrial wall using the pacing catheter.

In some embodiments, the method further comprises obtaining an angiogram; obtaining a live fluoroscopic image; correlating the angiogram with the live fluoroscopic image; and analyzing the correlated images to identify anatomical structures.

In some embodiments, the method further comprises obtaining an angiogram; obtaining a live intravascular ultrasound image; correlating the angiogram with the live intravascular ultrasound image; and analyzing the correlated images to identify anatomical structures.

In some embodiments, (b) comprises using a cross-section shape of the sheath to facilitate steering.

In some embodiments, the target location is within the coronary sinus.

In some embodiments, the target location is less than 25 mm from an opening of the coronary sinus.

In some embodiments, the first electrode comprises a needle.

In some embodiments, the first electrode comprises a substantially coil shape.

In some embodiments, the first electrode comprises a substantially straight shape.

In some embodiments, the second electrode protrudes from a lateral surface of the body of the pacing catheter.

In some embodiments, the body of the pacing catheter further comprises an anchor protruding therefrom. In some embodiments, the anchor comprises a coil or spring.

In some embodiments, the sheath comprises a teardrop cross-section.

In some embodiments, the sheath is steerable by a guidewire.

In some embodiments, the sheath comprises one or more radiopaque markers.

In another aspect, provided is a system for pacing a heart of a patient, comprising: an elongate sheath configured to be at least partially advanced to a coronary sinus in the heart, the elongate sheath comprising a proximal end, a distal end, and a lumen sized and dimensioned for advancing a pacing catheter through the lumen, wherein a distal end of the sheath is configured to be disposed at a target location proximal to a left ventricle summit through a wall of the coronary sinus; the pacing catheter, wherein the pacing catheter comprises a body, a first electrode protruding from the body, and a second electrode protruding from a lateral surface of the body, wherein the first electrode is configured to anchor to cardiac tissue through the wall of the coronary sinus at the target location, and wherein the second electrode is configured to anchor to an atrial wall; and a cardiac stimulation device electrically coupled to the pacing catheter.

In some embodiments, the pacing catheter comprises a third electrode protruding from the lateral surface of the body.

In some embodiments, the pacing catheter comprises an anchor protruding from the body, wherein the anchor is configured to anchor to cardiac tissue. In some embodiments, the anchor comprises a coil or spring.

In some embodiments, the first electrode comprises a needle.

In some embodiments, the first electrode comprises a substantially coil shape.

In some embodiments, the first electrode comprises a substantially straight shape.

In some embodiments, the elongate sheath comprises a teardrop cross-section.

In some embodiments, the elongate sheath is steerable by a guidewire.

In some embodiments, the elongate sheath comprises one or more radiopaque markers.

In some embodiments, the electrical stimulation device is an internal cardioverter and defibrillator.

In another aspect, provided is a system for pacing in a heart of a patient, comprising: a body comprising a proximal end and a distal end, a lateral surface between the proximal end and the distal end; a first electrode protruding from the proximal end of the body and electrically coupled to a cardiac stimulation device, wherein the first electrode has a substantially coil structure implanted in a left ventricle summit of the heart; a second electrode coupled to the lateral surface of the body and electrically coupled to the cardiac stimulation device, wherein the second electrode interfaces a right atrial wall of the heart; and an anchor protruding from the body.

In some embodiments, the system further comprises a third electrode coupled to the lateral surface of the body and electrically coupled to the cardiac stimulation device, wherein the third electrode interfaces the right atrial wall of the heart.

In another aspect, provided is a system for pacing a heart of a patient, comprising: an elongate sheath configured to be at least partially advanced near or to a coronary sinus in the heart, the elongate sheath comprising a proximal end, a distal end, and a lumen sized and dimensioned for advancing a pacing lead through the lumen, wherein a distal end of the sheath is configured to be disposed at a target location proximal to a bundle of His above a septum separating a left ventricle and a right ventricle of the heart; the pacing lead configured to be coupled to the target location, wherein the pacing lead comprises an anchor system comprising a first anchor and a second anchor adjacent and distal to the first anchor; and a cardiac stimulation device electrically coupled to the pacing lead.

In some embodiments, the second anchor comprises a needle. In some embodiments, the first anchor and the second anchor comprise first and second segments, respectively, of a single, continuous anchor structure. In some embodiments, the first anchor comprises a substantially coil shape. In some embodiments, the first anchor comprises a conical coil shape having an apex angle between 0° and 180°. In some embodiments, the second anchor comprises a substantially straight shape.

In some embodiments, the sheath comprises a teardrop cross-section.

In some embodiments, the sheath is steerable by a guidewire.

In some embodiments, the sheath comprises one or more radiopaque markers.

In some embodiments, the sheath comprises one or more echogenic features.

In some embodiments, the pacing lead when coupled to the target location paces the heart by providing electrical stimulation to the bundle of His.

In some embodiments, the system further comprises a second pacing lead electrically coupled to the cardiac stimulation device and configured to couple to a second target location different from the target location.

In some embodiments, the second target location is in a right atrium of the heart.

In some embodiments, second target location is in the right ventricle of the heart.

In some embodiments, the second target location is in a summit of the left ventricle.

In some embodiments, the electrical stimulation device is an internal cardioverter and defibrillator.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

FIG. 4A illustrates a pacing needle electrode and a pacing catheter;

FIG. 4B illustrates a cross-sectional view of the pacing lead within the pacing catheter of FIG. 4A viewed along line 4B of FIG. 4A;

FIG. 4C illustrates an axial view of a pacing needle within the pacing catheter of FIG. 4A viewing the device proximally from line 4C of FIG. 4A;

FIG. 4D illustrates an axial cross-sectional view of a pacing needle within a pacing catheter viewing the device proximally beginning at line 4D of FIG. 4A;

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are systems and methods that permit an operator to place a pacing catheter or electrode lead at a target location proximal to the bundle of His and above the septum separating the left and right ventricles, near the orifice of the coronary sinus. The location may be at or near the posteroseptal left ventricular base, In some instances, the pacing catheter or electrode lead may be advanced through a lumen of a sheath within a coronary sinus of the heart and coupled to cardiac tissue at the target location. In some instances, the target location may be near the orifice of the coronary sinus but not within the coronary sinus. The sheath can be removed, and the bundle of His may be electrically paced via the pacing catheter or the electrode lead.

Figure 1A:
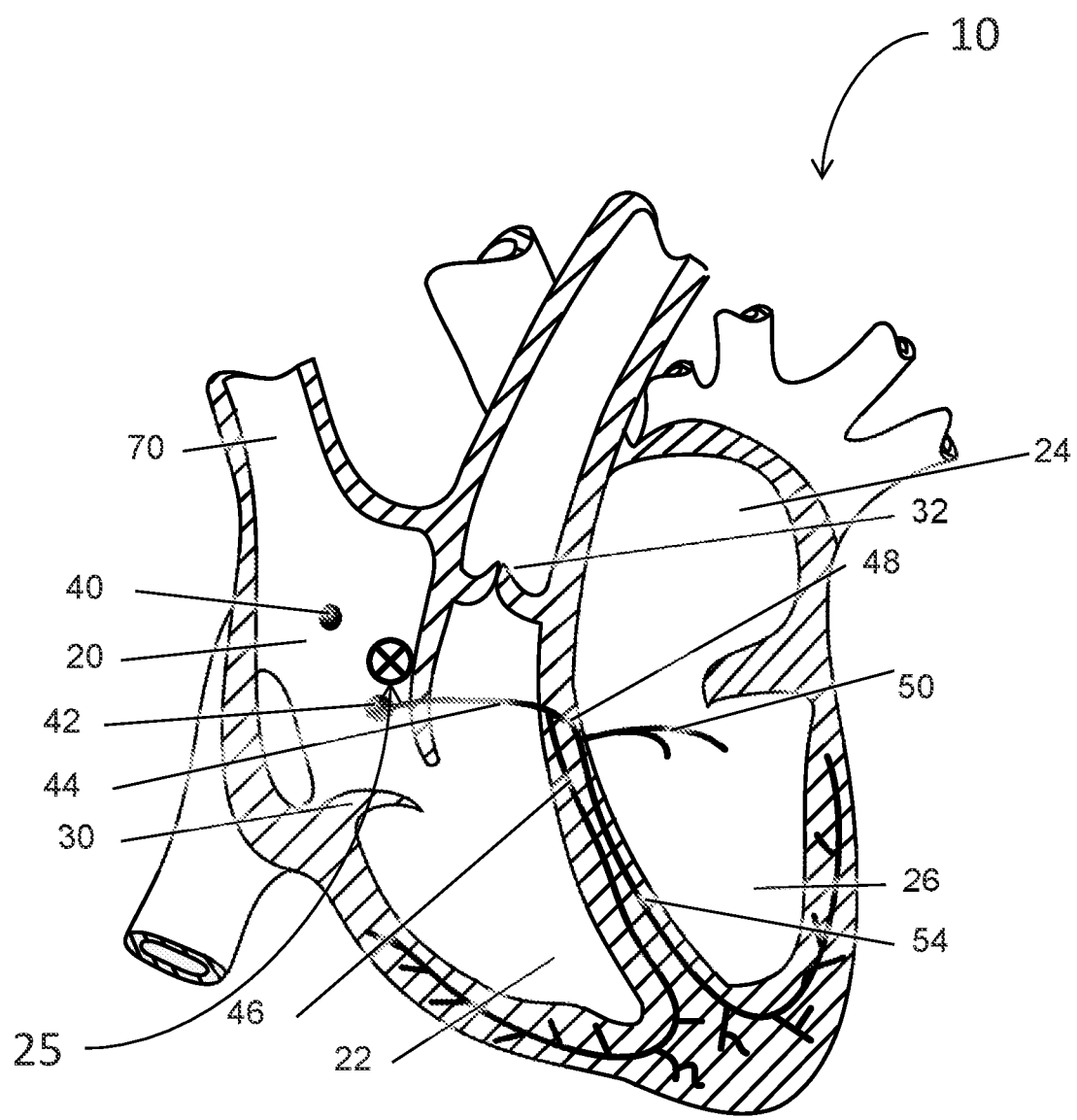
FIG. 1A illustrates a cross-sectional view of the normal ventricular conduction mechanism.

Such target location proximal to the His bundle (e.g., posteroseptal left ventricular base) has been identified herein as an effective location for initiating stimulation of the heart. Referring to FIG. 1A, the His bundle 44 is a collection of heart muscle cells located at the base of the ventricles 22, 26 and part of the electrical conduction system of the heart, which facilitates transmission of electrical impulses from the atrioventricular (AV) node 42 to the point of the apex of the fascicular branches via the bundle branches. Beneficially, stimulating a pacing lead placed near the His bundle may stimulate the actual pathways of the heart's electrical conduction system and emulate the normal depolarization mechanism of the heart (as opposed to emulating the final result of depolarization). Placement near the His bundle may also optimize early closure of the mitral valve in addition to reducing the time that it takes to activate the ventricle.

The systems and methods described herein obviate the need for a separate lead to be placed in a coronary sinus vein 82 for transcoronary sinus pacing systems, as is currently practiced. The systems may rely on the use of a single pacing catheter, which acts as an electrode lead, which is advanced through a guiding catheter to be positioned proximal to the bundle of His 44 above the septum separating the left and right ventricles and near the orifice of the coronary sinus. Once positioned, the pacing catheter is coupled to cardiac tissue. The single pacing catheter, or at least part thereof, may be guided through and within the coronary sinus, such as to perforate a wall of the coronary sinus to pass through to the left ventricular summit 28 (see FIG. 1C).

In order to appreciate the novelty of the invention, it is important to understand the basics of the human conduction system of the heart 10. The normal human conduction system carries an impulse from the atria to the ventricles 22, 26 and distributes the electrical impulse very efficiently so that the entire ventricle is electrically activated in less than 100 milliseconds. This permits effective ventricular contraction. In contrast, right ventricular (RV) apex pacing activates the heart 10 in 150-200 or more milliseconds. This longer time leads to a less synchronous ventricular contraction and often to lower cardiac output and the other complications described above. As used herein, the acronym "RV" may refer to right ventricle or right ventricular. As used herein, the acronym "LV" may refer to left ventricle or left ventricular.

FIG. 1A depicts the normal ventricular conduction mechanism of a heart 10. The normal ventricular conduction mechanism starts with a bridge from the atrium to the ventricles called the atrioventricular node (AV node) 42. The AV node 42 is activated by the sino-atrial node (SA node) 40. Once an impulse passes through the AV node 42, the impulse then passes through the bundle of His 44, which is at the base of the ventricles 22, 26. Thereafter, the conduction system divides into a left main branch 48 and right main branch 46. The left branch 48, which activates the left ventricle 26, almost immediately divides into a small anterior branch 50 and a much larger posterior branch of the left main branch 54 that swings around the left ventricle 26 and basically surrounds the posterior mitral annulus (not shown) before it spreads out over the ventricles 22, 26. This important left posterior branch 54 has not been well understood until recently. The posterior branch 54 activates the left ventricle summit early in systole and starts the process by which the mitral valve 32 closes. The heart 10 as a pump cannot generate much force until the mitral valve 32 is closed and isovolumic systole can begin. At that point, the heart 10 can generate force because the blood inside it is trapped until the pressure inside that chamber exceeds that of aortic pressure at which point the blood is ejected from the ventricle into the aorta. If the summit 28 (see FIG. 1C) of the left ventricle 26 is not activated early, the mitral valve 32 leaks and the heart cannot generate as much force and a lower cardiac output ensues.

Therefore, the optimal position for a left ventricular pacing device, such as the pacing catheter 110, can be at or near the His bundle 44, such as at example location 25 (marked with an "X"), which, upon activation, may navigate the conduction system through left main branch 48 and right main branch 46, and to the left posterior branch 54 to activate the left ventricle 54 to close the mitral valve 32. In an alternative embodiment, a pacing catheter may be placed mid-position on the posterior summit 28 of the left ventricle 26 (the LV summit). In FIG. 1C, an example location for actual left ventricular pacing is marked near the mid-position of the LV summit 28. Alternatively, both a first pacing lead may be placed near the His bundle 44 and a second pacing lead may be placed near the LV summit 28. As will be appreciated by those skilled in the art, the actual location for pacing will vary slightly from patient-to-patient as a function of the individual's coronary anatomy.

Figure 1B:
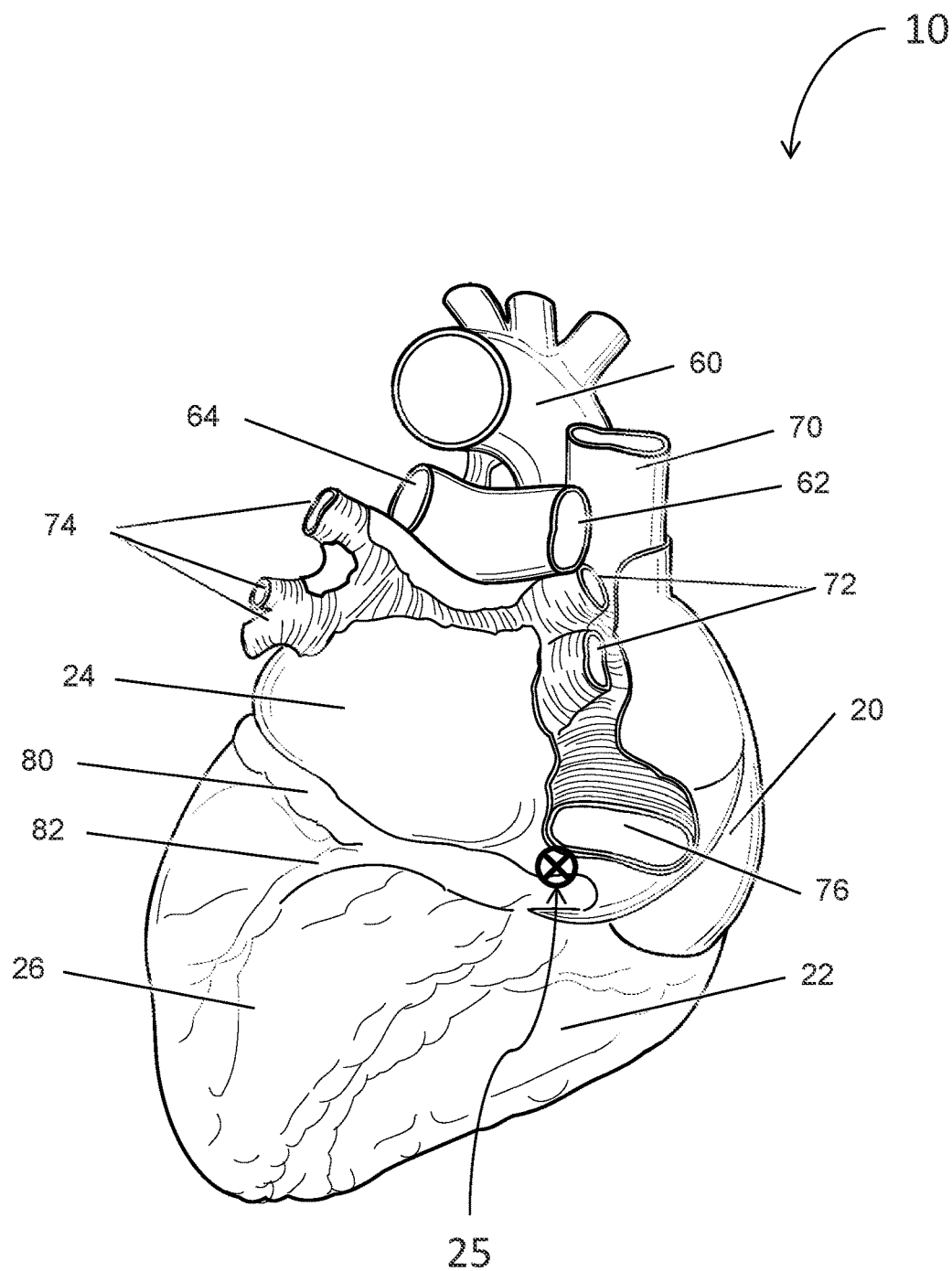
FIG. 1B illustrates a posteroinferior view of the heart.
Figure 1C:
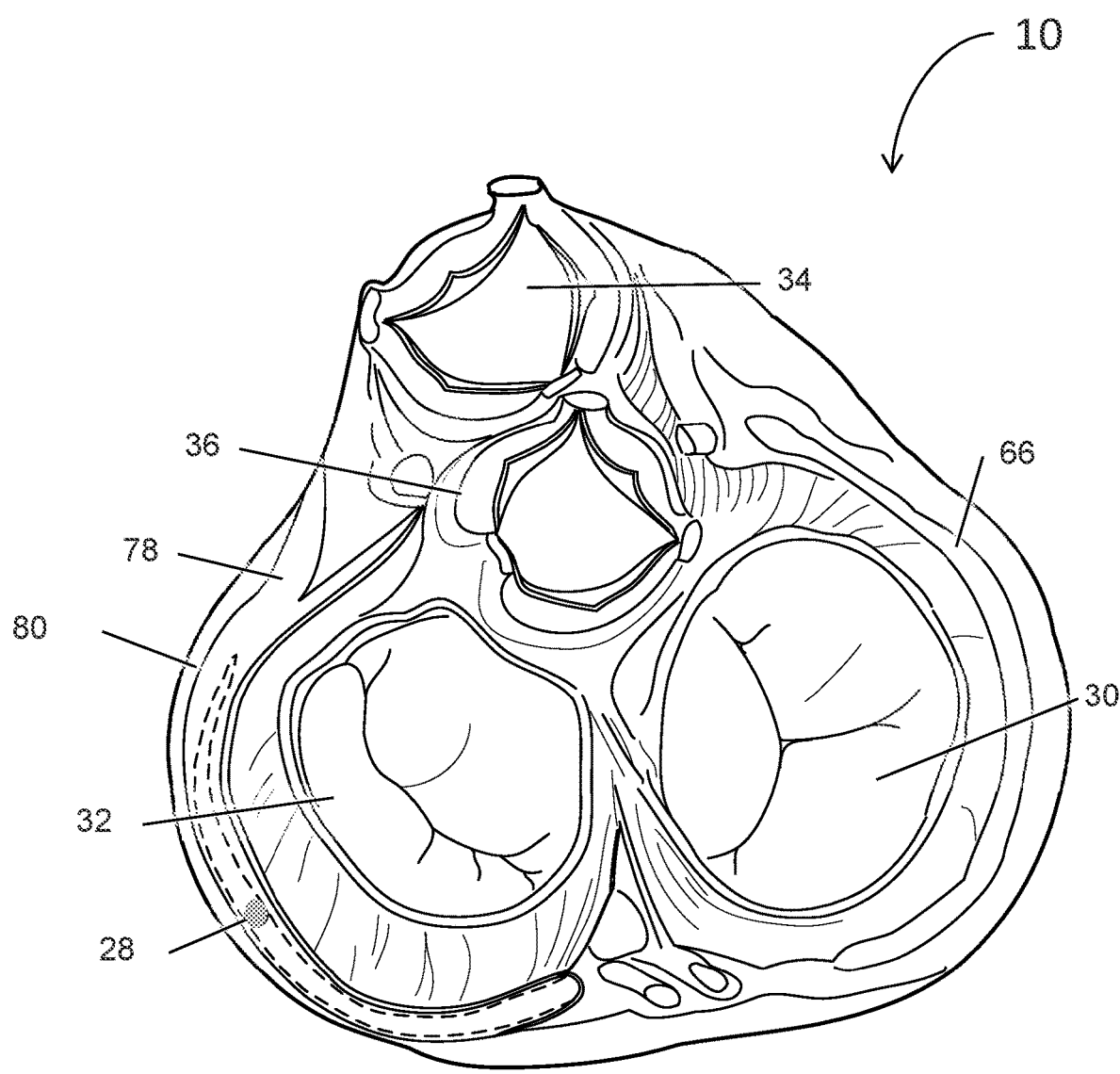
FIG. 1C illustrates a cross-sectional view of heart in systole showing an approximate summit of the left ventricle.

FIG. 1B depicts a posteroinferior view of the heart 10, showing the relative positions of the aortic arch 60, the left pulmonary artery 64, the right pulmonary artery 62, the left pulmonary veins 74, the right pulmonary veins 72, the left atrium 24, the coronary sinus 80, a branch of the coronary sinus 82, the left ventricle 26, the right atrium 20, the right ventricle 22, the superior vena cava 70, and the inferior vena cava 76.

FIG. 1C depicts a cross-sectional view of heart 10 in systole showing the approximate summit 28 of the left ventricle 26. FIG. 1C also shows the relative positions of the aortic valve 36, the pulmonary valve 34, the right coronary artery 66, the mitral valve 32, the tricuspid valve 30, the coronary sinus 80, and the great coronary vein 78, which is a branch 82 of the coronary sinus 80. The circumflex artery (not shown) is generally coincident with or generally near the coronary sinus 80 depicted in FIG. 1C around the mitral valve 32.

Figure 1D:
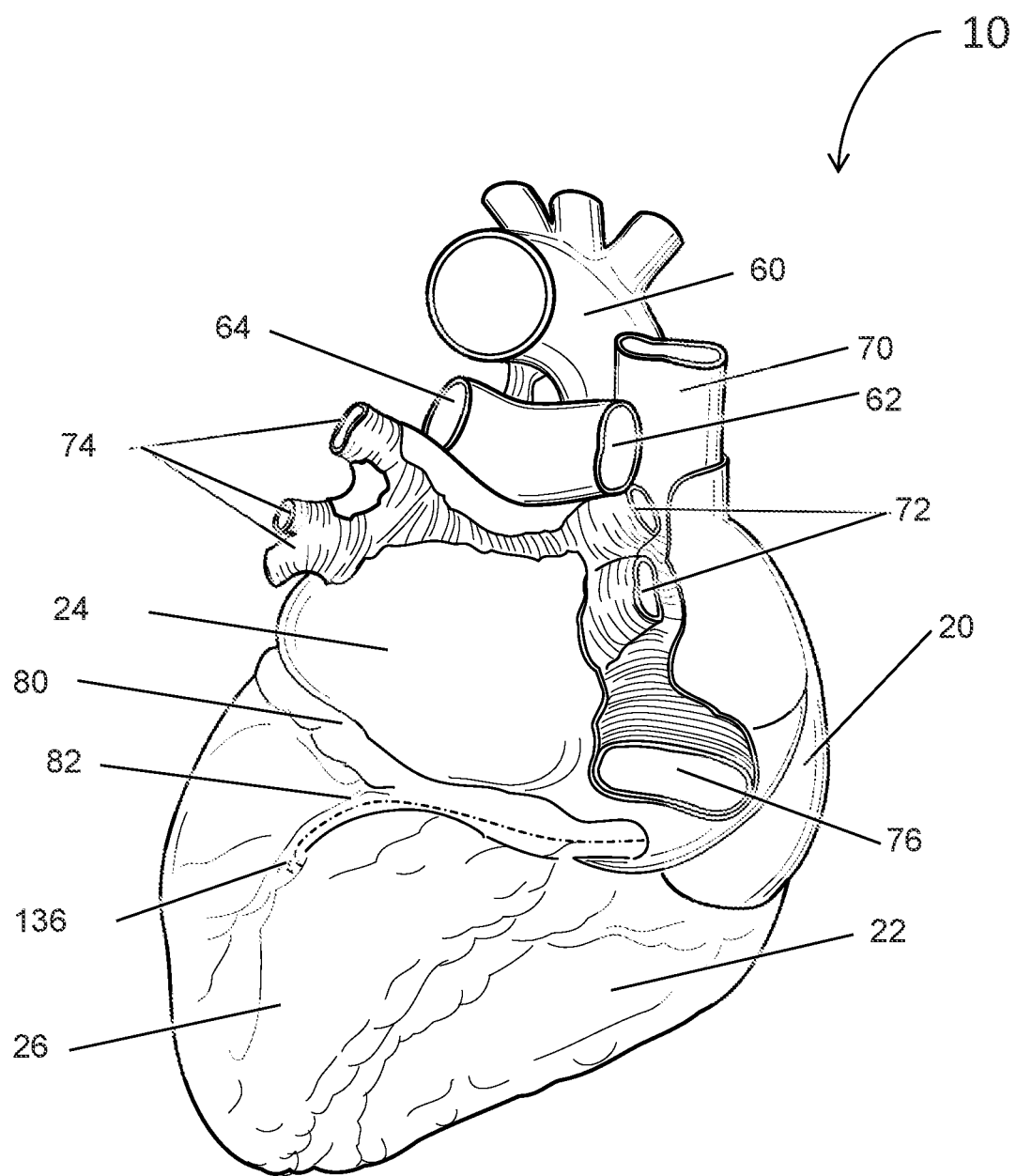
FIG. 1D illustrates a posteroinferior view of the heart showing LV pacing lead placement in a coronary sinus vein.

Currently available systems are confined to the variability of branch veins 82 of the coronary sinus 80. The veins 82 of the coronary sinus 80 can occur anywhere posteriorly and therefore cardiologists are forced to put them wherever they find a vein 82. For example, FIG. 1D depicts a posteroinferior view of the heart showing a LV pacing lead 136 placed in a coronary sinus branch vein 82. FIG. 1D also shows such lead placement and its relative position to aortic arch 60, the left pulmonary artery 64, the right pulmonary artery 62, the left pulmonary veins 74, the right pulmonary veins 72, the left atrium 24, the coronary sinus 80 generally, the left ventricle 26, the right ventricle 22, the superior vena cava 70, and the inferior vena cava 76.

In addition, some patients do not have proper sized veins and so the anatomy of some patients does not permit the placement of a transvenous left ventricular lead in the branch veins 82. Currently the focus has been on another important idea: having the two pacing leads, the one in the right ventricle 22 and the one in the left posterior ventricle 26, as far apart as possible in order to reduce the time that it takes to activate the entire left ventricular mass.

Thus, it is appreciated herein that a target location (e.g., example location 25) proximal to the His bundle 44 is an ideal location for placing a pacing lead. Additionally, this location may be reached without further intrusive advancement into the heart. The location may be reached without crossing the tricuspid valve 30. In some cases, placement at the target location may additionally reduce the amount of time it takes for electrical activity to depolarize the heart. In some instances, a sharp electrode may perforate the coronary sinus 80. Parahisian pacing is also described in U.S. Pat. Nos. 9,579,501; 9,168,382; 9,008,768; 8,812,106; 8,406,899; 8,078,287; 7,647,124; 7,558,631; 7,184,839; 7,177,704; 7,027,876; 6,937,897; and 3,995,623, and U.S. Patent Pub. No. 2012/0232563.

Figure 8A:
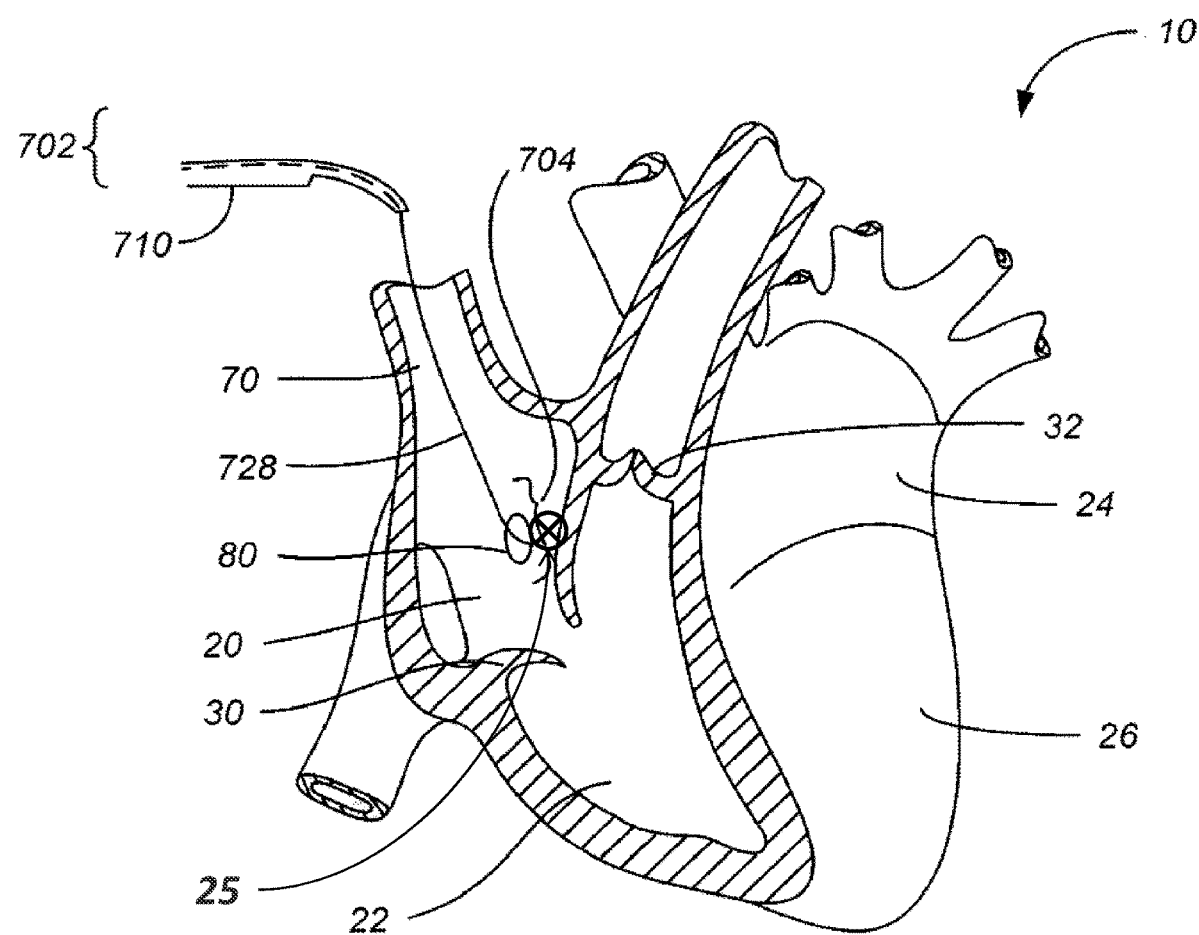
FIG. 8A illustrates a cross-sectional view of a right atrium, a right ventricle, a tricuspid valve, and a pulmonary artery, wherein a guiding catheter is advancing along a guidewire that has been inserted through the superior vena cava, into the right atrium then into coronary sinus.

Also provided herein are systems, devices, and methods that permit a single pacing catheter to pace both the right atrial wall and left ventricular summit. Referring to FIG. 8A, a single pacing catheter may be introduced to an opening of the coronary sinus 80 through the right atrium 20. The coronary sinus 80 opens into the right atrium 20, but its opening is disposed above and within a few millimeters of the left ventricular summit. Upon entry into the coronary sinus 80, one or more leads of the pacing catheter may perforate a wall of the coronary sinus 80 and pass into the left ventricular summit (e.g., 28 in FIG. 1C). For example, the pacing catheter may comprise a screw-in lead that perforates the wall of the coronary sinus. The pacing catheter may comprise one or more side electrodes configured to interface the right atrial wall. Such side electrodes may be attached to a lateral surface of a body of the pacing catheter. In some instances, the pacing catheter may comprise one or more anchors to stabilize its lead placement in the heart.

I. DEVICES

Figure 2A:
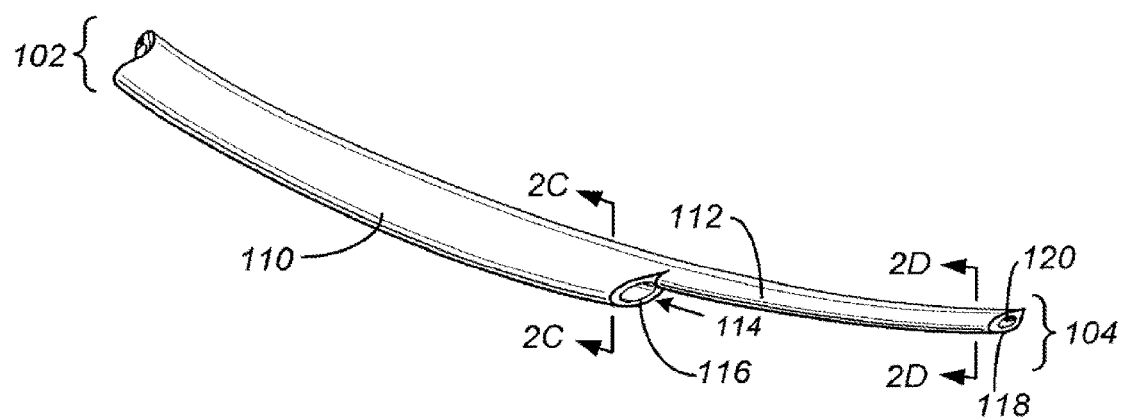
FIG. 2A illustrates an external view of the distal end of a guiding catheter.
Figure 5:
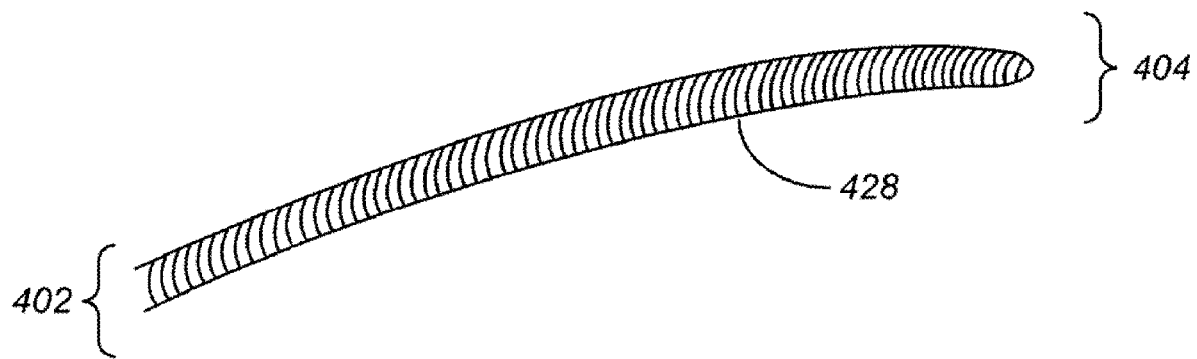
FIG. 5 illustrates a distal end of a guidewire.

FIG. 2A depicts an external view of a distal end of a guiding catheter 110. The guiding catheter 110 is typically a long fine catheter specially designed for passage, usually through a subclavian vein, into the heart under roentgenologic control to provide therapeutic intervention. The guiding catheter 110 can be in the form of a tear-drop cross-sectioned sheath having two lumens 116, 120 each of which has a distal exit port, spaced apart from each other, along the length of the catheter. The first guidewire lumen 120 provides a guidewire exit port 118 at or near the distal end 104 of the catheter from the catheter nose 112. The guidewire entrance port (not shown) is positioned proximally relative to the exit port. As will be appreciated by those skilled in the art, the position of the entrance port can vary according to a particular design and desired functionality. Additionally, the guidewire lumen 120 is configured to enable a guidewire (not shown) to easily pass through its lumen 120 during use. The guidewire facilitates guiding the entire guiding catheter 110 system through the patient's blood vessels to a target region, such as the His bundle 44, the coronary sinus 80 or an orifice thereof. A distal end 404 of the guidewire 440 is shown in FIG. 5. The guidewire may be of a type that is more flexible at its distal end 404 than at its proximal end 402. Additionally, the distal end of the guiding catheter 110 has a nose 112, having a smaller radius than a proximal radius of the guiding catheter 110, that is configured to facilitate positioning the pacing catheter exit port 114 optimally relative to a target location, such as the His bundle or the posterior LV summit. To achieve this, the dimensions of the distal end of the device (where only one lumen is present) may be smaller than a proximal end of the device (where two lumens are present), as appreciated from the cross-sections shown in FIGS. 2C-D.

Figure 7A:
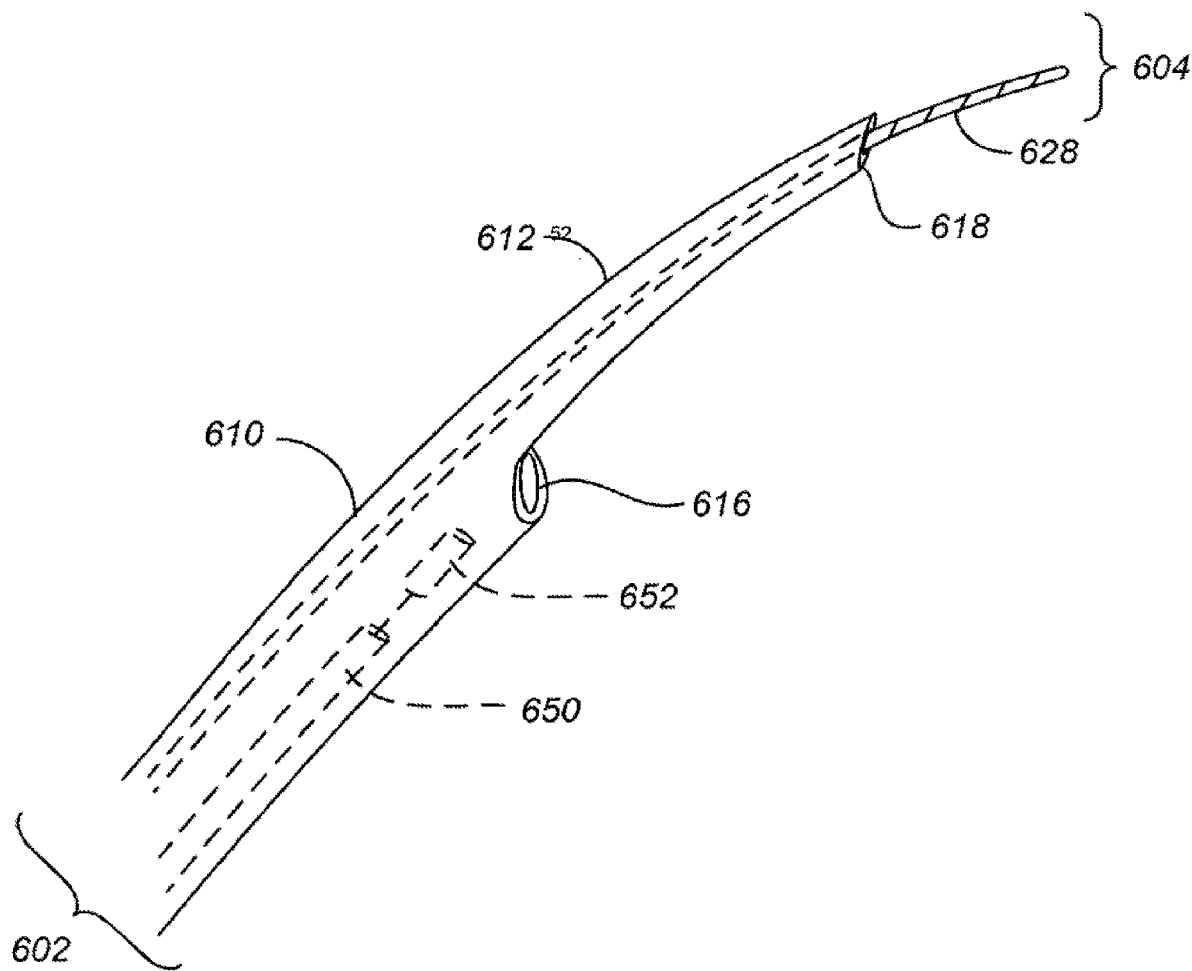
FIG. 7A illustrates an ultrasound assembly system comprising a guiding catheter advanced along guidewire, and an ultrasound catheter within the guiding catheter lumen.
Figure 7B:
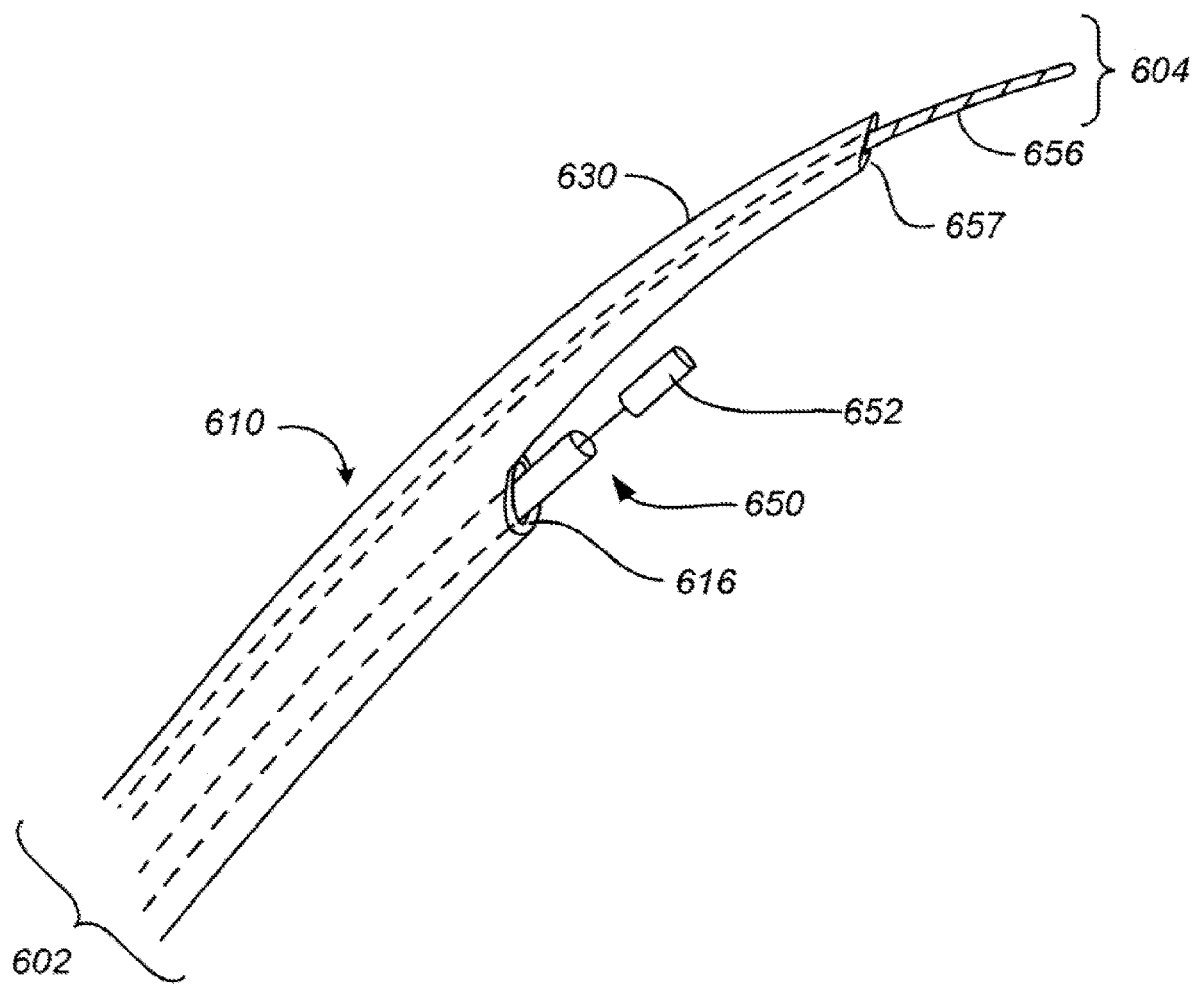
FIG. 7B illustrates a guiding catheter advanced along a guidewire, and showing an ultrasound catheter advanced through the guiding catheter lumen.

The second pacing catheter lumen 116 of the guiding catheter 110, which may be a larger lumen to accommodate various working devices, may be configured to carry the pacing catheter 230, such as that shown in FIG. 3, and is discussed further below. The pacing catheter lumen 116 has a pacing catheter exit port 114 that is positioned along the length of the guiding catheter such that the pacing catheter exit port 114 is positioned near the distal end 104 of the guiding catheter 110 but is proximal relative to the guidewire exit port 118. The pacing catheter lumen 116 may further carry other therapeutic and diagnostic devices, such as an ultrasound catheter 650, as shown in FIGS. 7A-7B, and discussed further below. The pacing catheter lumen 116 may also carry fluoroscopic material to flush the coronary anatomy in order to facilitate vasculature visualization during fluoroscopy and angiography, including visualization of radiopaque markers. Further, the pacing catheter lumen 116 may also carry fluoroscopic material simultaneously with the pacing catheter, such as pacing catheter 230 shown in FIG. 3, or another therapeutic or diagnostic device, such as an ultrasound catheter 650 shown in FIG. 7. The markers assist in allowing the physician to determine which way the catheter is advanced during the procedure.

Figure 2B:
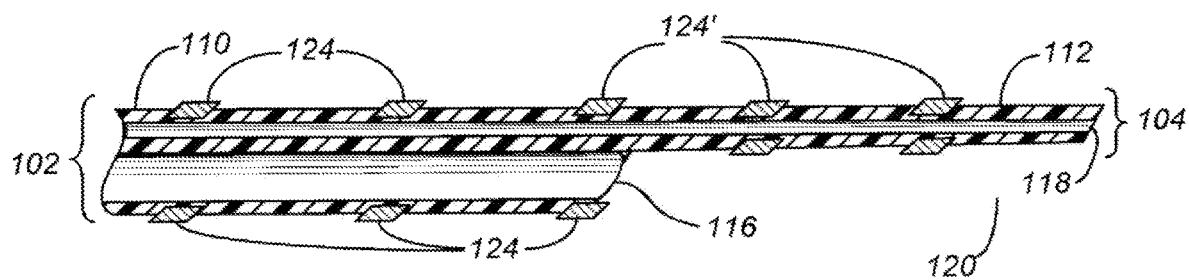
FIG. 2B illustrates a cross-sectional view of the distal end of a guiding catheter along the longitudinal axis and showing radiopaque markers.

FIG. 2B depicts a cross-sectional view of the distal end 104 of a guiding catheter 110 along its longitudinal axis showing radiopaque markers 124, 124'. More or fewer markers may be used to optimally visualize the location of the guiding catheter 110 within the vasculature of the subject, such as within the coronary sinus 80. The radiopaque markers 124 can be positioned in order to visualize the location of the pacing catheter exit port 114 (distally within the coronary sinus 80) as well as its orientation within a patient's vasculature. The radiopaque markers 124 depicted in FIG. 2B can provide fine adjustment before inserting the pacing catheter (shown below). The radiopaque markers 124 allow an operator to orient the guiding catheter 110 and the pacing catheter exit port 114 fluoroscopically, such as with respect to the actual shape of the patient's left ventricle 26. In an example, when the pacing catheter is advanced through the guiding catheter 110 and extends distally out of the pacing catheter exit port 114 it will be positioned to pierce the coronary sinus 80 at the summit 28 of the left ventricle 26 and will not, for example, end up outside the heart 10. The use of such visualization aids the operator in the proper placement of the pacing electrode needle (shown below) and anchor (shown below) at the target location while avoiding perforating a coronary artery or ending up in the pericardium (not shown).

As will be further appreciated, a variety of configurations for the guidewire lumen can be employed without departing from the scope of the invention. For example, the guidewire lumen can be configured to provide a distal exit port 118 at the guiding catheter distal tip 112 or catheter nose as shown in FIG. 2B, and a proximal exit port (not shown) which extends through the guiding catheter 110 only to about the same location along the length of the catheter as the pacing catheter exit port 114. In an alternative configuration, the guidewire lumen and proximal exit port of the guiding catheter 110 may extend farther proximally, or extend the entire length of the catheter as an over-the-wire embodiment. The guiding catheter may also be configured to be stiffer proximally for increased catheter pushability and steerability during use.

Also as illustrated in FIGS. 2A-2B the guiding catheter 110 can comprise a long, flexible nose 112 and a body. This nose 112 provides a stable platform for advancing the pacing catheter (shown below) and for permitting the operator to bend the sheath at the site of the larger pacing catheter lumen 116. The nose 112 permits the operator to bias the pacing catheter exit port 114 toward target location (e.g., 25) before the pacing catheter (shown below) is advanced distally out of the pacing catheter exit port 114.

Figure 2C:
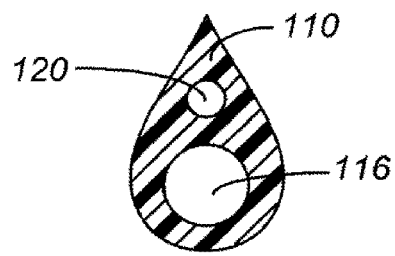
FIG. 2C illustrates an axial view of the distal end of the guiding catheter of the embodiment depicted in FIG. 2A along line 2C of FIG. 2A.

FIG. 2C depicts an axial view from the distal end of the guiding catheter 110 of the guiding catheter shown in FIG. 2A facing proximally along line 2C of FIG. 2A. Also depicted is the pacing catheter lumen 116. As depicted, the cross-sectional shape of the device is teardrop shaped in order to aid operator manipulation the device from the proximal end to visualize, steer, manipulate, and position the guiding catheter 110 at its distal end 104, such as within the coronary sinus 80. The teardrop shape, also depicted in FIG. 2D, additionally helps the user orient the guiding catheter 110 correctly within the coronary sinus 80. As will be appreciated by those skilled in the art, the use of a teardrop shape profile also enables a user to determine at a proximal end the orientation of the distal end of the device, thereby facilitating steering and positioning. Alternatively, the cross-sectional shape may be any other shape.

Figure 2D:
FIG. 2D illustrates an axial view of the distal end of guiding catheter nose along line 2D of FIG. 2A.

FIG. 2D depicts an axial view of distal end of the guiding catheter nose 112 of the embodiment depicted in FIG. 2A facing proximally along line 2D of FIG. 2A. The long nose 112 of the guiding catheter 110 beyond the location of the larger pacing catheter lumen 116 (shown above) is thin and flexible and is designed to lodge the guiding catheter 110 securely in the coronary sinus so that the pacing catheter exiting from the pacing catheter lumen can be securely advanced through the coronary sinus without movement of the guiding catheter 110.

Figure 3:
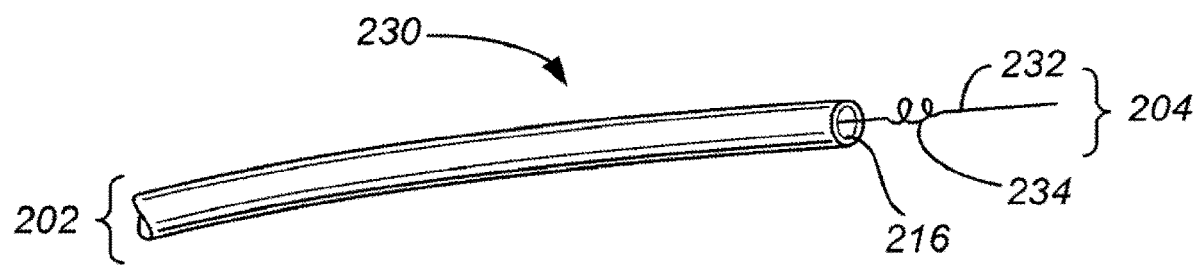
FIG. 3 illustrates an external view of a pacing needle electrode and a pacing catheter.

FIG. 3 depicts an external view of an embodiment of a pacing catheter 230 and a pacing needle electrode 232. This view also shows a pacing needle anchor 234 (pigtail) of an embodiment. The pacing catheter is composed of the needle that perforates cardiac tissue at the target location, for example near the His bundle or in the coronary sinus to enter the LV summit, the screw in device just behind it that anchors the needle within the LV summit, and a pacing wire that extends back to the location of the pacing device usually placed subcutaneously under the clavicle. Once positioned and attached to a control device, such as the ICD, the position of the electrode can reduce the amount of time required to activate the left ventricle.

FIG. 4A also shows pacing catheter 330 needle electrode 332. In this view, the pacing catheter 330 is proximal to the pacing needle anchor 334. The pacing catheter 330 is shown at the distal tip of the device, and the embodiment is shown having an insulated portion 338 beginning at a point proximal to the exposed electrode 332. Insulation of the lead continues proximally from such point to ensure other areas of the heart are not exposed to an electrical signal when the lead 336 is activated. The pacing catheter 330 can be shaped like a standard right ventricular screw-in electrode catheter but instead of having merely a simple corkscrew end there can be a long needle 332 at the distal tip 304 of the pacing catheter 330 which is approximately 1 centimeter long and which extends distally beyond the screw-in anchor portion 334 of the device 330. In alternative embodiments, the pacing catheter can be shaped like a standard right ventricular screw-in electrode having a substantially coil end. In alternative embodiments, the pacing catheter can have a substantially straight end.

Figure 4E:
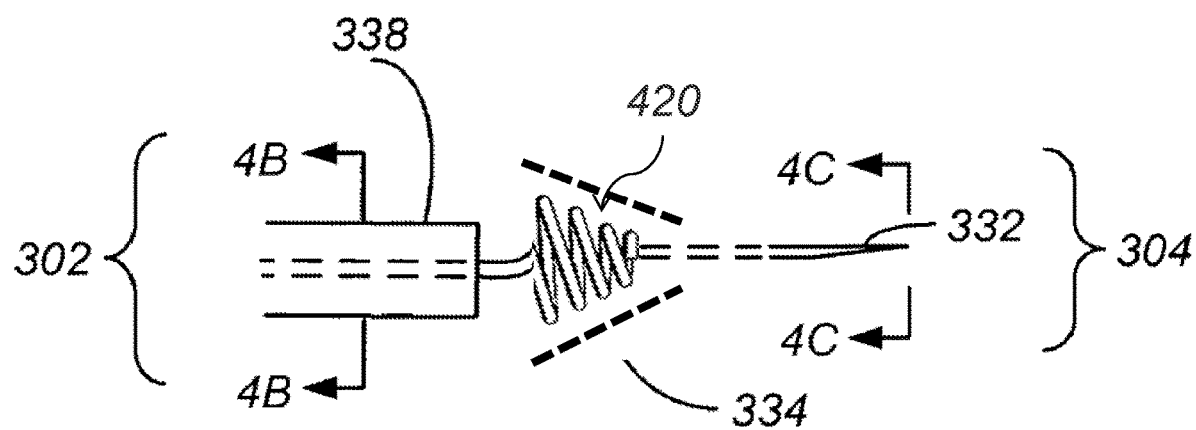
FIG. 4E illustrates another pacing needle electrode and a pacing catheter.

FIG. 4E illustrates another example of a pacing catheter 330 needle electrode 332. In this view, the pacing catheter 330 is proximal to the pacing needle anchor 334. The pacing catheter 330 is shown at the distal tip of the device, and the embodiment is shown having an insulated portion 338 beginning at a point proximal to the exposed electrode 332.

Insulation of the lead continues proximally from such point to ensure other areas of the heart are not exposed to an electrical signal when the lead 336 is activated. The pacing catheter 330 can have a conical screw-in electrode 420 which extends into long needle 332 at the distal tip 304 of the pacing catheter 330 and which extends distally beyond the screw-in anchor portion 334 of the device 330. The conical screw-in electrode 420 can have a larger diameter towards the proximal end and a smaller diameter towards the distal end of the anchor 334. The combination of the conical screw-in electrode 420 and the long needle 332 can function as a single, continuous anchor structure which may be advanced into tissue at different depths into cardiac tissue, for example, a shallow depth for testing the placement of the electrode 420 at the anchoring site, and/or a deeper depth for permanent implantation as further described below.

The linear length of the conical screw-in electrode 420 (from the proximal end to the distal end) can be substantially the same as that of a standard right ventricular screw-in electrode. Alternatively, the linear length of the conical screw-in electrode may be longer or shorter than that of a standard right ventricular screw-in electrode. In alternative embodiments, the pacing catheter can have a substantially coil end (e.g., of the conical screw-in). In alternative embodiments, the pacing catheter can have a substantially straight end. In some instances, the linear length of the screw-in coil (e.g., conical coil, straight coil, etc.) is at least about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm or greater. Alternatively or in addition, the linear length of the screw-in coil is at most about 1.5 mm, 1.4 mm, 1.3 mm, 1.2 mm, 1.1 mm, 1.0 mm, 0.9 mm, 0.8 mm, 0.7 mm, 0.6 mm, 0.5 mm, 0.4 mm, 0.3 mm, 0.2 mm, 0.1 mm or less. The apex angle of the conical screw-in may be any angle between 0° and 180°. The needle tip 332 of the pacing catheter 330 may be any suitable length for purposes of reaching and/or anchoring to target tissue. The needle tip may be any suitable length for purposes of piercing and traversing intermediary tissue. In some instances, the length of the needle tip is about 1 centimeter (cm). In some instances, the length of the needle tip is about 0.6 millimeters (mm). In some examples, the length of the needle tip is at least about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm or greater. Alternatively or in addition, the length of the needle tip is at most about 2.0 mm, 1.9 mm, 1.8 mm, 1.7 mm, 1.6 mm, 1.5 mm, 1.4 mm, 1.3 mm, 1.2 mm, 1.1 mm, 1.0 mm, 0.9 mm, 0.8 mm, 0.7 mm, 0.6 mm, 0.5 mm, 0.4 mm, 0.3 mm, 0.2 mm, 0.1 mm or less.

FIG. 4B shows cross-sectional view of the embodiment depicted in FIG. 4A comprising a pacing lead 336 within a pacing catheter 330 along line 4B of FIG. 4A. FIG. 4c depicts an axial view of the embodiment depicted in FIG. 4A comprising a pacing needle 332 within the insulated portion 338 of the pacing catheter 330 viewing the embodiment proximally from line 4C of FIG. 4A. FIG. 4D depicts an axial cross-sectional view of the embodiment depicted in FIG. 4A comprising a pacing needle electrode 332 within a pacing catheter 330 viewing the embodiment proximally beginning at line 4D of FIG. 4A.

FIG. 5 illustrates a guidewire 428. Suitable guidewire designs are known to a person skilled in the art and include, for example, those described in U.S. Pat. No. 7,089,065 for Modified guidewire for left ventricular access lead; U.S. Pat. No. 6,973,352 for Steerable cardiac pacing and sensing catheter and guidewire for implanting leads; U.S. Pat. No. 6,671,560 for Modified guidewire for left ventricular access lead; U.S. Pat. No. 6,493,591 for Implantable active fixation lead with guidewire tip; U.S. Pat. No. 6,356,791 for Modified guidewire for left ventricular access lead; U.S. Pat. No. 5,549,109 for Sheathed multipolar catheter and multipolar guidewire for sensing cardiac electrical activity; U.S. Pat. No. 5,477,864 for Cardiovascular guidewire of enhanced biocompatibility; U.S. Pat. No. 4,917,102 for Guidewire assembly with steerable adjustable tips.

Figure 6A:
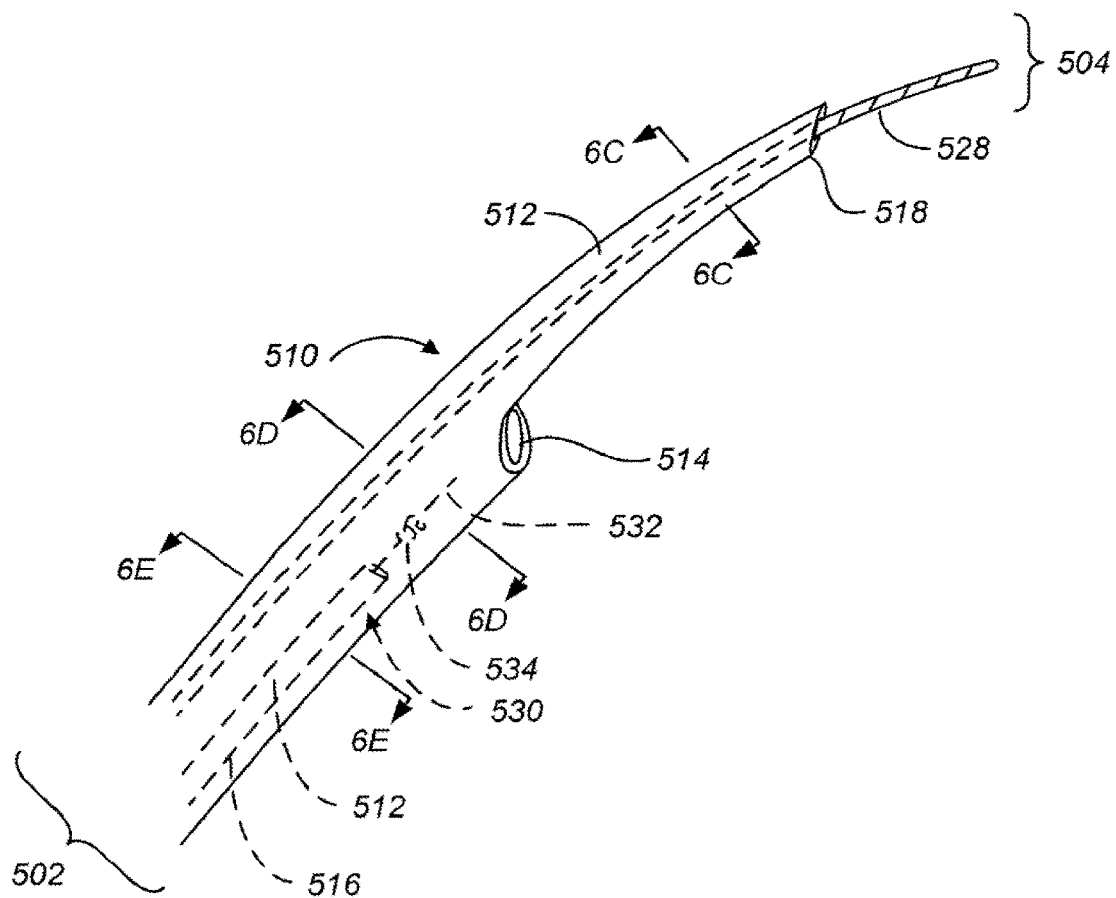
FIG. 6A illustrates a guidewire and a pacing catheter within an elongate sheath of the guiding catheter, with the pacing catheter still within the sheath.
Figure 6B:
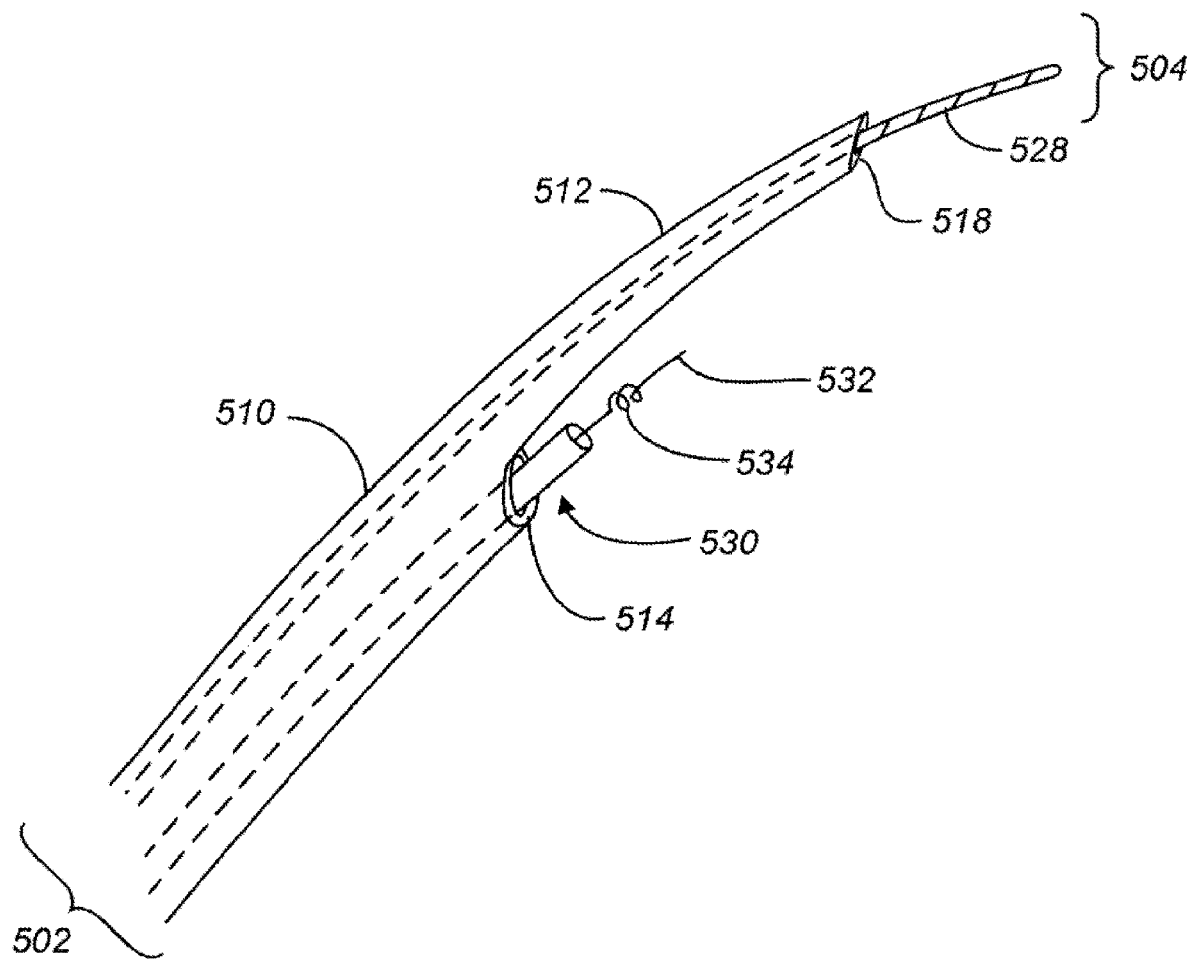
FIG. 6B illustrates a guidewire and a pacing catheter within an elongate sheath of the guiding catheter, with the pacing catheter advanced out the distal end of the sheath.

FIG. 6A shows an embodiment wherein a guidewire 528, an example of which is shown in FIG. 5, and pacing catheter 530 are positioned within lumens of the elongate sheath of the guiding catheter 510. The guiding catheter 510 is shown advanced along the guidewire 528 and the pacing catheter 530, having a pacing needle electrode 532 and a pacing catheter anchor 234, has been advanced within the pacing catheter lumen 516. The pacing catheter 530 is depicted within the pacing catheter lumen 516 of the guiding catheter 510 prior to exiting the pacing catheter exit port 514. In the embodiment depicted in FIG. 6B, the guiding catheter 510 has been advanced along the guidewire 528 and the pacing catheter 530, having a pacing needle electrode 532 and a pacing catheter anchor 534, has been advanced out the distal end of the elongate sheath of the guiding catheter 510. The guiding catheter 510 embodiments of FIG. 6A and FIG. 6B comprise a pacing catheter lumen 516, a pacing catheter exit port 514, a guiding catheter nose 512, a guidewire lumen 520, and a guidewire distal exit port 518.

Figure 6C:
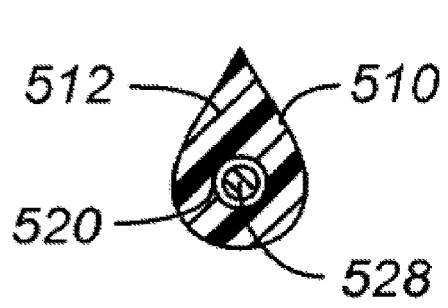
FIG. 6C illustrates a cross-sectional view of a guidewire within the nose of a guiding catheter along line 6C of FIG. 6A.
Figure 6D:
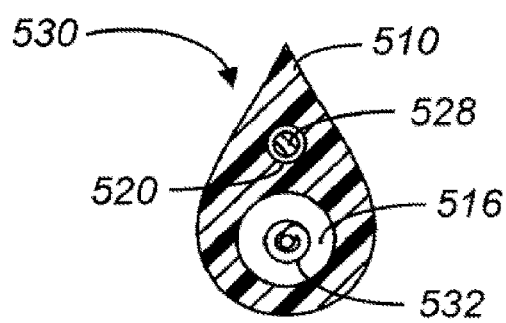
FIG. 6D illustrates an axial cross-sectional view of a pacing needle and a guidewire within the guiding catheter viewing the device proximally from line 6D of FIG. 6A.
Figure 6E:
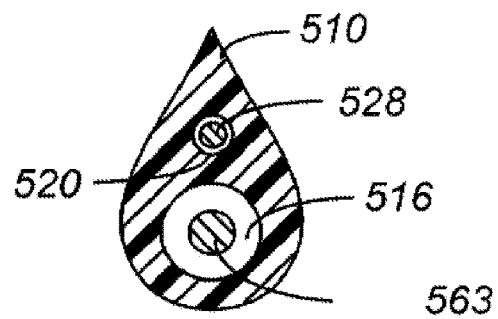
FIG. 6E illustrates a cross-sectional view of a pacing catheter, a lead and a guidewire within a guiding catheter along line 6E of FIG. 6A.

FIGS. 6C-6E depict cross-sectional views of the embodiment depicted in FIG. 6A advanced along a guidewire 528 and having a pacing catheter 530 therein. FIG. 6C depicts a guidewire 528 within the guidewire lumen 520 of the elongate sheath or guiding catheter 510. In this view, only the nose 512 of the guiding catheter 510 is shown as a cross-section along line 6C of FIG. 6A. FIG. 6D depicts an axial cross-sectional view of the guiding catheter 510 of FIG. 6A which has been advanced along a guidewire 528 and has a pacing catheter 530 therein. In the FIG. 6D view, FIG. 6A is cut along line 6D, and the view is an axial cross-section looking proximally from line 6D of FIG. 6A. This view, thus, shows the pacing needle electrode 532 of the pacing catheter 530 within the pacing catheter lumen 520 of the guiding catheter 510, as well as the guidewire 528 within the guidewire lumen 520 of the guiding catheter 510. FIG. 6E depicts a cross-sectional view of pacing catheter 530, lead 536 and guidewire 528 within guiding catheter 510 cut along line 6E of FIG. 6A. In all views of the FIG. 6 embodiments, the guiding catheter 510 has a teardrop shape along its distal length at least, including along its nose 512. The teardrop shape of the guiding catheter 510 may extend the entire length of the catheter 510, or may stop at a first point proximal to the teardrop distal portion, and restart at a second point proximal to the first point.

Another way to address avoiding perforating an undesired artery (e.g., a coronary artery lying on the LV summit 28) when piercing the coronary sinus 80 to anchor 234 the LV pacing electrode 532, is through visualization of the individual patient's coronary anatomy. Recording and storing appropriate coronary angiographic views and superimposing them on the live fluoroscopic views will prevent the operator from advancing the pacing catheter 530 into a location where a coronary artery branch (not shown) resides. Such a method can also assist in placement of the electrode 532 at the target location.

Additionally, as will be appreciated by those skilled in the art, other techniques can be used to determine the location of coronary arteries and to find and place an electrode 532 in the target location. For example, in addition to performing an angiogram, a physician can employ an intravascular ultrasound device 550 to determine the location of arteries. Use of any of the features described above alone or in combination with each other can reduce the likelihood of piercing a coronary artery or the pericardium and missing the target location.

Use of such a device in combination with an embodiment of the guiding catheter 610 described herein is depicted in FIG. 7A and FIG. 7B. FIG. 7A depicts an imaging system, such as an ultrasound assembly system, within a guiding catheter 610 described herein. Use of an imaging system can facilitate recording angiographic images and live fluoroscopy, or recorded angiographic images and life intravascular ultrasound. In this embodiment, a guiding catheter 610 having two lumens 616, 620 has been advanced along a guidewire 628 and an ultrasound catheter 654 has been advanced within the guiding catheter 610 second lumen 616 (pacing catheter lumen 616). The ultrasound assembly system, or the ultrasound catheter 654 and ultrasound device 650, is depicted within the pacing catheter lumen 616 of the guiding catheter 610 prior to exiting the pacing catheter exit port 614. In the embodiment depicted in FIG. 7B, the guiding catheter 610 has been advanced along a guidewire 628 and the ultrasound catheter 654, having an ultrasound device detecting end 652, has been advanced out the distal end of the elongate sheath 610 (i.e., guiding catheter 610) through the pacing catheter exit port 614. While examples of intravascular ultrasound mechanisms have been provided, the systems and methods described herein may be adapted for use with other ultrasound mechanisms, such as for transesophageal echocardiography, where for example, an ultrasound probe (e.g., ultrasound catheter) may be delivered through the esophagus to provide real-time ultrasound image(s) of the heart and nearby vasculature.

Use of ultrasound in cooperation with targeted placing of a pacing lead 636 at the target location proximal to the His bundle and near the orifice of the coronary sinus is previously undisclosed. Additionally, use of such ultrasound in coordination with a teardrop shaped catheter to assist an operator at a proximal end of the catheter in the determination of the orientation of the distal end of the device may facilitate steering and positioning.

In some systems, the guiding catheter may be echogenic. For example, a distal end 604 (e.g., at or near the exit lumen(s)) may comprise one or more echogenic features. An echogenic feature may be an echogenic surface. Echogenicity refers to a surface's ability to reflect incident ultrasound waves back to a sensor. The more a surface reflects waves back to the sensor the greater its image will appear on an ultrasound display. For example, an echogenic surface may comprise a bumpy or uneven surface. In some cases, such uneven surface may permit trapping or carrying of air pockets or bubbles, which is echogenic. There are a variety of different techniques suitable to increase a surface's echogenicity, including the selection of particular materials, and/or the use of grooves or recesses, bumps, coatings, indentations, and the like, and combinations thereof. The echogenic feature may be included in any strategic location of the guiding catheter such as at or near an end (e.g., distal end) or at or near one or more lumens. The echogenic feature may be located at a reference point relative to (e.g., a known vector from) a strategic location (e.g., end of catheter, lumen, etc.) to facilitate visualization of the guiding catheter. The guiding catheter may comprise a single echogenic feature. The guiding catheter may comprise a plurality of echogenic features, e.g., at a plurality of locations or a single location. The echogenicity of the guiding catheter may enhance visualization of the guiding catheter. A technician or physician may be able to more precisely position the tip using such enhanced visualization.

II. METHODS OF USE

Figure 8B:
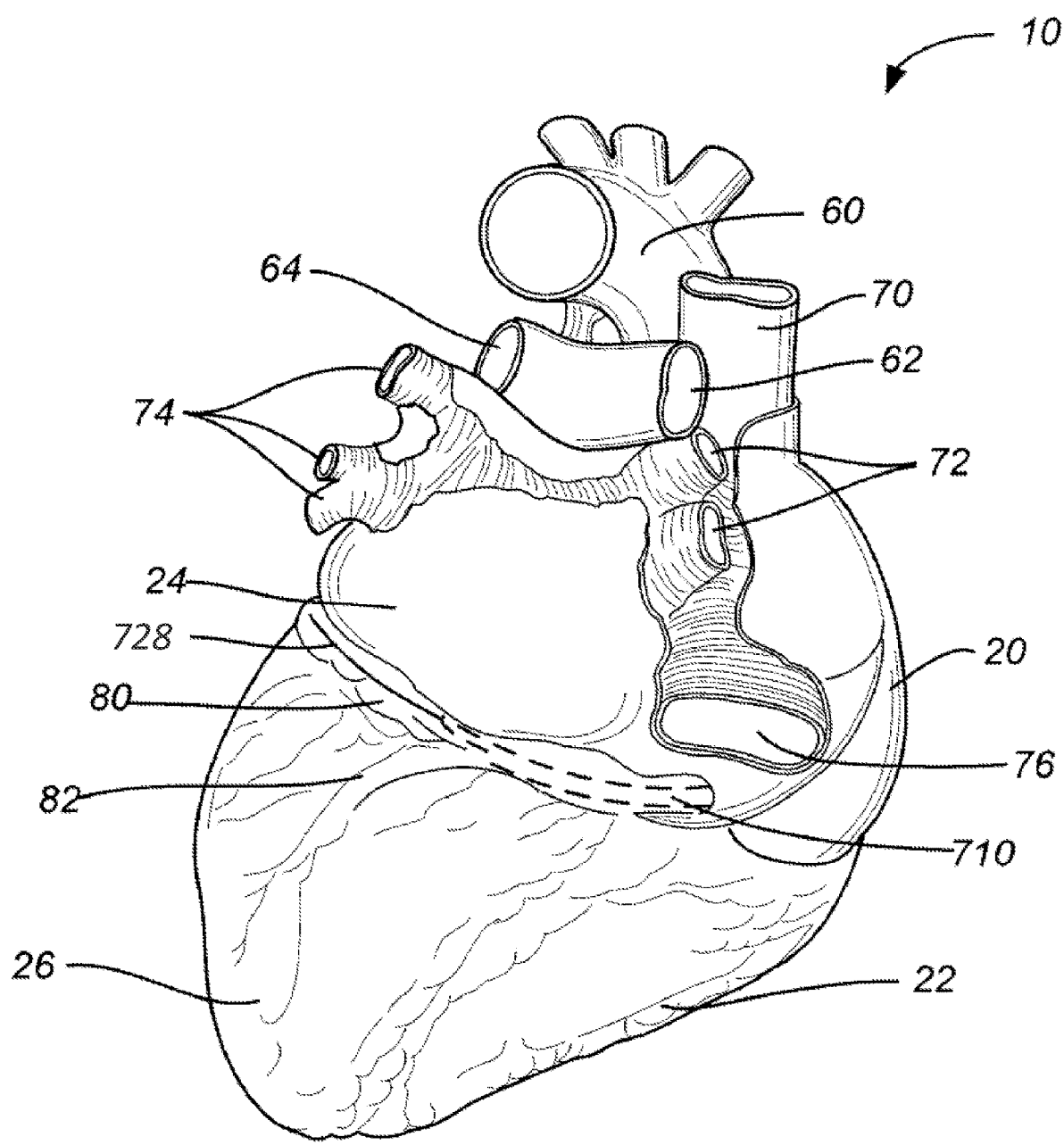
FIG. 8B illustrates a posteroinferior view of a heart wherein a guiding catheter has been advanced along a guidewire and into the coronary sinus.

In FIG. 8A, a cross-sectional view of a heart right atrium 20, right ventricle 22, mitral valve 32, tricuspid valve 30, and right pulmonary artery 62 is shown. In this depiction, a guiding catheter 710 is shown being advanced along a guidewire 728 which has been inserted through the superior vena cava 70, into the right atrium 20, and then into coronary sinus 80. FIG. 8B depicts a posteroinferior view of heart wherein a guiding catheter 710 embodiment has been advanced along guidewire into coronary sinus 80. It will be appreciated that while FIGS. 8B-8F show the guiding catheter 710 having advanced an arbitrary distance into the coronary sinus 80 distance, the operator will stop advancement upon reaching the target location, such as near the His bundle (e.g., example location 25 near the orifice of the coronary sinus, etc.) or at another desired location of the left ventricular summit (e.g., through a wall of the coronary sinus). Where the device provides radiopaque markers, the markers can be used to determine the location of the distal end of the device relative to the anatomy as the catheter 710 is advanced through the vasculature. Additionally, the cross-sectional shape, e.g., tear drop shape discussed previously, can be viewed to determine the position of, for example, the pacing catheter exit lumen 714 relative to the coronary anatomy so that the electrode can be advanced out of the guiding catheter and optimally positioned at the left ventricular summit.

Figure 8C:
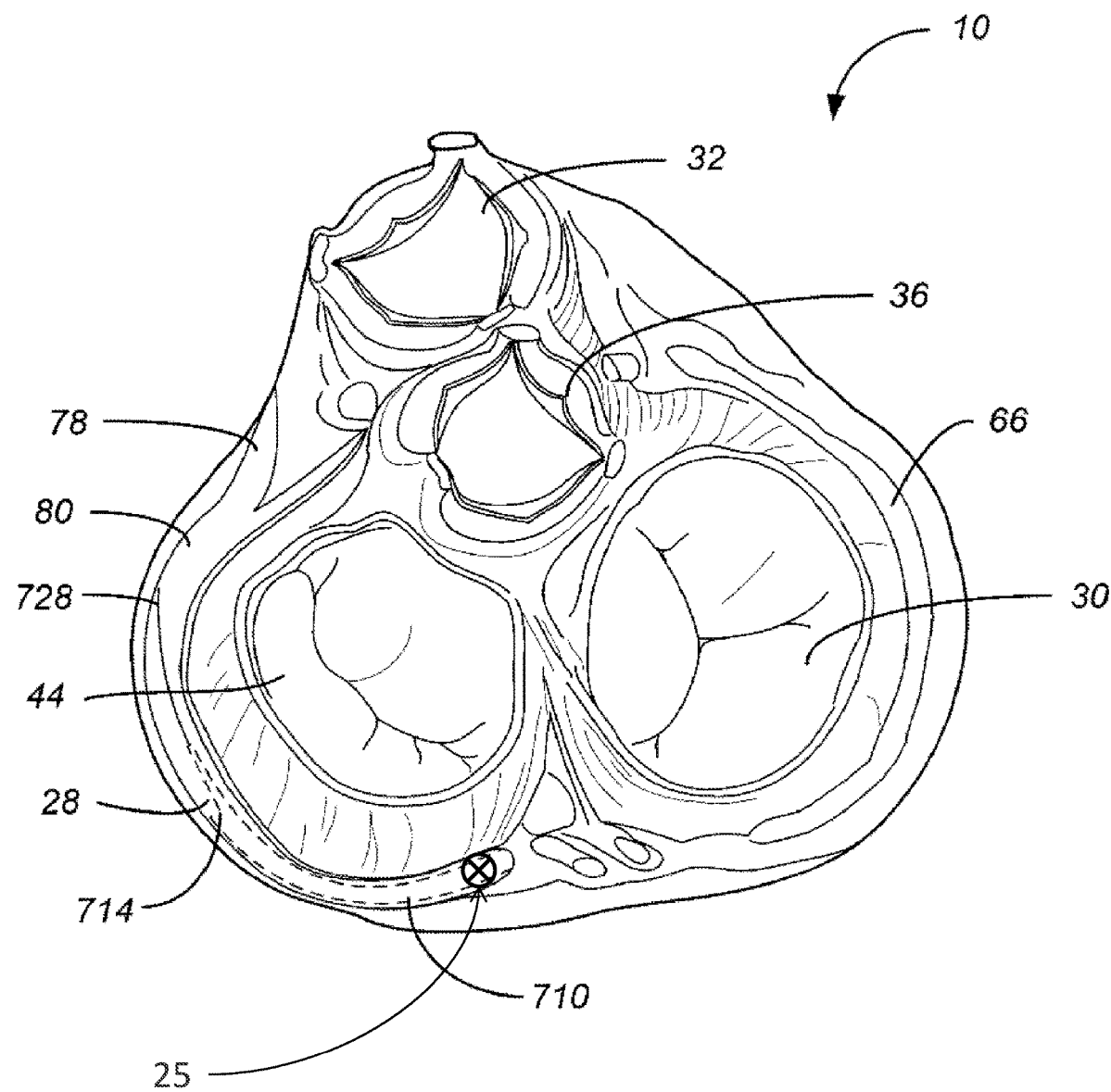
FIG. 8C illustrates a cross-sectional view of a heart in systole wherein a guiding catheter has been advanced along a guidewire into the coronary sinus, and wherein the guiding catheter has been positioned with the pacing catheter distal exit port 68 at about the apex or summit 14 of the left ventricle.
Figure 8D:
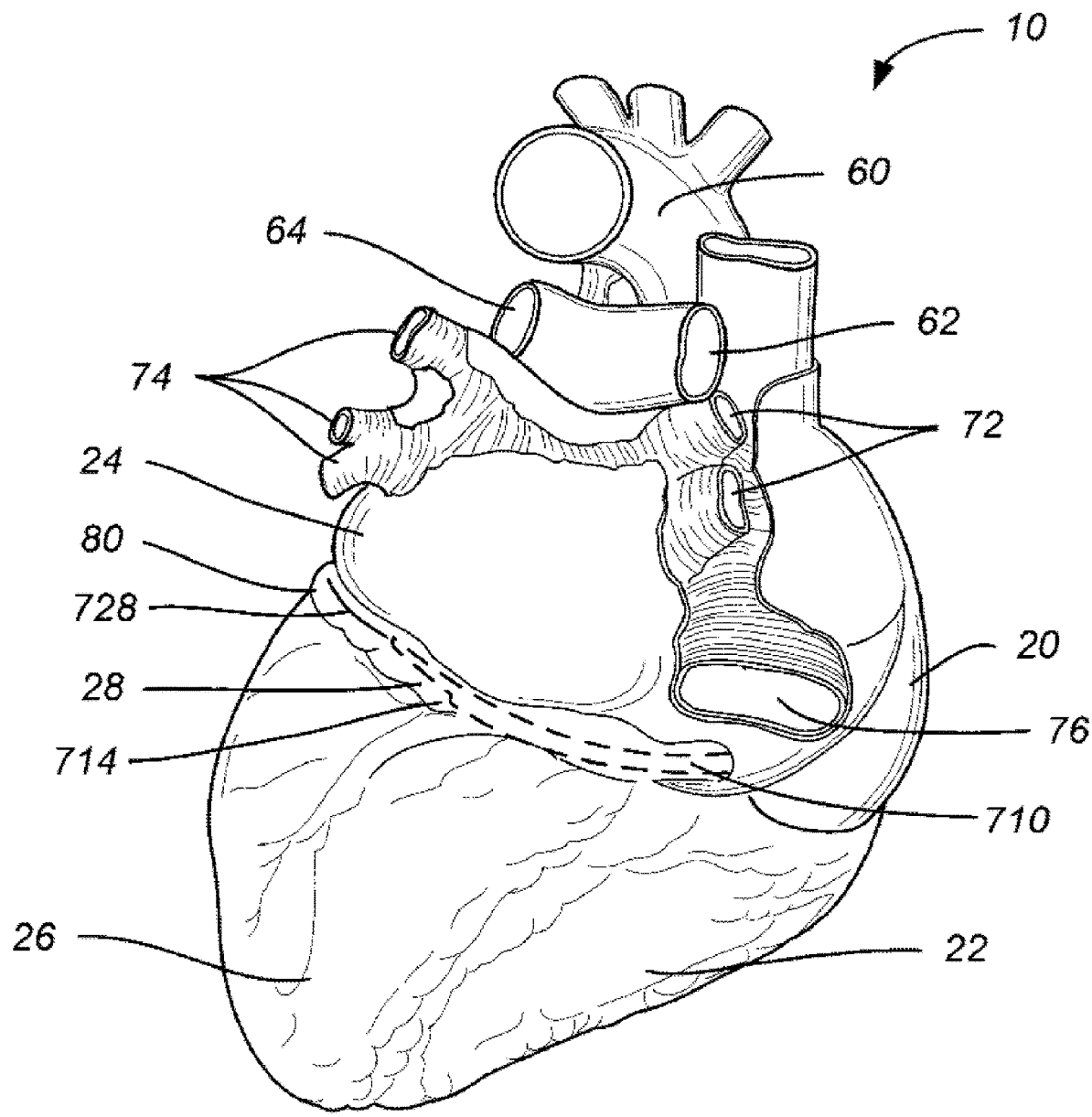
FIG. 8D illustrates a posteroinferior view of a heart in systole wherein a guiding catheter has been advanced along a guidewire into a coronary sinus, wherein the guiding catheter has been positioned with the pacing catheter distal exit port at about the apex or summit of left ventricle.

FIG. 8C, in one example, depicts a cross-sectional view of heart in systole wherein a guiding catheter 710 embodiment has been advanced along a guidewire 728 into the coronary sinus 80, and wherein the guiding catheter 710 has been positioned with the pacing catheter distal exit port 714 (lumen) at about the apex or summit 28 of left ventricle 26. FIG. 8D shows a posteroinferior view of the same guiding catheter 710 and guidewire 728 placement as shown in FIG. 8C. FIG. 8D depicts a posteroinferior view of heart in systole wherein an embodiment of the guiding catheter 710 has been advanced along a guidewire 728 into coronary sinus 80, wherein the guiding catheter 710 has been positioned with the pacing catheter distal exit port 714 at about the apex or summit 28 of left ventricle 26.

Figure 8E:
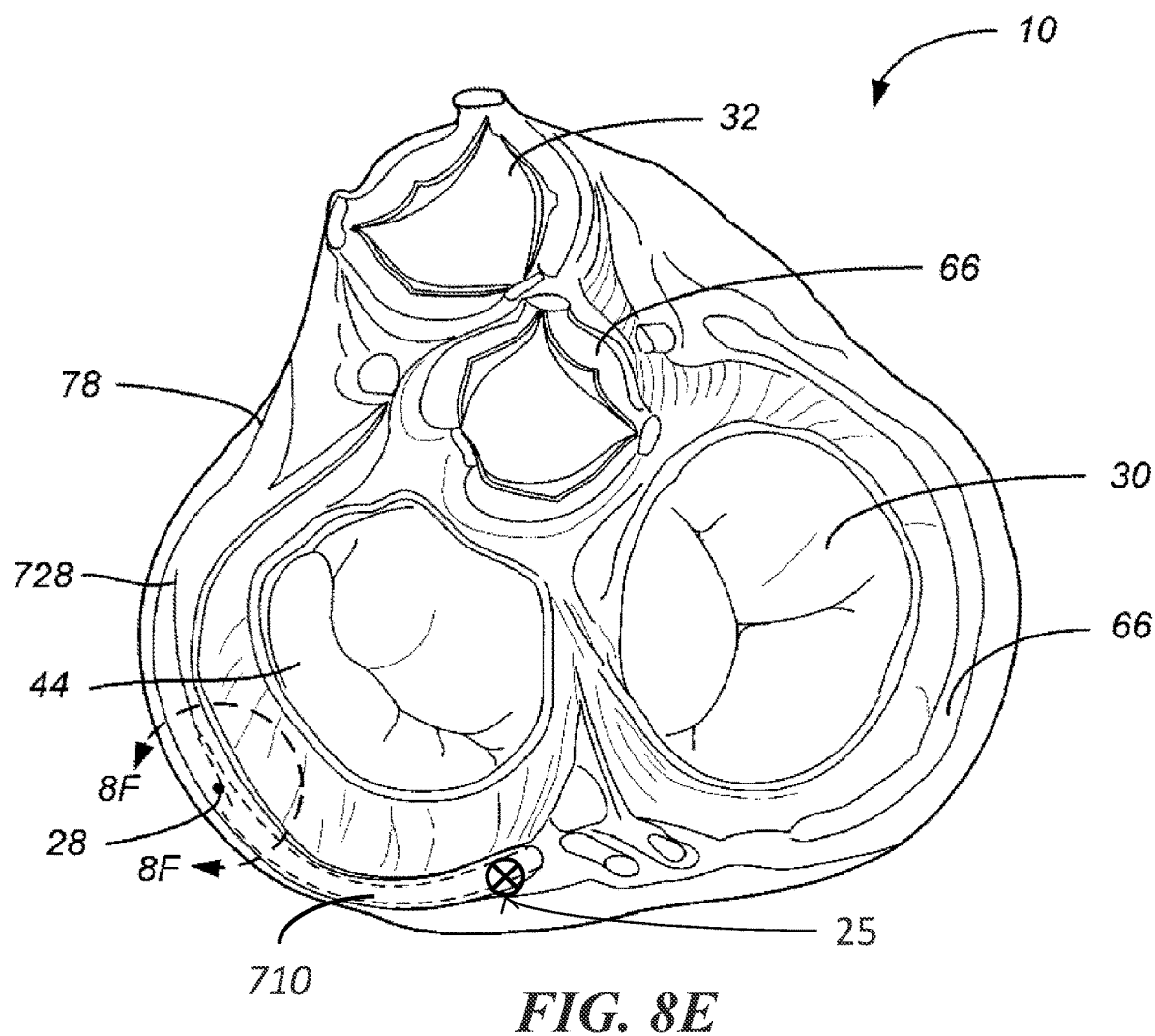
FIG. 8E illustrates a posteroinferior view of a heart in systole wherein a pacing catheter has exited a guiding catheter which has been advanced along a guidewire into the coronary sinus, and wherein the guiding catheter has been positioned with the pacing catheter exit port at apex or summit of left ventricle.
Figure 8F:
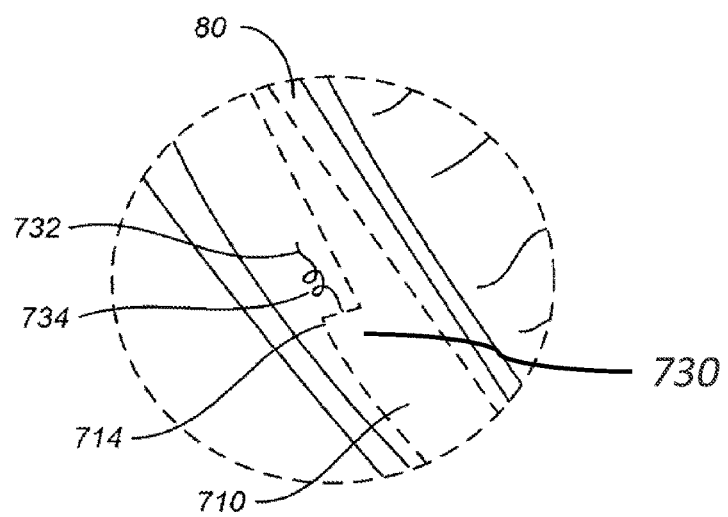
FIG. 8F is a zoomed-in depiction of the LV summit.

FIG. 8E depicts a posteroinferior view of heart in systole wherein an embodiment of a pacing catheter 730 has exited an embodiment of a guiding catheter 710 which has been advanced along a guidewire 728 into coronary sinus 80. In this depiction, the guiding catheter 710 has been positioned with its pacing catheter exit port 714 at apex or summit 28 of left ventricle 26. FIG. 8F also shows a zoomed-in depiction of the LV summit 28 region of the coronary sinus 80 showing the pacing needle electrode 732 and anchor 734 of an embodiment of the pacing catheter 730 exiting the pacing catheter exit port 714 of an embodiment of the guiding catheter 710. In another embodiment (not shown), the guiding catheter 710 which has been advanced along guidewire 728 into coronary sinus 80 is positioned with its pacing catheter exit port 714 at example location 25 near the His bundle and near the orifice of the coronary sinus 80, such that the needle end of the pacing catheter 730 exiting the pacing catheter exit port 714 is embedded in cardiac tissue at the example location 25.

In operation, the sheath of the guiding catheter 710 is placed in standard Seldinger fashion over the guidewire into the coronary sinus 80 and the thin nose 712 portion of the guiding catheter 710 extends into the coronary sinus 80 until it is lodged in the sinus and can be advanced no further. In order to accommodate small, medium and large hearts, this sheath 710 may need to be made in several sizes. The guiding catheter 710 carries this pacing catheter 730 into the coronary sinus 80, where it can be directed, using the radiopaque markers and the cross-sectional shape, to pierce the wall of the coronary sinus 80 at the target location.

Once the electrode is optimally positioned, at the left ventricular summit and anchored, the sheath is removed, and the proximal end of the electrode can be attached to a device for operation. Suitable devices include, for example, ICDs, such as those described in: U.S. Pat. No. 7,203,547 for System and method of implementing a prophylactic pacer/defibrillator; U.S. Pat. No. 7,203,546 for System and method of implementing a prophylactic pacer/defibrillator; U.S. Pat. No. 7,200,434 for Control of arbitrary waveforms for constant delivered energy; U.S. Pat. No. 7,158,825 for Implantable cardioverter defibrillator with leakage detection and prevention system; U.S. Pat. No. 7,151,963 for Control of arbitrary waveforms for constant delivered energy; U.S. Pat. No. 7,103,409 for Atrial and ventricular implantable cardioverter-defibrillator and lead system; U.S. Pat. No. 6,701,187 for Implantable cardiac stimulation device and method for prolonging atrial refractoriness; U.S. Pat. No. 6,675,042 for Defibrillation shock strength determination technology; U.S. Pat. No. 6,633,780 for Cardiac shock electrode system and corresponding implantable defibrillator system; U.S. Pat. No. 6,625,489 for Dynamic non-competitive atrial pacing; U.S. Pat. No. 6,574,505 for Atrial and ventricular implantable cardioverter-defibrillator and lead system; U.S. Pat. No. 6,567,697 for Method and apparatus for electrically forcing cardiac output in an arrhythmia patient; U.S. Pat. No. 6,377,852 for Implantable cardiac stimulation device and method for prolonging atrial refractoriness; U.S. Pat. No. 6,363,280 for Ventricular synchronized atrial pacing mode of implantable cardioverter/defibrillator; U.S. Pat. No. 6,282,444 for Implantable device with electrical infection control; U.S. Pat. No. 6,275,734 for Efficient generation of sensing signals in an implantable medical device such as a pacemaker or ICD; U.S. Pat. No. 6,094,597 for Implantable medical device incorporating distributed core, step-up transformer; U.S. Pat. No. 6,067,471 for Atrial and ventricular implantable cardioverter-defibrillator and lead system; U.S. Pat. No. 5,957,956 for Implantable cardioverter defibrillator having a smaller mass; U.S. Pat. No. 5,944,746 for ICD with continuous regular testing of defibrillation lead status; U.S. Pat. No. 5,919,213 for Implantable defibrillator system for generating a biphasic waveform with enhanced phase transition.

A method for pacing a heart of a patient is provided. In a first operation, a sheath is introduced into the vasculature of the patient, such as via the superior vena cava 70, into the right atrium 20, and then into coronary sinus 80. The sheath is steered within the coronary sinus to lodge a distal end of the sheath to a target location that is proximal to the bundle of His above a septum separating a left ventricle and a right ventricle of the heart. A pacing lead is advanced through a lumen of the sheath to the target location. The pacing lead is coupled to the cardiac tissue at the target location, and the sheath is removed. The bundle of His is electrically stimulated by activating the pacing lead (e.g., via an ICD).

The target location may be at or near the His bundle. For example, the target location may be within at most 25 millimeters (mm), 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm or less distance away from the His bundle. In some cases, the target location may be more than 25 mm distance away from the His bundle. In some cases, the target location may be at or near the orifice of the coronary sinus. For example, the target location may be within at most 25 millimeters (mm), 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm or less distance away from the orifice of the coronary sinus. In some cases, the target location may be more than 25 mm distance away from the orifice of the coronary sinus.

Another method for pacing a heart of a patient is provided. In a first operation, a sheath is introduced into the vasculature of the patient, such as via the superior vena cava 70, into the right atrium 20, and then into coronary sinus 80. The sheath is steered within the coronary sinus to lodge a distal end of the sheath to a target location that is proximal to a left ventricular summit through a wall of the coronary sinus. A pacing lead is advanced through a lumen of the sheath to the target location, and directed to perforate the wall of the coronary sinus to pass through to the left ventricular summit. The pacing lead is coupled to the cardiac tissue, and the sheath is removed. The catheter may comprise one or more side electrodes attached to a lateral surface of a body of the catheter. The one or more side electrodes may, for example, comprise two bipolar electrodes. The one or more side electrodes may interface and/or be secured to an atrial wall. The heart is electrically stimulated by activating the pacing leads in the left ventricular summit and the right atrial wall. In some instances, the catheter body may comprise an anchor to stabilize the placement of the pacing leads in the heart. For example, such anchor may be coupled to one or more locations in the cardiac tissue in contact with the anchor. In some instances, the anchor may be weighted to facilitate stabilization. In some instances, the anchor may comprise a spring or coil. The anchor may have any shape, size, or form to facilitate stabilization.

A method for determining a pacing location in the heart and/or positioning a catheter is provided. A cardiac stimulation device (e.g., implantable cardiac stimulation device) can comprise a two-part anchor electrode, as described above, for example. The two-part anchor electrode may comprise a first anchor (e.g., spring, coil, straight screw, conical screw, etc.) followed by a second anchor (e.g., an extended needle). The first anchor may be proximal to a body of the device relative to the second anchor. The second anchor may be distal to the body of the device relative to the first anchor. The first and second anchors may be first and second segments of a single, continuous anchor structure. The method may comprise temporarily anchoring the electrode to a first location using the second anchor, and activating the electrode for a diagnostic of the first location. Subsequently, the second anchor may be removed from the first location and temporarily anchored to a second location, and the catheter may be activated for a diagnostic of the second location. The two diagnostic results can be compared to determine a more efficient pacing location of the first location and the second location. Upon determination of the pacing location, the catheter may be anchored to such location using both the first anchor and the second anchor for increased stability. Any number of locations may be tested using the second anchor temporarily anchored to the test location(s). In alternative methods, if a first location tested yields successful diagnostic results (e.g., efficient contraction), without removing the second anchor, the first anchor may be further anchored to the first location without having to test a second location or multiple locations. A single location and/or each location may be tested for efficacy of the pacing location. During diagnostics, efficacy may be determined by observing or monitoring efficient contraction of the heart, pacing of the heart at its different chambers with correct timing, ECG signals indicative of pacing, and/or other techniques known in the art. In some instances, if the first n locations yield unsuccessful or otherwise undesirable diagnostic results, the two-part anchor may be completely anchored at the first successful diagnostic result, at the (n+1)th location. Beneficially, the temporary anchor provided by the second anchor (e.g., extended needle) may both minimally perturb the test location tissue, e.g., compared to anchoring both the first anchor and the second anchor, and provide sufficiently stability to generate diagnostic test results. An individual or combined linear length of the first anchor and the second anchor may be particularly useful for piercing and/or traversing intermediary tissue (e.g., wall or membrane) disposed in a path to the target pacing location.

In some instances, the methods described herein can further comprise identifying anatomical structures, such as via (i) obtaining an angiogram, obtaining a live fluoroscopic image, correlating the angiogram with the live fluoroscopic image, and analyzing the correlated images, and/or (i) obtaining an angiogram, obtaining a live intravascular ultrasound image, correlating the angiogram with the live intravascular ultrasound image, and analyzing the correlated images. Alternatively or in combination with an angiogram, ultrasound images, for example, from intravascular and/or transesophageal ultrasound devices, may be used.

III. BI-PACING SYSTEMS AND METHODS

Bi-pacing systems and methods are provided, wherein a heart is paced by stimulating two locations in the heart, a first location and a second location via a first pacing lead and a second pacing lead, respectively. The first location can be the target location proximal to the bundle of His, as described elsewhere herein. For example, in a first operation, a sheath is introduced into the vasculature of the patient, such as via the superior vena cava 70, into the right atrium 20, and then into coronary sinus 80. The sheath is steered within the coronary sinus to lodge a distal end of the sheath to the target location that is proximal to the bundle of His above a septum separating a left ventricle and a right ventricle of the heart. A first pacing lead is advanced through a lumen of the sheath to the target location. The first pacing lead is coupled to the cardiac tissue at the target location. Optionally, the sheath is removed.

The second location can be another location. For example, the second location can be the LV summit, as described elsewhere herein. For example, in a second operation, a sheath is introduced into the vasculature of the patient (if removed, otherwise, the same sheath used for the first pacing lead can be used), such as via the superior vena cava 70, into the right atrium 20, and then into coronary sinus 80. The sheath is steered within the coronary sinus to lodge a distal end of the sheath to the summit 28 of the left ventricle. A second pacing lead is advanced through a lumen of the sheath to the second location. The second pacing lead perforates the coronary sinus with the sharp needle at the apex of the left ventricle and anchored. In a next operation, a cardiac stimulation device electrically coupled to the first and second pacing leads may deliver signals to the first pacing lead and the second pacing lead to stimulate the heart. Alternatively, the second location can be another location in the heart, such as the right atrium of the heart, right ventricle of the heart, or an apex of the left ventricle. Alternatively, any of the second locations described herein may be the first location.

Figure 9A:
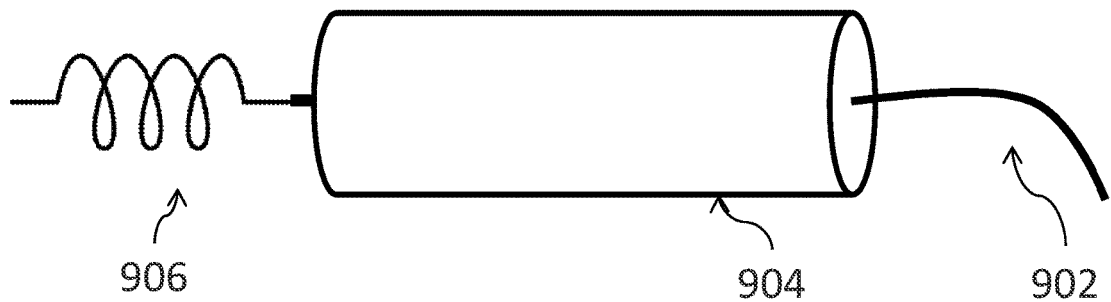
FIGS. 9A-9B illustrate side views of exemplary implantable pacing systems.
Figure 9B:
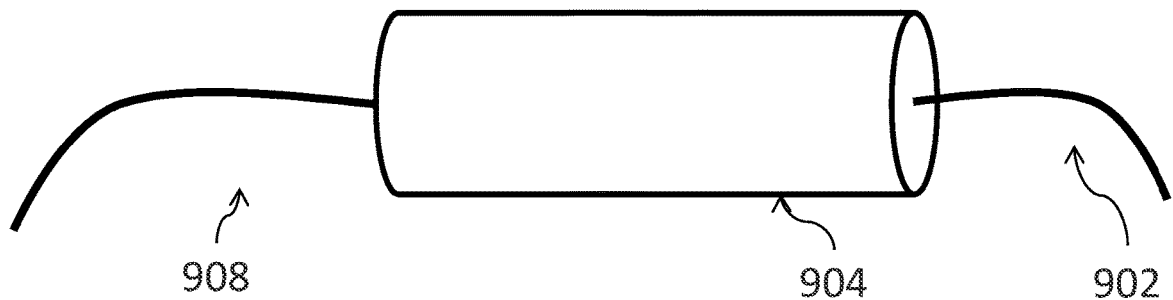

In some aspects, provided are implantable pacing systems that can be implanted into a patient. FIGS. 9A-9B illustrate examples of implantable pacing systems. An encasement 904 can comprise therein a cardiac stimulation device, such as an ICD described herein, and a power source coupled to the cardiac stimulation device. For example, the power source may include one or more batteries, capacitors, supercapacitors, and the like. The power source may be rechargeable. In some instances, the power source may be rechargeable via wireless transmission of energy. The encasement may comprise therein electric circuitry coupling the cardiac stimulation device, the power source, and one or more electrodes. In FIG. 9A, one embodiment of the implantable system comprises a first electrode 902 protruding from a proximal end of the encasement and a second electrode 906 protruding from a distal end of the encasement. The first electrode 902 has a substantially straight structure. The first electrode 902 may or may not have one or more curved features or angled features. Such curved or angled features may facilitate stable coupling and/or anchoring of the first electrode to cardiac tissue. The second electrode 906 has a substantially coil or helical structure. The second electrode 906 may or may not have one or more linear or straight features. The substantially coil or helical structure may facilitate stable coupling and/or anchoring of the second electrode to cardiac tissue. It will be appreciated that while FIGS. 9A-9B illustrates the two electrodes protruding from opposing faces of the encasement 904, the configuration is not limited to the illustration. For example, the two electrodes may protrude from adjacent faces of the encasement or from the same face. The encasement may be sized and shaped to encase the cardiac stimulation device, power source, and electric circuitry. The encasement may have one or more substantially planar surfaces and/or substantially curved surfaces. In some cases, the encasement may have substantially planar surfaces from which electrodes protrude. In other cases, the encasement may have substantially curved surfaces from which electrodes protrude. In another embodiment, as illustrated in FIG. 9B, the leadless system comprises a first electrode 902 protruding from a proximal end of the encasement and a second electrode 908 protruding from a distal end of the encasement 904. The second electrode 908 has a substantially straight structure. The first electrode 902 may or may not have one or more curved features or angled features. Such curved or angled features may facilitate stable coupling and/or anchoring of the first electrode to cardiac tissue.

Figure 9C:
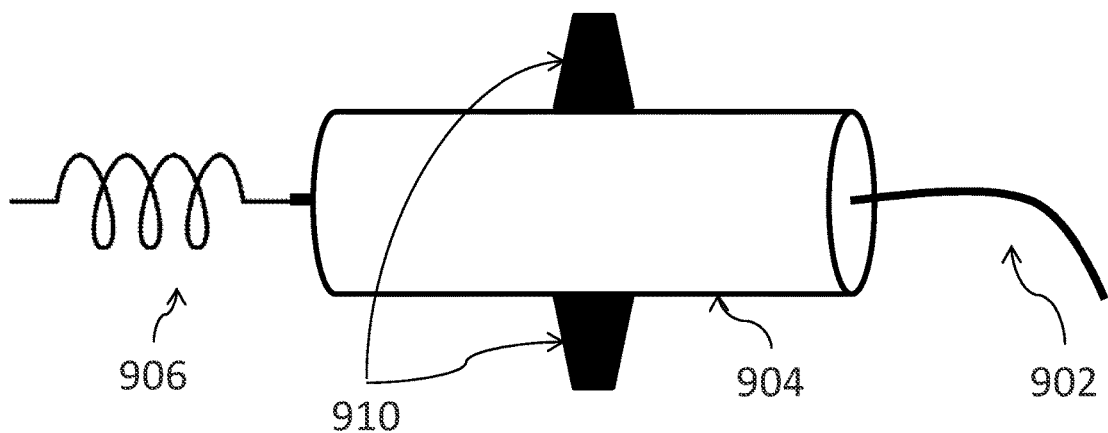
FIG. 9C illustrates a side view of an exemplary implantable pacing system with expandable fins.

FIG. 9C illustrates an example of an implantable device having one or more expandable fins 910 protruding from a lateral surface of the encasement 904. The expandable fins 910 may be configured to interface cardiac tissue and stabilize a placement of the encasement 904. The expandable fins 910 may be folded (not shown in FIG. 9C) during introduction of the device to the vasculature of the patient. When folded, the expandable fins may conform to a lateral surface form or shape of the encasement 904 such as not to hinder movement of the device through the vasculature.

The two electrodes (e.g., 902 and 906; 902 and 908; etc.) may each be coupled to two different locations in the heart. For example, the two different locations can be selected from the target location (at or near the His bundle or coronary sinus orifice), coronary sinus, right ventricle, right atrium, left ventricle summit, and the like. Alternatively, the implantable systems may have only one electrode for coupling to a single location in the heart. Alternatively, the implantable systems may have more than two electrodes. In such cases, each of the electrodes may be coupled to different location in the heart or two or more electrodes (of the total electrodes) may be coupled to the same location.

Figure 10:
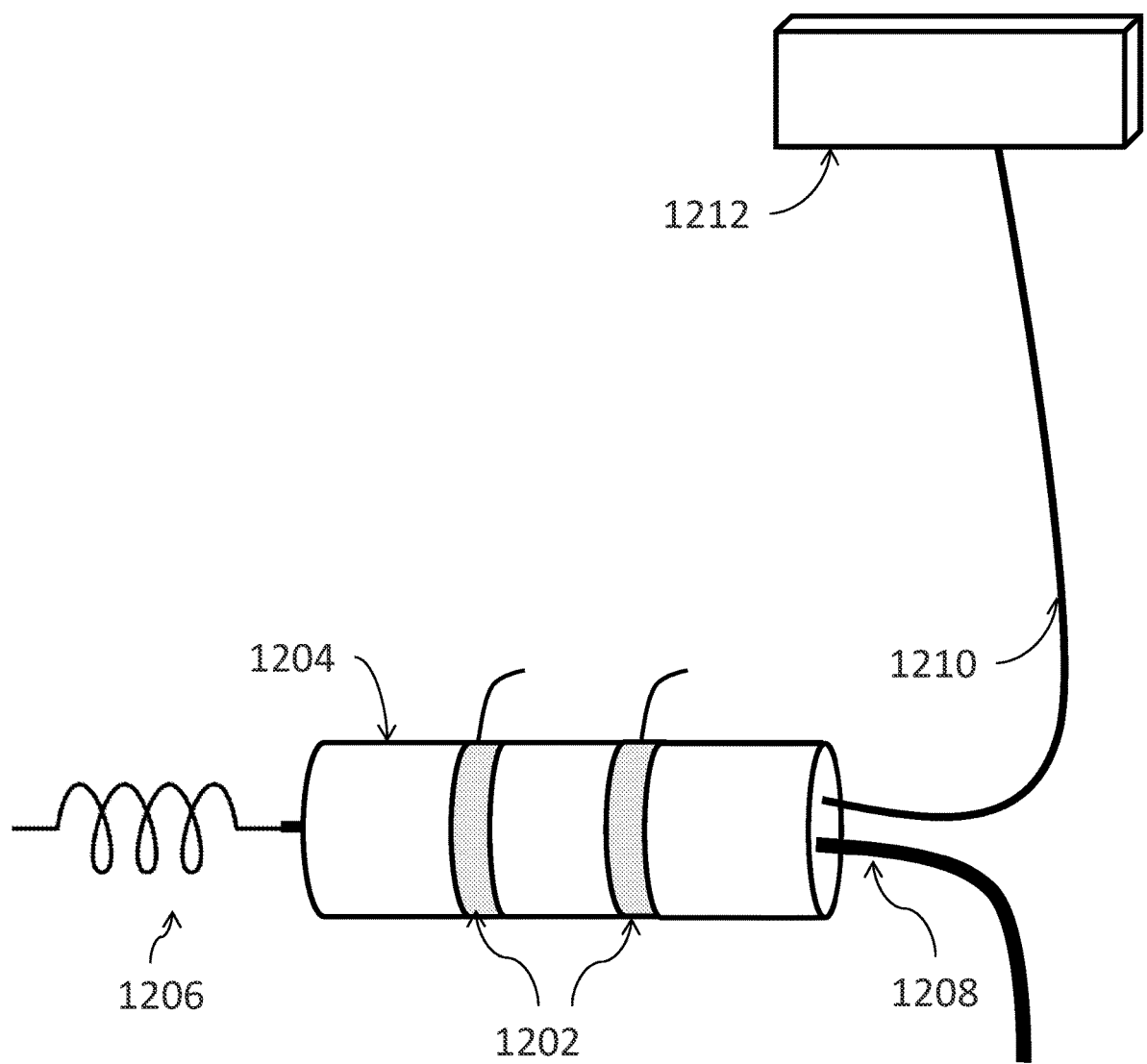
FIG. 10 illustrates an example of a pacing catheter configured to pace both an atrial wall and left ventricular summit.

In some aspects, provided are pacing systems that can achieve pacing of multiple locations in the heart, such as the right atrial wall and left ventricular summit. FIG. 10 illustrates an example of a pacing system. A catheter can comprise a body 1204 electrically coupled to a cardiac stimulation device 1212 such as via one or more wires 1210. The cardiac stimulation device may be electrically coupled to a power source. For example, the power source may include one or more batteries, capacitors, supercapacitors, and the like. The power source may be rechargeable. In some instances, the power source may be rechargeable via wireless transmission of energy. The catheter can comprise a first electrode 1206 protruding from a proximal end of the body 1204 and one or more side electrodes 1202 protruding from a lateral surface of the body 1204. In some instances, the body 1204 may comprise therein electric circuitry coupling the cardiac stimulation device, the power source, and one or more electrodes (1204, 1206). The body 1204 may comprise one or more anchors 1208 configured to stabilize lead placement of the pacing catheter in the heart.

The first electrode 1206 can have any shape, size, or form. For example, the first electrode 1206 may have a substantially straight structure. The first electrode 1206 may or may not have one or more curved features or angled features. For example, as described with respect to FIGS. 4A-4E, the first electrode 1206 may have a straight coil-like feature or a conical coil-like feature in addition to a linear needle extending at a distal end from a surface of the body 1204. Such curved or angled features may facilitate stable coupling and/or anchoring of the first electrode 1206 to cardiac tissue. For example, the first electrode 1206 may have a substantially coil or helical structure that facilitates stable coupling and/or anchoring of the electrode to cardiac tissue. The one or more side electrodes 1202 can have any shape, size, or form. When there are multiple side electrodes, they may have substantially the same shape, size, and/or form. Alternatively, they may have different shapes, sizes, and/or forms. For example, a side electrode may have a substantially straight structure. The side electrode may or may not have one or more curved features or angled features. Such curved or angled features may facilitate stable coupling and/or anchoring of the side electrode to cardiac tissue. For example, the side electrode may have a substantially coil or helical structure that facilitates stable coupling and/or anchoring of the electrode to cardiac tissue. In some instances, the one or more side electrodes 1202 may take form as conductive lateral surface(s) or material(s) on such surface(s) of the body 1202, spaced apart by insulating lateral surface(s) or material(s) on such surface(s). Alternatively or in addition, the first electrode and/or side electrodes may protrude or be coupled to any surface (e.g., lateral, top, bottom, proximal, distal, etc.) of the body 1204 of the catheter. In some instances, the one or more anchors 1208 may be configured to stabilize the placement of the pacing leads in the heart. For example, such anchor may be coupled to one or more locations in the cardiac tissue in contact with the anchor. In some instances, the anchor may be weighted to facilitate stabilization. In some instances, the anchor may comprise a spring or coil. The anchor may have any shape, size, or form to facilitate stabilization. It will be appreciated that while FIG. 10 illustrates an anchor protruding from a distal surface of the body 1204, the anchor may protrude from any surface (e.g., lateral, top, bottom, proximal, distal, etc.) of the body 1204 of the catheter.

It will be appreciated that while FIG. 10 illustrates a cylindrical form of the body 1204, the body may have any shape, size, and/or form. It will be appreciated that while FIG. 10 illustrates two side electrodes, the catheter may comprise any number of side electrodes.

In an example operation, referring to FIG. 8A, the catheter body 1204 may be introduced to an opening of the coronary sinus 80 through the right atrium 20. The coronary sinus 80 opens into the right atrium 20, but its opening is disposed above and within a few millimeters of the left ventricular summit. Upon entry into the coronary sinus 80, the first electrode 1206 of the pacing catheter may perforate a wall of the coronary sinus 80 and pass into the left ventricular summit (e.g., 28 in FIG. 1C). For example, the first electrode 1206 may comprise a screw-in lead that perforates the wall of the coronary sinus and anchors into the cardiac tissue. The side electrodes 1202 may interface a right atrial wall. The side electrodes 1202 may be stabilized by anchoring into the cardiac tissue in the right atrial wall. The one or more anchors 1208 may stabilize the placement of the different electrodes, such as by anchoring into other cardiac tissue. The catheter body 1204 may be electrically coupled to the cardiac stimulation device 1212 such as via one or more wires 1210. The right atrial wall and the left ventricular summit may thereafter be electrically stimulated by activating electrical signals through the cardiac stimulation device 1212.

IV. TRANSCORONARY SINUS PACING

The present disclosure provides systems, devices, and methods for transcoronary sinus pacing that disintermediates pacing in the right ventricle. Though transvenous right ventricular (RV) pacing can cause clinically important adverse consequences, it remains a mainstay in current practice because it is easy to perform and can provide reliable pacing. Provided herein is a single pacing catheter that can pace both the left ventricular base and the right atrium without crossing the tricuspid valve, and reliable method thereof for placing this catheter that will be within reach of most implanting physicians. The method can comprise placing a guide wire in the coronary sinus over which a double lumen introducer is advanced securely into the coronary sinus. The pacing catheter in the second lumen can then be advanced about 1 centimeter (cm) to perforate the coronary sinus. This places the tip of the pacing catheter in the left ventricular (LV) base without crossing the tricuspid valve. After the double lumen introducer is removed, side electrodes on the pacing catheter wall can activate the right atrium as the catheter caroms off the right atrial wall to ascend the superior vena cava. This technique has the following advantages: (1) It eliminates the reduced LV function inherent in RV pacing; (2) It avoids the complications of crossing the tricuspid valve; (3) It reduces the load of pacing catheters in the venous system; and (4) It may simplify the design of the generator header.

Since the mid twentieth century, cardiac pacing has made substantial progress on many fronts, but there is a glaring exception. The present disclosure explains that exception, reviews the progress relevant to that exception, and outlines a technique to overcome it substantially improving cardiac pacing. The glaring exception is the continued use of the transvenous RV lead that crosses the tricuspid valve. This lead is easy to securely place and reliably activates the right ventricle causing an electrical depolarization that is identical with left bundle branch block. It has remained the mainstay of permanent cardiac pacing since the beginning. The shortcomings of this technique are easy to summarize, but took a long time to understand: (1) RV pacing reduces LV function by two related mechanisms; (2) The pacing catheter crosses the tricuspid valve and may lead to tricuspid regurgitation; and (3) First pacing the RV delays activation of the left ventricle and therefore prolongs QRS duration causing a more dysynchronous LV contraction. These problems have been known since the 1930's when Wiggers first paced a dog's heart and blood pressure went down. See Wiggers C J. The muscular reactions of the mammalian ventricles to artificial surface stimuli. Am J Physiol. 1925; 73: 346-378. The severity of this problem was not fully understood until Michael Sweeney solved an embarrassing issue that arose when the major pacing companies performed large randomized trials to compare VVI pacing to DDD pacing. See Sweeney M O, et al. Adverse effect of ventricular pacing on heart failure and atrial fibrillation among patients with normal baseline QRS duration in a clinical trial of pacemaker therapy for sinus node dysfunction. Circulation. 2003; 107: 2932-2937. VVI means a single pacing catheter sensing and pacing in the RV. DDD pacing means two separate pacing catheters, one in the atrium and one in the RV, each pacing and sensing in their respective locations. This mimics the atrioventricular synchrony that occurs in a normal heartbeat, and everyone assumed that DDD pacing would offer substantial hemodynamic benefit over VVI by mimicking a normal activation. The trials showed no benefit.

Sweeney divided some 10,000 patients from these randomized trials into two groups. He excluded those who had complete heart block because they paced in the ventricle 100% of the time. He studied those who had sick sinus syndrome. This latter group has intact AV conduction, but experiences unpredictable slowdowns from deficiencies of impulse formation in the atrium. Some rarely needed ventricular pacing, and some used it commonly. He divided sick sinus patients into those who paced in the ventricle more than 45% of the time and those who paced less than 45% in the ventricle. The randomized trial had recorded ventricular performance for every patient so Sweeney could compare ventricular function and outcomes for his two groups. He found that at every level of LV function, those who paced in the ventricle more than 45% had twice the incidence of heart failure in the following two years compared to those who paced less. To summarize, RV apex pacing is so deleterious to LV function that it negates the positive effects of AV synchrony. The technique has persisted because it is easy to perform, paces reliably, and most paced patients have good enough cardiac function, so the higher incidence of subsequent heart failure appears low or is written off as "pacemaker syndrome," a wastebasket diagnosis that concealed our ignorance.

Another large, randomized trial from the implanted cardioverter defibrillator (ICD) literature reached the same conclusion. This study compared ICD implant to ICD implant/VVI pacer in patients who had poor ventricular function and possible cardiac arrest. It was thought that the pacer would add to the safety of the ICD device by preventing severe bradycardia. The study showed that mortality was higher in those who VVI paced.

There is a second physiologic reason why RV pacing is bad for LV function. We have discussed the idea that it causes dysynchronous contraction. We can add that it delays closure of the mitral valve. The LV muscle at the base of the heart should contract early to close the mitral valve early in systole. This permits Starling's law to work properly. Increased filling of the LV causes increased contractility. In a normal contraction, the mitral valve closes early in systole as demonstrated by Cox in the Helical Heart model. Left bundle branch block and RV pacing cause the valve to close late, encouraging mitral regurgitation that defeats Starling's Law and reduces LV contractility.

For the reasons summarized above, biventricular pacing began in the early 2000's. The technique uses the same atrial and ventricular wires as the DDD device, but adds a third wire passed into the coronary sinus and down into a coronary vein along the LV base. This permits simultaneous or near simultaneous pacing of the RV and the LV base. The result is shorter activation time and less dysynchrony, and if properly placed, the LV wire activates the LV base early and reduces mitral regurgitation. Although it requires 3 pacing catheters, this technique has become standard for patients who have reduced LV function or who need defibrillators, and it can improve "functional" mitral regurgitation.

At present many agree that LV pacing alone will reduce or eliminate the physiologic problems caused by RV pacing because it does not cause left bundle branch block and therefore reduced LV function. Unfortunately the current techniques for LV pacing are neither reliable enough nor sufficiently reproducible to replace RV pacing.

The present disclosure provides solutions to the above described issues. The coronary sinus opens into the right atrium, but even at its os, sits atop the left ventricular summit, not the right. The summit of the left ventricle is within a few millimeters of this opening. Provided herein are double lumen introducers that stabilize in the coronary sinus, the introducers containing a screw in pacing catheter that perforates the coronary sinus and passes into the summit of the left ventricle. Side electrodes further up the shaft of the same pacing catheter will encounter the right atrial wall and permit atrial pacing. Thus, a single pacing catheter can pace the right atrial wall and left ventricular summit.

This approach has the potential to radically alter all aspects of transvenous pacing and certain aspects of ICD implantation. At least the following benefits are achieved: (1) The negative consequences of RV pacing will be eliminated; (2) The technical complications of crossing the tricuspid valve will be eliminated; (3) The total amount of foreign material in the venous system will be reduced; (4) The pacemaker header can be made smaller and more simply; (5) This design anticipates a leadless DDD pacing device that paces the right atrium and LV base.

V. EXAMPLE PACING SCHEMES

FIGS. 11A-J illustrate examples of different pacing schemes of the present disclosure. A heart 150 comprises a right atrium 1002, a right ventricle 1006, a left atrium 1004, and left ventricle 1008, where the right and left chambers are separated by a septum 1012. Also shown is an orifice of the coronary sinus 1010 and the His bundle 1014. Electrical stimulation may be provided to a pacing location by a device 1016. The device 1016 may comprise a catheter. The device 1016 may comprise one or more pacing leads and/or electrodes. In some instances, the device 1016 may be an implantable pacing system (as described elsewhere herein, such as with respect to FIGS. 9A-C). The device 1016 may not be implanted in some cases.

Figure 11A:
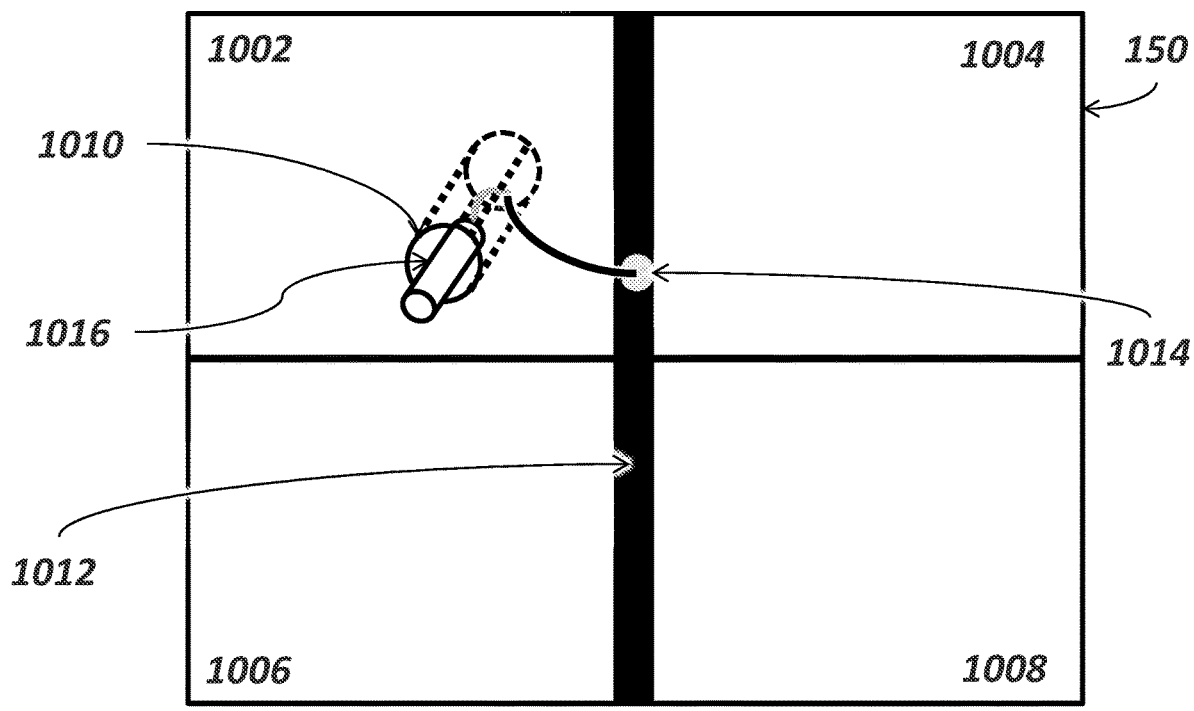
FIGS. 11A-J are schematic illustrations of different exemplary pacing schemes according to embodiments of the present disclosure.

In an example, as shown in FIG. 11A, the heart 150 is paced in a single location at or near the His bundle 1014 only, through and near the orifice of the coronary sinus 1010, such as within 1-2 cm of the orifice of the coronary sinus 1010.

Figure 11B:
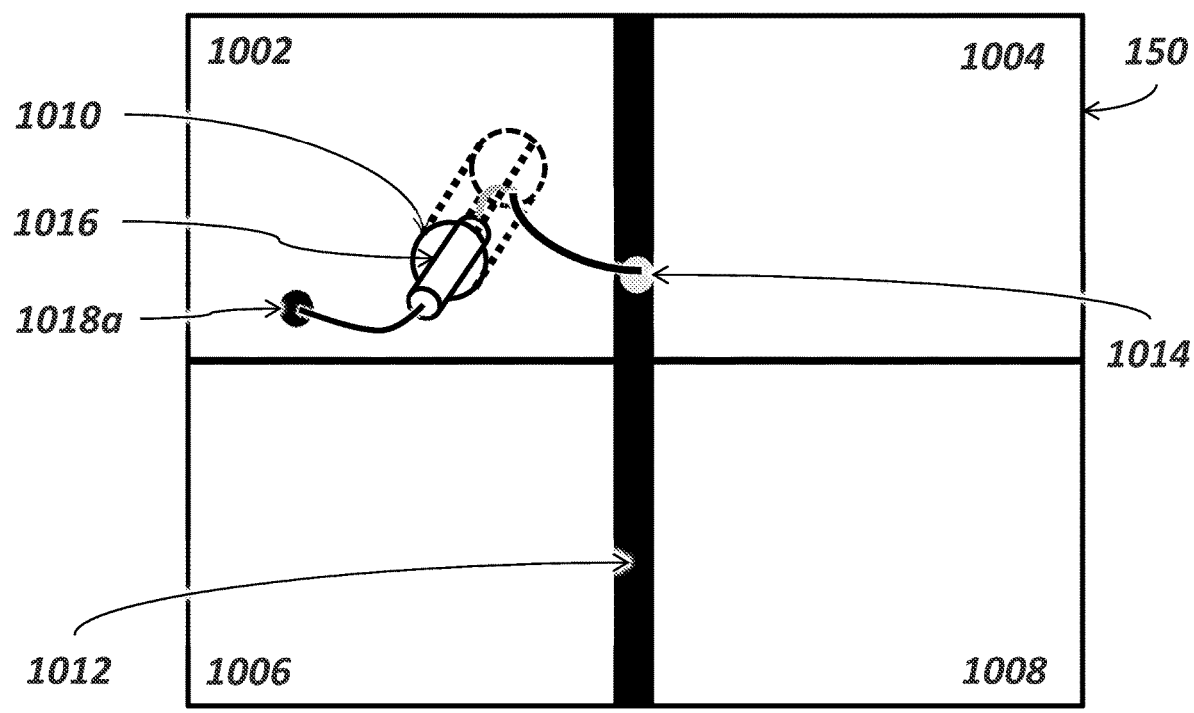

In some instances, the heart 150 is paced from two locations, such as via two pacing leads or using an implantable pacing system with two electrodes. In an example, as shown in FIG. 11B, the heart 150 is paced in two locations, a first location at or near the His bundle 1014, through and near the orifice of the coronary sinus 1010, and a second location 1018a in the right atrium 1002. The pacing device may be placed within the coronary sinus 1010 so that the leads that extend therefrom can advance through the walls of the coronary sinus to access the His bundle and wall of the right atrium.

Figure 11C:
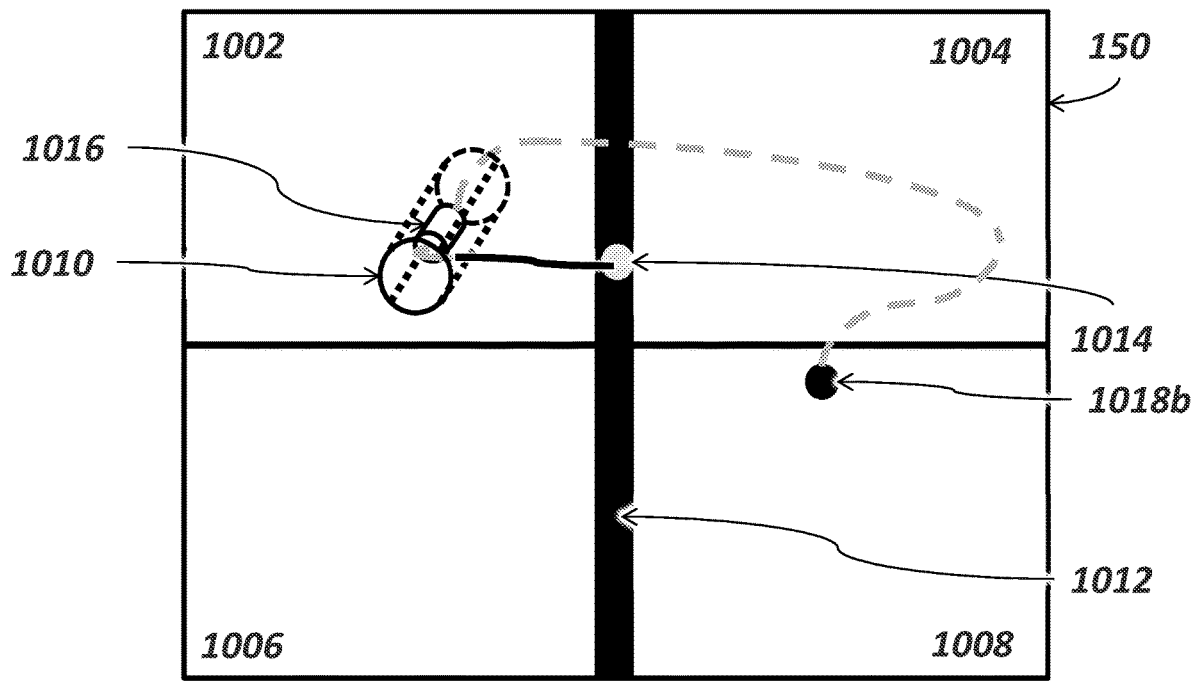
Figure 11D:
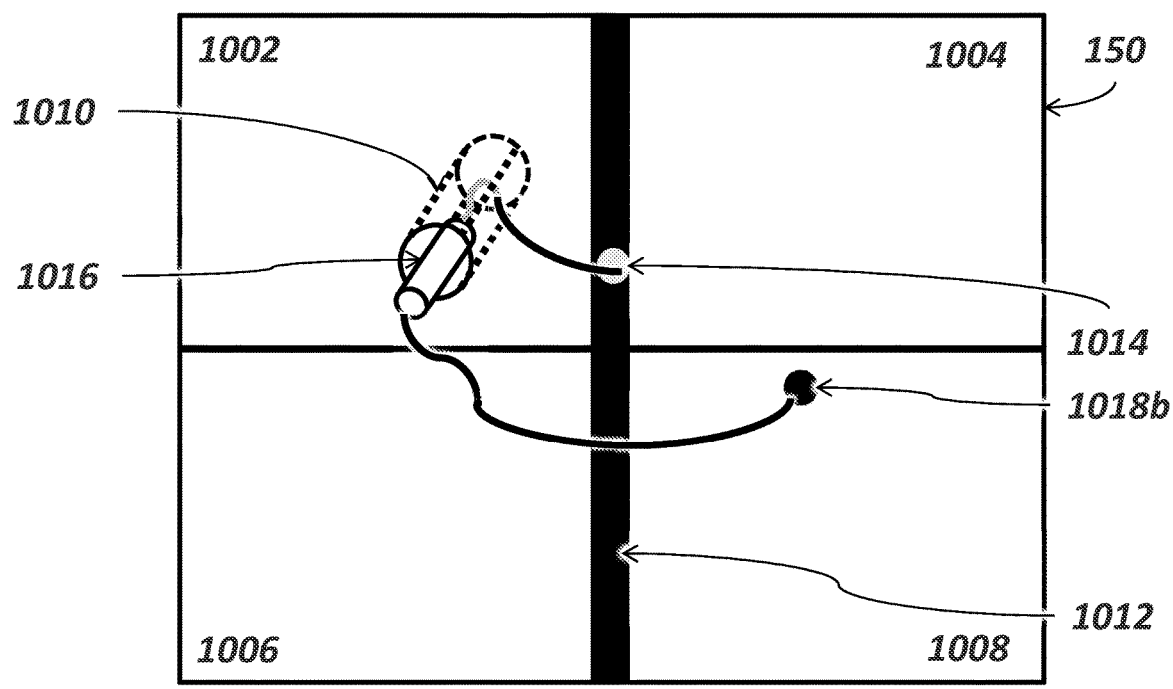

In another example, as shown in FIGS. 11C-D, the heart 150 is paced in two locations, a first location at or near the His bundle 1014, through and near the orifice of the coronary sinus 1010, and a second location 1018b in the upper portion of the left ventricle 1008 (e.g., at a summit of the left ventricle 1008). FIG. 11C shows the second location 1018b being accessed by directing a pacing lead (or electrode) deeper through the coronary sinus 1010 to reach the upper portion of the left ventricle 1008. FIG. 11D shows the second location 1018b being accessed by directing a pacing lead (or electrode) from the right atrium 1002 to the right ventricle 1006 and across the septum 1012 to reach the second location 1018b.

Figure 11E:
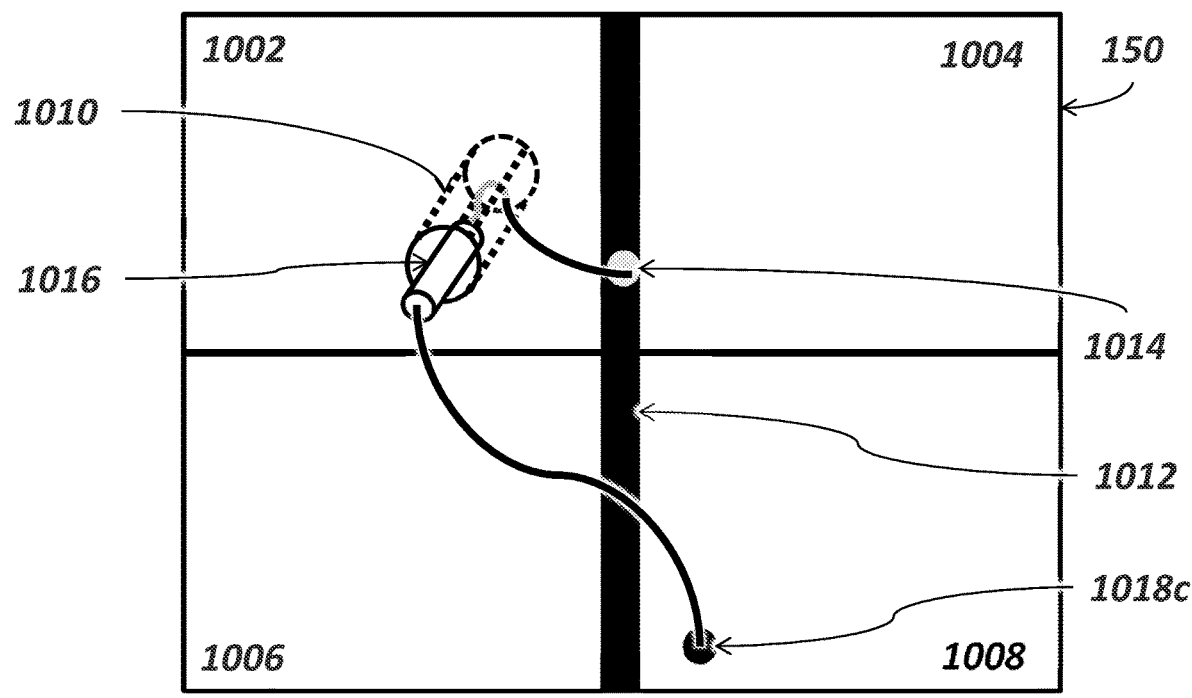

In another example, as shown in FIG. 11E, the heart 150 is paced in two locations, a first location at or near the His bundle 1014, near the orifice of the coronary sinus 1010, and a second location 1018c in the left ventricle 1008 apex, such as by directing a pacing lead (or electrode) from the right atrium 1002 to the right ventricle 1006 and across the septum 1012 to reach the second location 1018c.

Figure 11F:
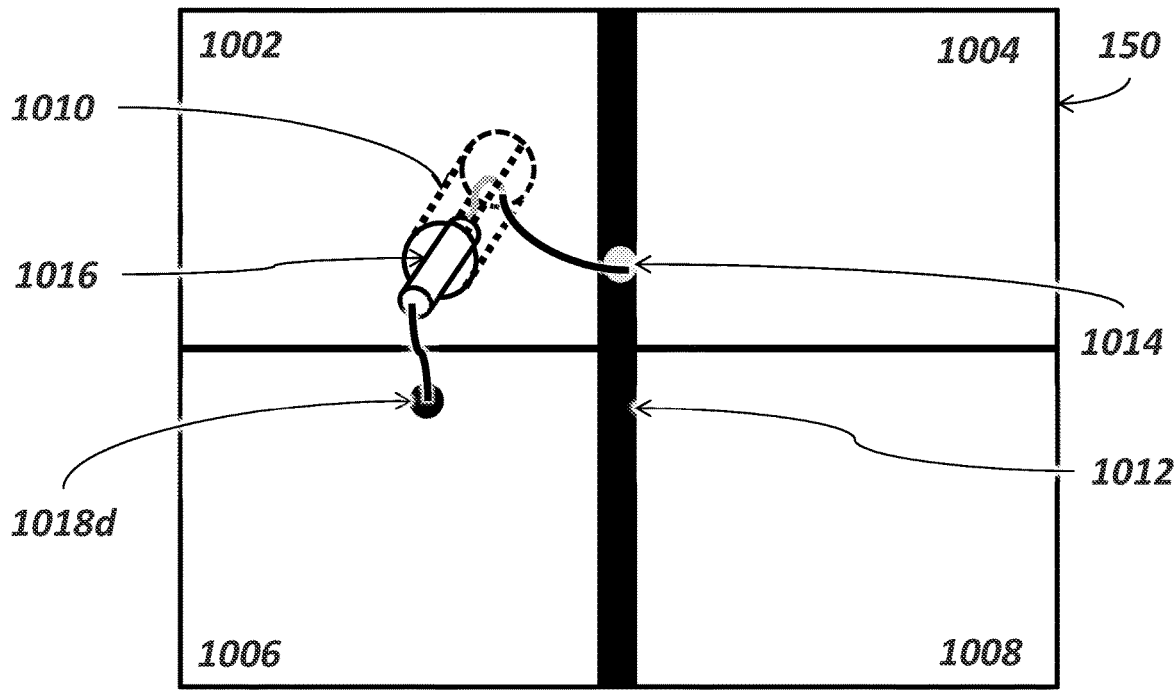

In another example, as shown in FIG. 11F, the heart 150 is paced in two locations, a first location at or near the His bundle 1014, near the orifice of the coronary sinus 1010, and a second location 1018d in the upper portion of the right ventricle 1006 (e.g., at a summit of the right ventricle).

Figure 11G:
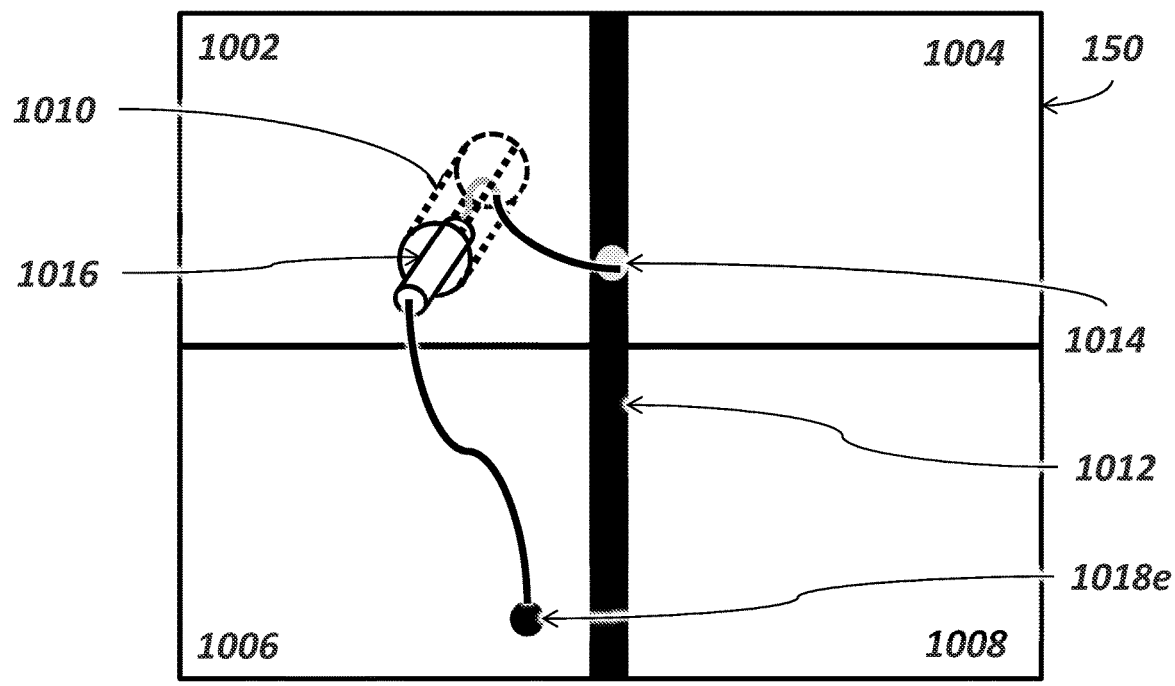

In another example, as shown in FIG. 11G, the heart 150 is paced in two locations, a first location at or near the His bundle 1014, through and near the orifice of the coronary sinus 1010, and a second location 1018e in the right ventricle 1006 apex.

Figure 11H:
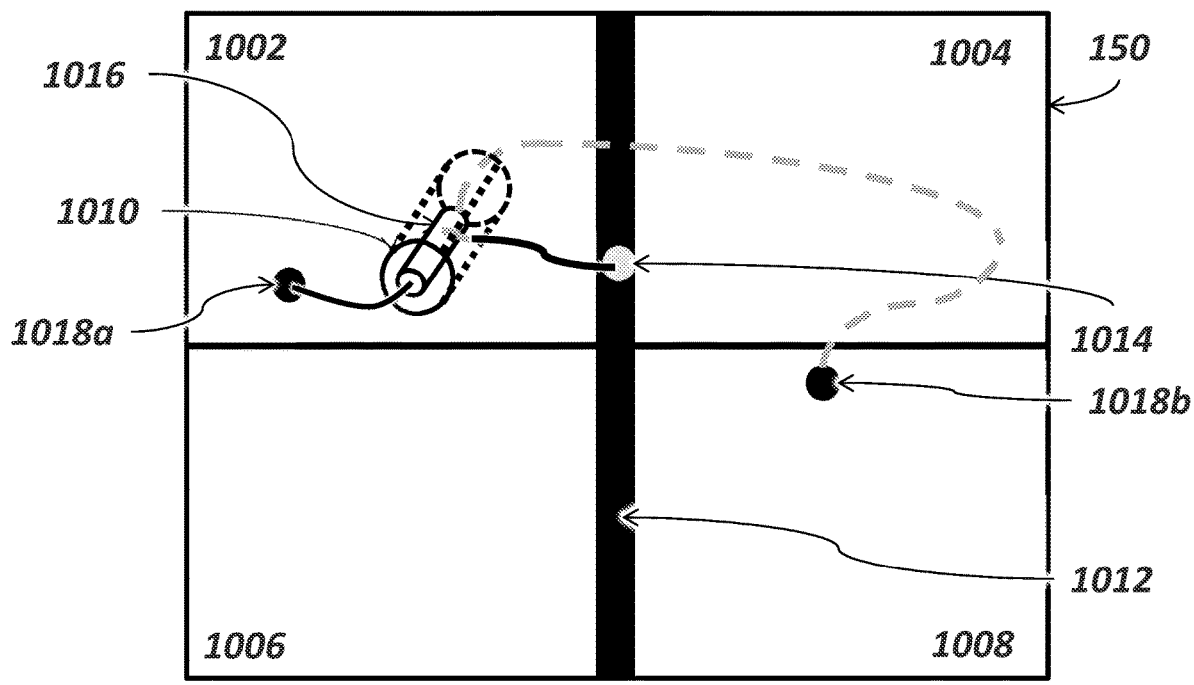
Figure 11I:
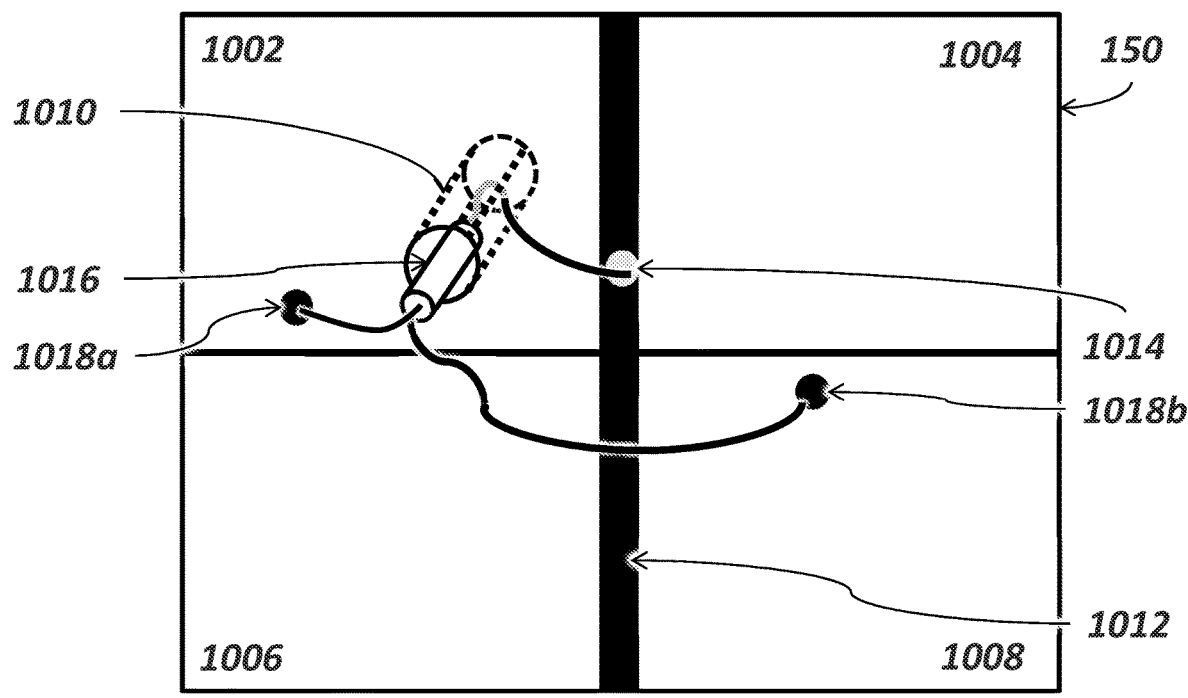
Figure 11J:
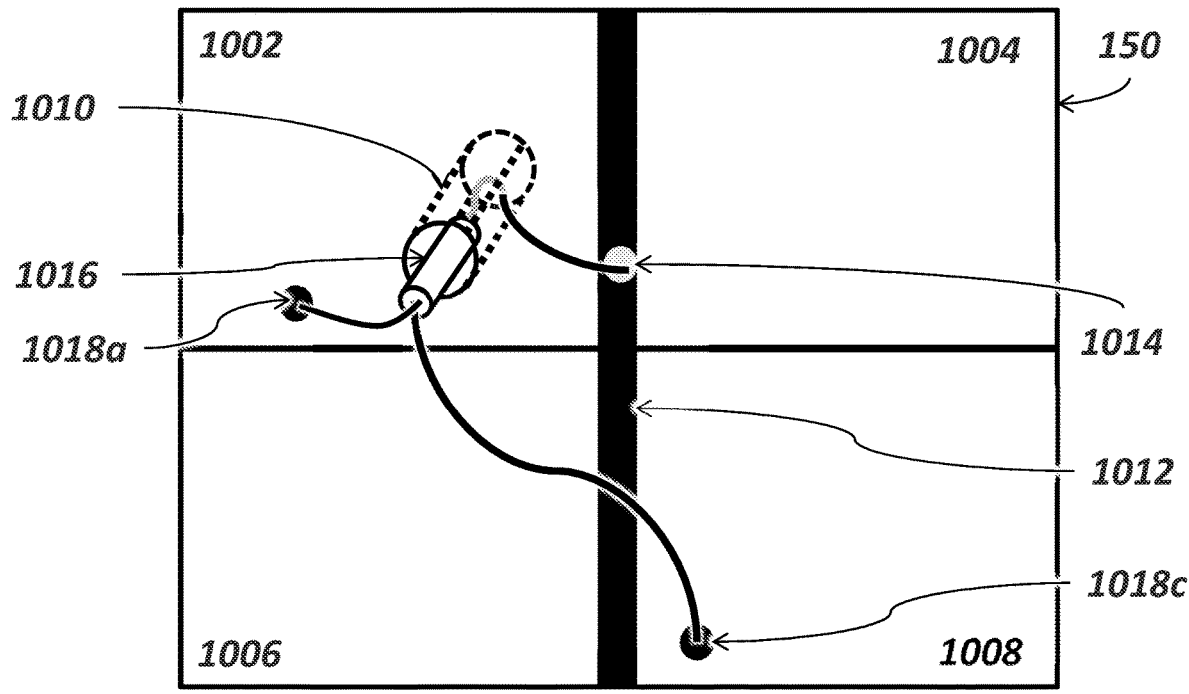

In some instances, three or more pacing locations are contemplated, such as via three pacing leads or using an implantable pacing system with three electrodes. For example, as shown in FIGS. 11H-I, the heart 150 is paced in three locations, a first location at or near the His bundle 1014, through and near the orifice of the coronary sinus 1010, a second location 1018a in the right atrium 1002, and a third location 1018b in the upper portion of the left ventricle 1008 (e.g., summit) FIG. 11H shows the third location 1018b being accessed by directing a pacing lead (or electrode) deeper through the coronary sinus 1010 to reach the upper portion of the left ventricle 1008. FIG. 11I shows the third location 1018b being accessed by directing a pacing lead (or electrode) from the right atrium 1002 to the right ventricle 1006 and across the septum 1012 to reach the third location 1018b. In another example, as shown in FIG. 10J, the heart 150 is paced in three locations, a first location at or near the His bundle 1014, through and near the orifice of the coronary sinus 1010, a second location 1018a in the right atrium 1002, and a third location 1018c in the left ventricle 1008 apex.

Other three pacing location schemes (not illustrated) are also contemplated. For example, the heart 150 is paced in three locations, a first location at or near the His bundle 1014, through and near the orifice of the coronary sinus 1010, a second location 1018a in the right atrium 1002, and a third location 1018d in the upper portion of the right ventricle 1008. In another example, the heart 150 is paced in three locations, a first location at or near the His bundle 1014, through and near the orifice of the coronary sinus 1010, a second location 1018a in the right atrium 1002, and a third location 1018e in the right ventricle 1008 apex.

In other examples (not illustrated), the heart can be paced in four locations, such as at a first location at or near the His bundle 1014, through and near the orifice of the coronary sinus 1010, a second location 1018d in the right ventricle 1006 apex or summit, a third location 1018c in the left ventricle 1008 apex or summit, and a fourth location 1018a in the right atrium 1002. In other examples (not illustrated), the heart can be paced in multiple locations, including a first location at or near the His bundle 1014, a second location in the left atrium 1004 (e.g., by directing a pacing lead or electrode through an atrial septum from the right atrium 1002 to the left atrium 1004), and optionally a third, fourth, and/or nth location.

Figure 11K:
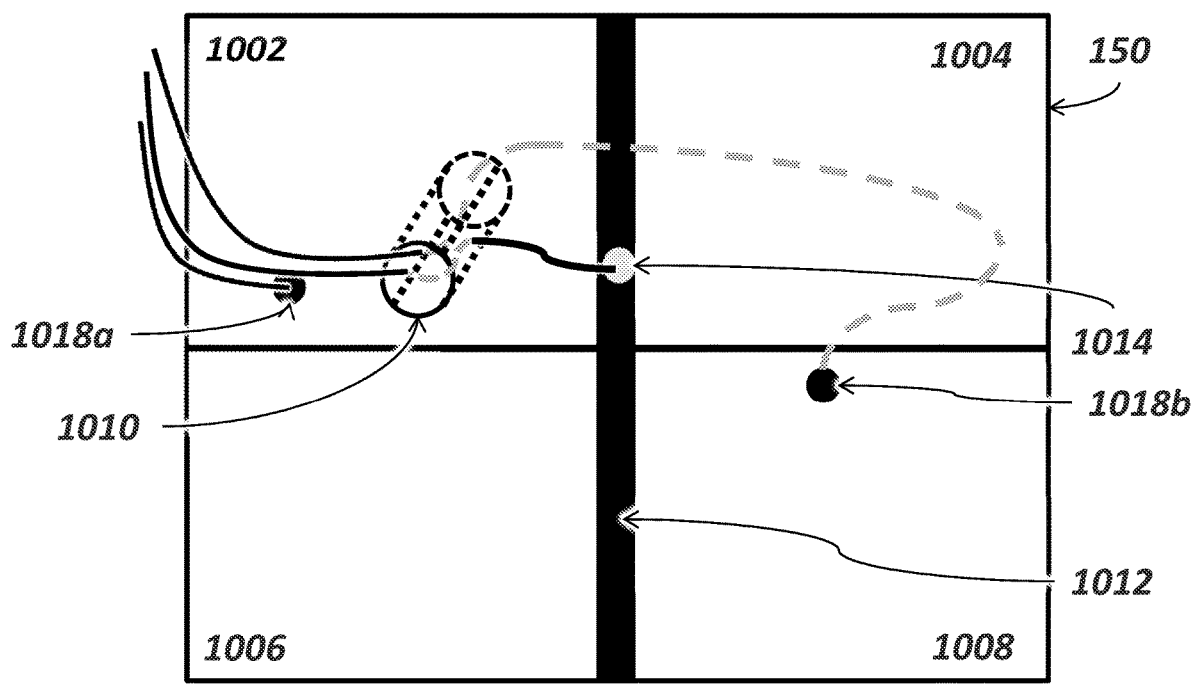
FIG. 11K is a schematic illustration of three pacing leads introduced into the right atrium and directed accordingly to three pacing locations according to embodiments of the present disclosure.

It will be appreciated that while FIGS. 11A-J illustrate the different pacing leads or electrodes for the different pacing locations coupled to an example encasement (e.g., a pacing device, stimulation device, etc.), the pacing device or stimulation device (or the like) may be external to the heart 150. For example, FIG. 11K illustrates three pacing leads introduced into the right atrium 1002 and directed accordingly to the three pacing locations described with respect to FIG. 11I1. The three pacing leads may or may not be coupled to the same pacing device.

An implantable pacing system of the present disclosure may be introduced via the sheaths (e.g., 510, 610, 710) described herein, such as via an introducer device (not illustrated). For example, instead of the pacing catheter 230, an introducer device coupled to the implantable pacing system may be advanced through the lumen 116. Once the distal end of the sheath is disposed at the desired location, the introducer device may lodge the implantable pacing system to couple to the cardiac tissue, such as by coupling a first and/or second electrode. Optionally, the expandable fins may expand upon or during coupling. The sheath may be removed thereafter, and the implantable pacing system may electrically stimulate the heart without physical connections to an external source. In some instances, the implantable pacing system may comprise a wireless transmission system, such as operating on radio frequency, that is able to transmit and/or receive data from an external controller.

IV. KITS

The devices disclosed herein can be combined into kits prior to use. The devices would be sterilized and sealed into suitable packaging designed to prevent contamination. A variety of devices and sizes can be provided in each kit in order to facilitate a surgeon's use of the kit in a sterile patient treating setting, such as a hospital operating room, or clinic. Thus, for example, the kit could contain one or more guidewires of different diameters, lengths, and flexibility; one or more elongate sheaths having different diameters, lengths, and distal tip (e.g., nose) configurations; one or more pacing catheters, having different diameters, different lengths, and with or without the pacing needle incorporated; and/or one or more pacing needles having different tip configurations.

Specific configurations and materials for making catheters, electrodes and pacing leads are known in the art. For example, the following patents are directed to catheters suitable for use in the heart: U.S. Pat. No. 7,099,712 for Catheter having multiple spines each having electrical mapping and location sensing capabilities; U.S. Pat. No. 7,097,641 for Catheter with cryogenic and heating ablation; U.S. Pat. No. 7,089,045 for Catheter and method for mapping Purkinje fibers; U.S. Pat. No. 7,081,114 for Electrophysiology/ablation catheter having lariat configuration of variable radius; U.S. Pat. No. 7,047,068 for Microelectrode catheter for mapping and ablation; U.S. Pat. No. 7,041,079 for Occlusion catheter for the ascending aorta; U.S. Pat. No. 7,039,450 for Telescoping catheter; U.S. Pat. No. 6,987,996 for Catheter having mapping assembly; U.S. Pat. No. 6,986,769 for Ablation catheter with cooled linear electrode; U.S. Pat. No. 6,984,232 for Ablation catheter assembly having a virtual electrode comprising portholes; U.S. Pat. No. 6,973,352 for Steerable cardiac pacing and sensing catheter and guidewire for implanting leads; U.S. Pat. No. 6,973,340 for Basket catheter with improved expansion mechanism; U.S. Pat. No. 6,961,602 for Catheter having multiple spines each having electrical mapping and location sensing capabilities; U.S. Pat. No. 6,960,206 for Coiled ablation catheter system; U.S. Pat. No. 6,947,785 for Interface system for endocardial mapping catheter; U.S. Pat. No. 6,926,669 for Heart wall ablation/mapping catheter and method; U.S. Pat. No. 6,916,317 for Tricuspid annular grasp catheter; U.S. Pat. No. 6,902,545 for Multichannel catheter; U.S. Pat. No. 6,892,091 for Catheter, method and apparatus for generating an electrical map of a chamber of the heart; U.S. Pat. No. 6,839,588 for Electrophysiological cardiac mapping system based on a non-contact non-expandable miniature multi-electrode catheter and method therefor; U.S. Pat. No. 6,837,864 for Multichannel catheter with obturator; U.S. Pat. No. 6,835,188 for Aortic catheter with porous aortic root balloon and methods for inducing cardioplegic arrest; for U.S. Pat. No. 6,830,568 for Guiding catheter system for ablating heart tissue; U.S. Pat. No. 6,826,421 for Endocardial mapping catheter; U.S. Pat. No. 6,821,265 for Multichannel catheter; U.S. Pat. No. 6,807,447 for Triple array defibrillation catheter and method of using the same; U.S. Pat. No. 6,748,255 for Basket catheter with multiple location sensors; U.S. Pat. No. 6,746,431 for Combined catheter system for IABP and determination of thermodilution cardiac output; U.S. Pat. No. 6,741,878 for Basket catheter with improved expansion mechanism; U.S. Pat. No. 6,736,782 for Apparatus, computer program, central venous catheter assembly and method for hemodynamic monitoring; U.S. Pat. No. 6,733,499 for Catheter having circular ablation assembly; U.S. Pat. No. 6,728,563 for Electrophysiology/ablation catheter having "halo" configuration; U.S. Pat. No. 6,723,082 for Delivery catheter system for heart chamber; U.S. Pat. No. 6,723,069 for Electrophysiology positioning catheter; U.S. Pat. No. 7,110,827 for Electrical connectors for medical lead having weld-less wiring connection; U.S. Pat. No. 7,103,409 for Atrial and ventricular implantable cardioverter-defibrillator and lead system; U.S. Pat. No. 7,089,065 for Modified guidewire for left ventricular access lead; U.S. Pat. No. 7,085,606 for Epicardial electrode; U.S. Pat. No. 7,031,773 for Implantable cardiac stimulation system providing auto-capture and lead impedance assessment and method; U.S. Pat. No. 7,027,876 for Lead system for providing electrical stimulation to the Bundle of His; U.S. Pat. No. 7,010,358 for Single lead system for high voltage CHF device; U.S. Pat. No. 6,999,821 for Body implantable lead including one or more conductive polymer electrodes and methods for fabricating same; U.S. Pat. No. 6,999,814 for Implantable intravenous cardiac stimulation system with pulse generator housing serving as optional additional electrode; U.S. Pat. No. 6,988,007 for Single pass telescoping cardiac lead for the left heart; U.S. Pat. No. 6,987,999 for Implantable defibrillator with alternating counter electrode; U.S. Pat. No. 6,986,769 for Ablation catheter with cooled linear electrode; U.S. Pat. No. 6,984,232 for Ablation catheter assembly having a virtual electrode comprising portholes; U.S. Pat. No. 6,973,341 for Noninvasive, intrauterine fetal ECG strip electrode; U.S. Pat. No. 6,970,733 for System and method for electrode localization using ultrasound; U.S. Pat. No. 6,968,237 for Implantable coronary sinus lead and lead system; U.S. Pat. No. 6,961,621 for Apparatus and method for stabilizing an implantable lead; U.S. Pat. No. 6,950,696 for Method and circuit for detecting cardiac rhythm abnormalities by analyzing time differences between unipolar signals from a lead with a multi-electrode tip; U.S. Pat. No. 6,944,506 for Stylet feature for resisting perforation of an implantable lead; U.S. Pat. No. 6,934,583 for Implantable lead and method for stimulating the vagus nerve; U.S. Pat. No. 6,909,919 for Cardiac lead incorporating strain gauge for assessing cardiac contractility; U.S. Pat. No. 6,909,916 for Cardiac rhythm management system with arrhythmia classification and electrode selection; U.S. Pat. No. 6,907,297 for Expandable intracardiac return electrode and method of use; U.S. Pat. No. 6,907,296 for Implantable cardiac lead having convenient implant location identification and method of manufacture; U.S. Pat. No. 6,904,315 for Atrial aware VVI: a method for atrial synchronous ventricular (VDD/R) pacing using the subcutaneous electrode array and a standard pacing lead; U.S. Pat. No. 6,901,297 for Stimulation electrode and its use; U.S. Pat. No. 6,901,288 for Sealing assembly for intravenous lead; U.S. Pat. No. 6,889,093 for Electrode lead with multiple branches; U.S. Pat. No. 6,882,886 for Vessel electrode line; U.S. Pat. No. 6,868,291 for Arrangement for implanting an endocardial cardiac lead; U.S. Pat. No. 6,859,667 for Multiplexed medical device lead with standard header; U.S. Pat. No. 6,850,800 for Evoked response detector, averaging the value of the amplitude of the picked-up electrode signal; U.S. Pat. No. 6,849,073 for Apparatus and method for creating, maintaining, and controlling a virtual electrode used for the ablation of tissue; U.S. Pat. No. 6,839,588 for Electrophysiological cardiac mapping system based on a non-contact non-expandable miniature multi-electrode catheter and method therefor; U.S. Pat. No. 6,823,215 for Implantable heart stimulator with microinstability testing for electrode contact with tissue; U.S. Pat. No. 6,804,553 for Bachmann's bundle electrode for atrial defibrillation; U.S. Pat. No. 6,792,318 for Technique for fixating a lead; U.S. Pat. No. 6,792,316 for Cardiac implant cable having a coaxial lead; U.S. Pat. No. 6,788,972 for Implantable cardiac stimulator with electrode-tissue interface characterization; U.S. Pat. No. 6,782,291 for Implantable cardiac stimulation device with automatic evoked response sensing electrode configuration selection and method; U.S. Pat. No. 6,775,566 for Electrode structure and heart rate measuring arrangement While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pacing device for pacing the heart of a patient, comprising:
   (i) an encasement including therein a pulse generator; and
   (ii) a pacing electrode protruding from a distal end of the encasement, wherein the pacing electrode is electrically coupled to the pulse generator and comprises:
      (a) a linear segment extending at a distal tip of the pacing electrode, wherein the linear segment is configured to pierce cardiac tissue at a target location to a first depth of the cardiac tissue for testing the placement of the pacing electrode at the target location, and
      (b) a helical segment at a proximal end of the linear needle, wherein the helical segment is configured to screw into the target location, thereby advancing the linear needle to a second depth of the cardiac tissue and anchoring the pacing electrode to the target location.

2. The pacing device of claim 1, wherein the helical segment comprises a straight coil-like feature.

3. The pacing device of claim 1, wherein the helical segment comprises a conical coil-like feature.

4. The pacing device of claim 3, wherein the apex angle of the conical coil-like feature is between 0° and 180°.

5. The pacing device of claim 1, wherein the linear segment and the helical segment form a single continuous anchor structure.

6. The pacing device of claim 1, wherein the pulse generator is configured to achieve pacing of the His bundle.

7. The pacing device of claim 1, wherein the target location is within the coronary sinus, and wherein the pacing electrode is configured to anchor to cardiac tissue through a wall of the coronary sinus.

8. The pacing device of claim 1, wherein the linear segment has a length of at least 0.5 millimeters.

9. The pacing device of claim 8, wherein the linear segment has a length of at most 1 centimeter.

10. The pacing device of claim 1, wherein the pulse generator comprises a second electrode.

11. The pacing device of claim 10, wherein the second electrode is disposed on a lateral surface of the encasement.

12. The pacing device of claim 10, wherein the second electrode is positioned at a proximal end of the encasement.

13. The pacing device of claim 10, wherein the second electrode is configured to couple to an atrial wall.

14. The pacing device of claim 13, wherein the pacing device is configured to achieve pacing of both the right atrial wall and the His bundle.

15. A system for pacing the heart of the patient comprising an elongate sheath configured to be at least partially advanced to a coronary sinus in the heart, the elongate sheath comprising a proximal end, a distal end, and a lumen sized and dimensioned for advancing a pacing device through the lumen, wherein the distal end of the sheath is configured to be disposed at a target location at or proximal to the His bundle; and the pacing device of claim 1.

16. A method for pacing a heart of a patient, the method comprising:
   (a) introducing a sheath into the right atrium of the heart of the patient;
   (b) advancing a distal end of a pacing electrode through a lumen of the sheath to a target location, the distal end of the pacing electrode comprising:
      (i) a linear segment extending at a distal tip of the pacing electrode, wherein the linear segment is configured to pierce cardiac tissue to a first depth of the cardiac tissue for testing the placement of the pacing electrode at the target location, and
      (ii) a helical segment at a proximal end of the linear needle, wherein the helical segment is configured to screw into the target location, thereby advancing the linear needle to a second depth of the cardiac tissue and anchoring the pacing electrode to the target location;
   (c) (i) coupling the linear segment of the pacing electrode to a cardiac tissue at the target location, (ii) activating the pacing electrode to generate a first diagnostic result, (iii) acquiring the first diagnostic result, and (iv) determining whether the pacing electrode at the target location is efficacious based on the first diagnostic result;
   (d) coupling the helical feature of the pacing electrode to the cardiac tissue at the target location if the pacing electrode at the target location is determined to be efficacious based on the first diagnostic result; and
   (e) electrically pacing the target location using the pacing electrode.

17. The method of claim 16, wherein the target location is at or proximal to the His bundle.

18. The method of claim 16, wherein the target location is within the coronary sinus.

19. The method of claim 16, wherein the pacing electrode is a first pacing electrode, wherein the target location is a first target location, and wherein the method further comprises advancing a second pacing electrode through the lumen of the sheath to a second target location.

20. The method of claim 19, further comprising electrically pacing the second target location using the second pacing electrode.

* * * * *